United States Patent
Tapper et al.

(10) Patent No.: US 10,272,257 B2
(45) Date of Patent: Apr. 30, 2019

(54) LIGHT THERAPY PLATFORM INDUCTIVE MASK AND CHARGER

(71) Applicant: Johnson & Johnson Consumer Inc., Skillman, NJ (US)

(72) Inventors: Jay Tapper, Wayne, PA (US); David Shuter, Palm Beach Gardens, FL (US); Charles Peter Althoff, New York, NY (US); Kayla Marie Nickley, Jersey City, NJ (US)

(73) Assignee: Johnson & Johnson Consumer, Inc., Skillman, NJ (US)

( * ) Notice: Subject to any disclaimer, the term of this patent is extended or adjusted under 35 U.S.C. 154(b) by 0 days.

(21) Appl. No.: 14/747,392

(22) Filed: Jun. 23, 2015

(65) Prior Publication Data
US 2016/0051834 A1 Feb. 25, 2016

Related U.S. Application Data

(60) Continuation-in-part of application No. 14/324,453, filed on Jul. 7, 2014, which is a division of application
(Continued)

(51) Int. Cl.
*A61B 17/00* (2006.01)
*A61N 5/06* (2006.01)
(Continued)

(52) U.S. Cl.
CPC ............ *A61N 5/0616* (2013.01); *A61F 9/045* (2013.01); *A61B 2017/00057* (2013.01);
(Continued)

(58) Field of Classification Search
CPC ..... A61B 18/203; H01F 17/0006; A61N 5/06; A61F 9/054; A61F 9/05; G05B 7/02; H02J 7/025
(Continued)

(56) References Cited

U.S. PATENT DOCUMENTS 1,626,617 A 5/1927 Last
1,692,669 A 11/1928 Last
(Continued)

FOREIGN PATENT DOCUMENTS

CN 1738663 A 2/2006
DE 20 20009 000 891 U1 7/2009
(Continued)

OTHER PUBLICATIONS

PCT/US2014/069789—PCT Notification Concerning Transmittal of Int'l Preliminary Report on Patentability dated Jun. 23, 2016 (Johnson & Johnson Consumer, Inc.).
(Continued)

*Primary Examiner* — Aaron F Roane
(74) *Attorney, Agent, or Firm* — Fay Sharpe LLP

(57) ABSTRACT

Disclosed is a therapeutic lamp platform inductive mask and charger. According to an exemplary embodiment of this disclosure, provided is a phototherapy system comprising a phototherapy device including a plurality of radiant lamps disposed to communicate radiant energy to a user treatment area, a rechargeable power source, and a controller operatively associated with controlling a delivery of the radiant energy to the user treatment area, wherein the plurality of radiant lamps, the rechargeable power source and controller are housed by a mask shaped therapeutic lamp platform wherein the phototherapy device is configured to inductively charge the rechargeable battery; and an inductive charger configured to charge the phototherapy device rechargeable battery.

19 Claims, 50 Drawing Sheets

Related U.S. Application Data

No. 13/604,012, filed on Sep. 5, 2012, now Pat. No. 8,771,328, application No. 14/747,392, filed on Jun. 23, 2015, which is a continuation-in-part of application No. 14/567,552, filed on Dec. 11, 2014, now Pat. No. 9,789,333.

(60) Provisional application No. 61/532,140, filed on Sep. 8, 2011, provisional application No. 61/914,624, filed on Dec. 11, 2013.

(51) Int. Cl.
*A61F 9/04* (2006.01)
*A61B 18/00* (2006.01)
*A61N 5/067* (2006.01)
*A61B 90/00* (2016.01)

(52) U.S. Cl.
CPC .............. *A61B 2018/00642* (2013.01); *A61B 2018/00791* (2013.01); *A61B 2018/00988* (2013.01); *A61B 2090/049* (2016.02); *A61N 2005/067* (2013.01); *A61N 2005/0626* (2013.01); *A61N 2005/0627* (2013.01); *A61N 2005/0628* (2013.01); *A61N 2005/0647* (2013.01); *A61N 2005/0652* (2013.01); *A61N 2005/0654* (2013.01); *A61N 2005/0659* (2013.01); *A61N 2005/0663* (2013.01); *A61N 2005/0666* (2013.01)

(58) Field of Classification Search
USPC .......................................... 607/93; 320/108
See application file for complete search history.

(56) References Cited

U.S. PATENT DOCUMENTS

| | | | |
|---|---|---|---|
| 3,279,468 A | 10/1966 | Le Vine | |
| 3,376,870 A | 4/1968 | Yamamoto et al. | |
| 3,971,387 A | 7/1976 | Mantell | |
| 5,085,227 A | 2/1992 | Ramon | |
| 5,616,140 A | 4/1997 | Prescott | |
| 5,824,023 A | 10/1998 | Anderson | |
| 5,913,883 A | 6/1999 | Alexander et al. | |
| 6,045,575 A | 4/2000 | Rosen et al. | |
| 6,290,713 B1 | 9/2001 | Russell | |
| 6,293,900 B1 | 9/2001 | Bove et al. | |
| 6,350,275 B1 | 2/2002 | Vreman | |
| 6,443,978 B1 | 9/2002 | Zharov | |
| 6,471,716 B1 | 10/2002 | Pecukonis | |
| 6,508,813 B1 | 1/2003 | Altshuler | |
| 6,511,475 B1 | 1/2003 | Altshuler et al. | |
| 6,517,532 B1 | 2/2003 | Altshuler et al. | |
| 6,743,249 B1 | 6/2004 | Alden | |
| 6,824,265 B1 | 11/2004 | Harper | |
| 6,860,896 B2 | 3/2005 | Leber et al. | |
| 7,125,416 B2 | 10/2006 | Kent et al. | |
| 7,164,255 B2* | 1/2007 | Hui .................... | H01F 17/0006 320/108 |
| 7,222,995 B1 | 5/2007 | Bayat et al. | |
| 7,414,380 B2* | 8/2008 | Tang ....................... | H02J 7/025 320/108 |
| 7,438,409 B2 | 10/2008 | Jordan | |
| 7,520,630 B2 | 4/2009 | Murphy | |
| 7,824,241 B2 | 11/2010 | Duprey | |
| 8,192,473 B2 | 6/2012 | Tucker et al. | |
| 8,252,033 B2 | 8/2012 | Tucker et al. | |
| 8,491,118 B2 | 7/2013 | Waters | |
| 8,771,328 B2 | 7/2014 | Tapper et al. | |
| 8,858,607 B1 | 10/2014 | Jones | |
| 2003/0199800 A1 | 10/2003 | Levin | |
| 2004/0162549 A1 | 8/2004 | Altshuler | |
| 2005/0070977 A1 | 3/2005 | Molina | |
| 2005/0080465 A1 | 4/2005 | Zelickson et al. | |
| 2005/0182460 A1 | 8/2005 | Kent | |
| 2005/0278003 A1 | 12/2005 | Feldman | |
| 2006/0173514 A1 | 8/2006 | Biel et al. | |
| 2006/0217690 A1 | 9/2006 | Bastin et al. | |
| 2006/0217787 A1 | 9/2006 | Olson et al. | |
| 2006/0268220 A1 | 11/2006 | Hogan | |
| 2007/0032847 A1* | 2/2007 | Weckwerth .......... | A61B 18/203 607/93 |
| 2007/0156208 A1 | 7/2007 | Havell et al. | |
| 2007/0208395 A1 | 9/2007 | Leclerc et al. | |
| 2007/0233208 A1 | 10/2007 | Kurtz et al. | |
| 2008/0065056 A1 | 3/2008 | Powell et al. | |
| 2008/0269849 A1 | 10/2008 | Lewis | |
| 2009/0143842 A1 | 6/2009 | Cumbie et al. | |
| 2009/0192437 A1 | 7/2009 | Soltz et al. | |
| 2010/0001685 A1* | 1/2010 | Eastlack ................. | H02J 7/025 320/108 |
| 2010/0069898 A1 | 3/2010 | O'Neil et al. | |
| 2010/0121419 A1 | 5/2010 | Douglas | |
| 2011/0015707 A1 | 1/2011 | Tucker et al. | |
| 2011/0040355 A1 | 2/2011 | Francis | |
| 2011/0160814 A2 | 6/2011 | Tucker et al. | |
| 2011/0257467 A1 | 10/2011 | Clegg et al. | |
| 2012/0116485 A1 | 5/2012 | Burgmann | |
| 2012/0323064 A1 | 12/2012 | Kim | |

FOREIGN PATENT DOCUMENTS

| | | | |
|---|---|---|---|
| EP | 1 074 275 A1 | 2/2001 | |
| EP | 1 916 016 A1 | 4/2008 | |
| GB | 2 380 134 A | 4/2003 | |
| WO | WO2004052238 | 12/2003 | |
| WO | WO 2006/028461 A2 | 3/2006 | |
| WO | WO 2009047769 A2 * | 4/2009 | ............... G06F 1/26 |
| WO | WO 2010/076707 A1 | 7/2010 | |
| WO | WO2011049419 | 10/2010 | |

OTHER PUBLICATIONS

PCT/US2016/038606—PCT Notification Concerning Transmittal of Int'l Preliminary Report on Patentability dated Nov. 15, 2016 (Johnson & Johnson Consumer, Inc.).
PCT/US2016/038607—PCT Notification Concerning Transmittal of Int'l Preliminary Report on Patentability dated Sep. 29, 2016 (Johnson & Johnson Consumer, Inc.).
PCT/US2016/038608—PCT Notification Concerning Transmittal of Int'l Preliminary Report on Patentability dated Sep. 29, 2016 (Johnson & Johnson Consumer, Inc.).
PCT/US2016/038612—PCT Notification Concerning Transmittal of Int'l Preliminary Report on Patentability dated Sep. 29, 2016 (Johnson & Johnson Consumer, Inc.).

* cited by examiner

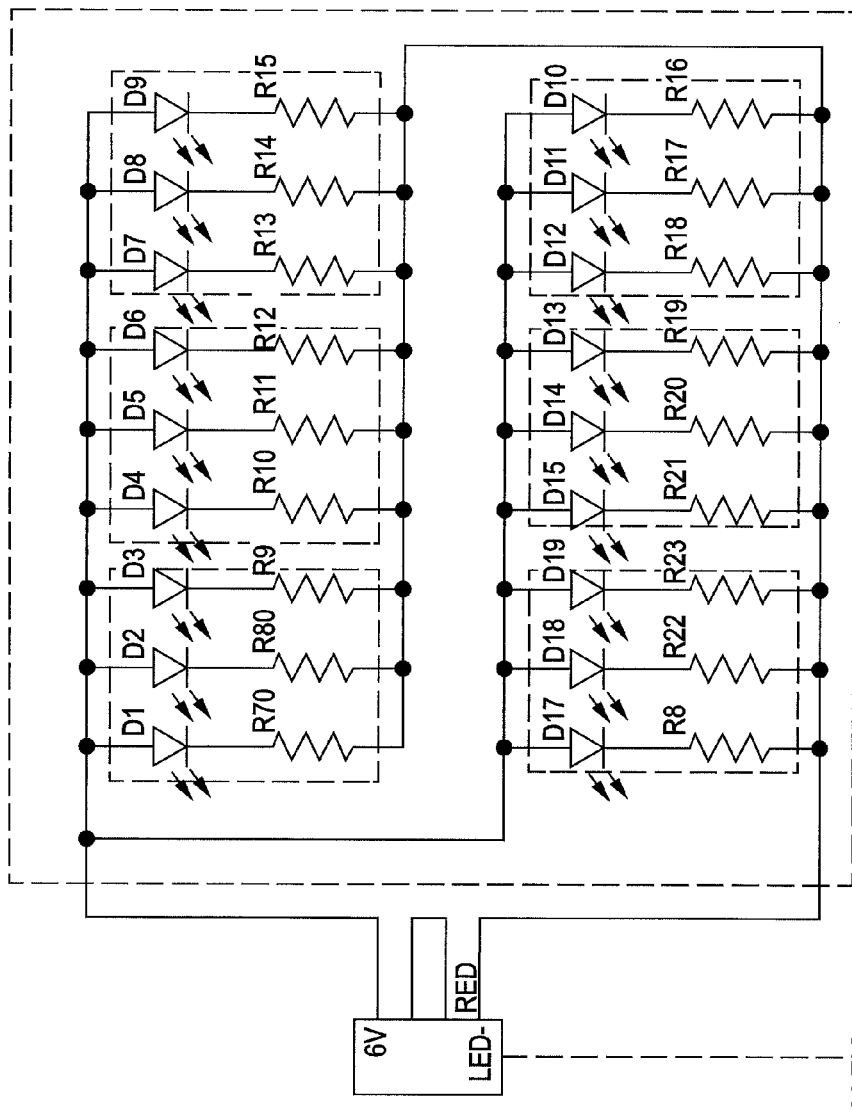

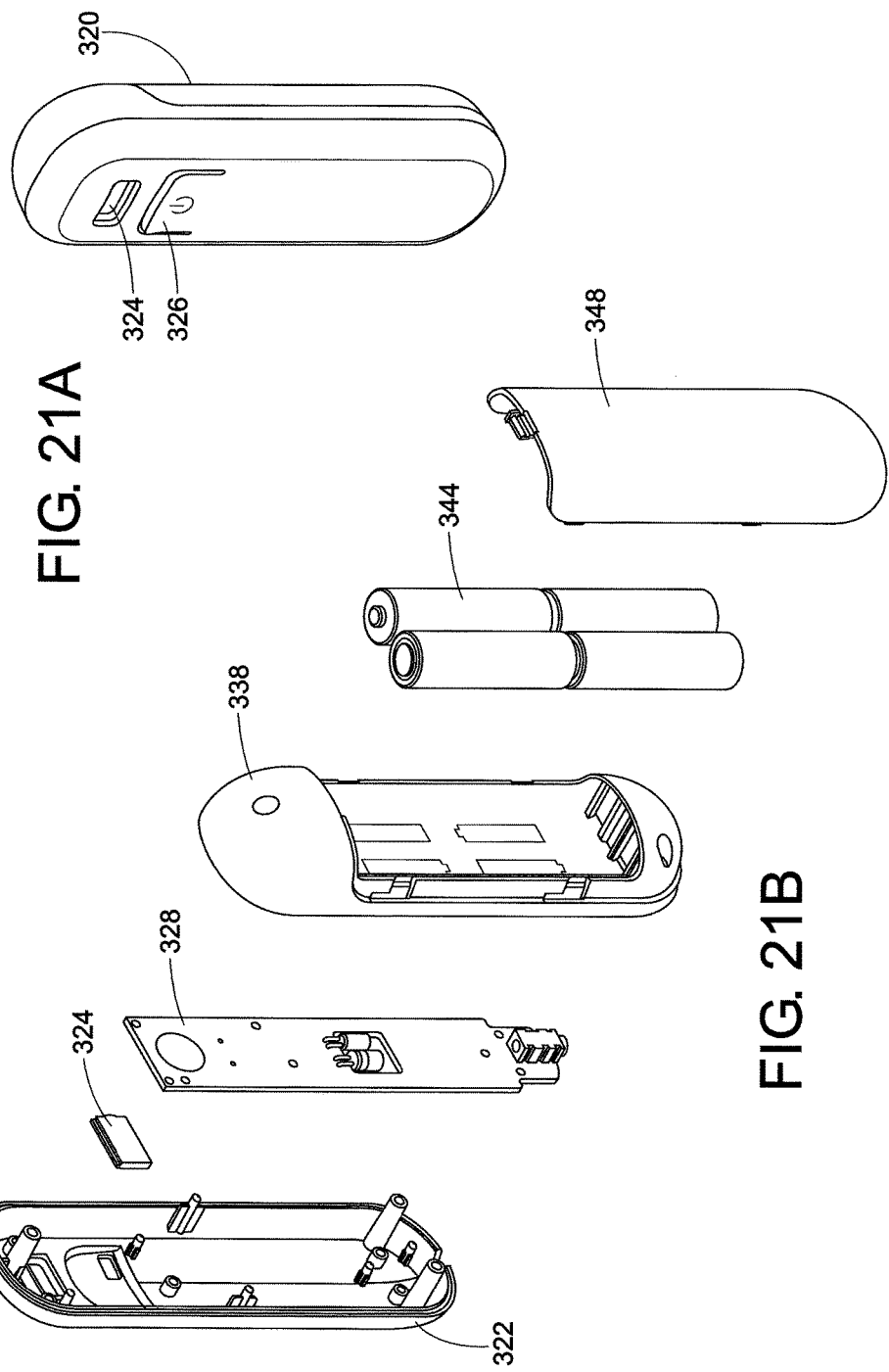

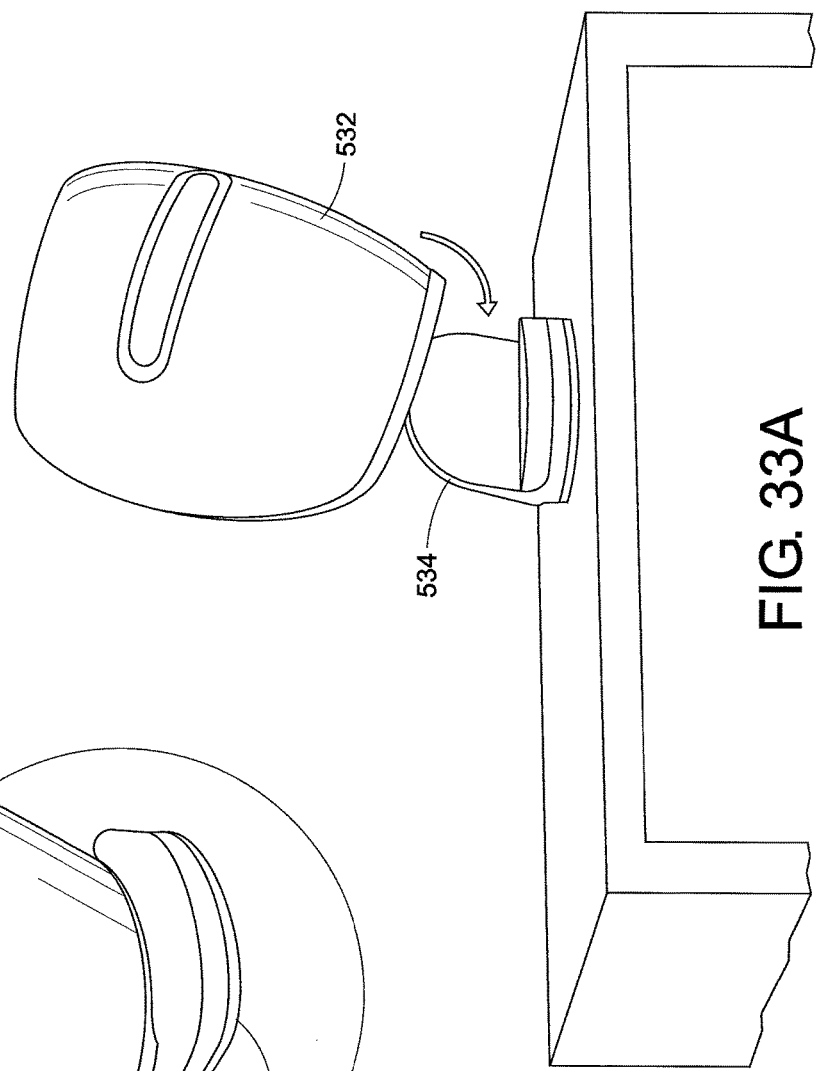
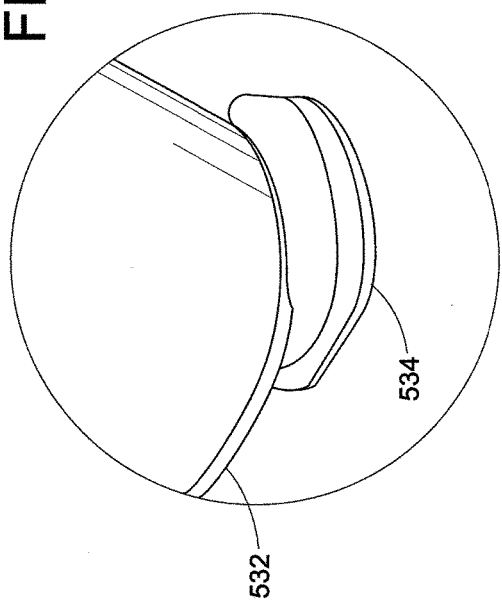

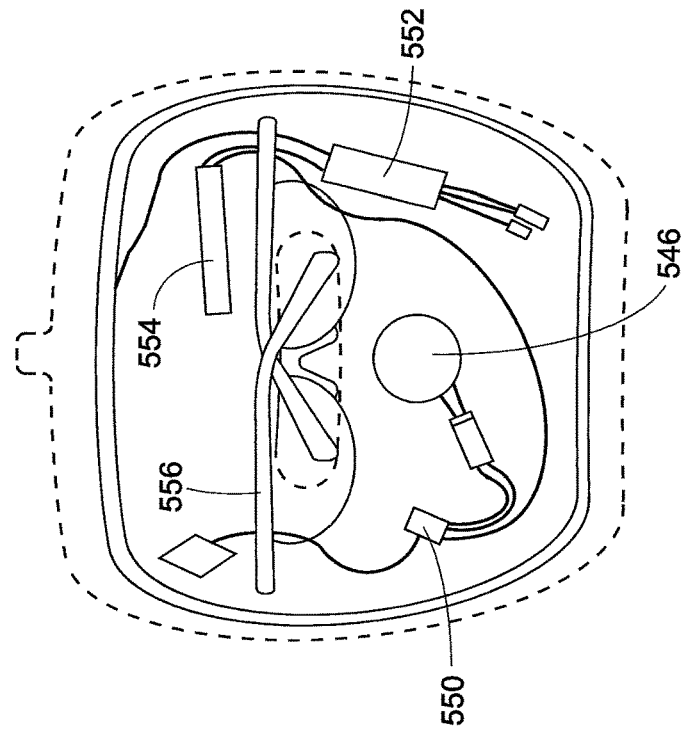
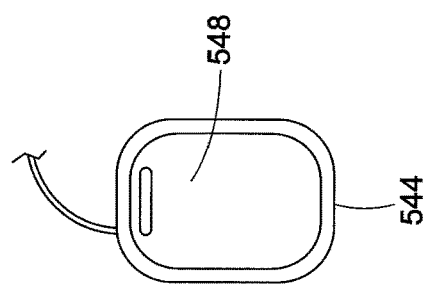
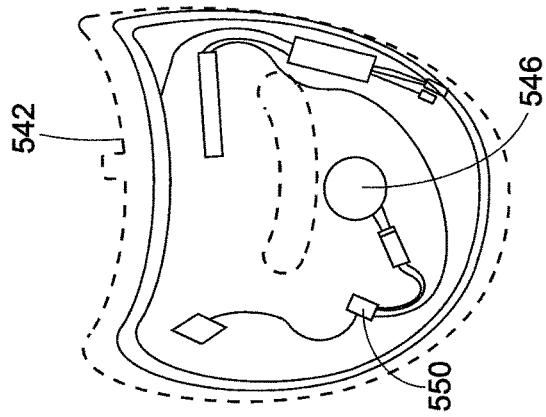
FIG. 34B
FIG. 34A

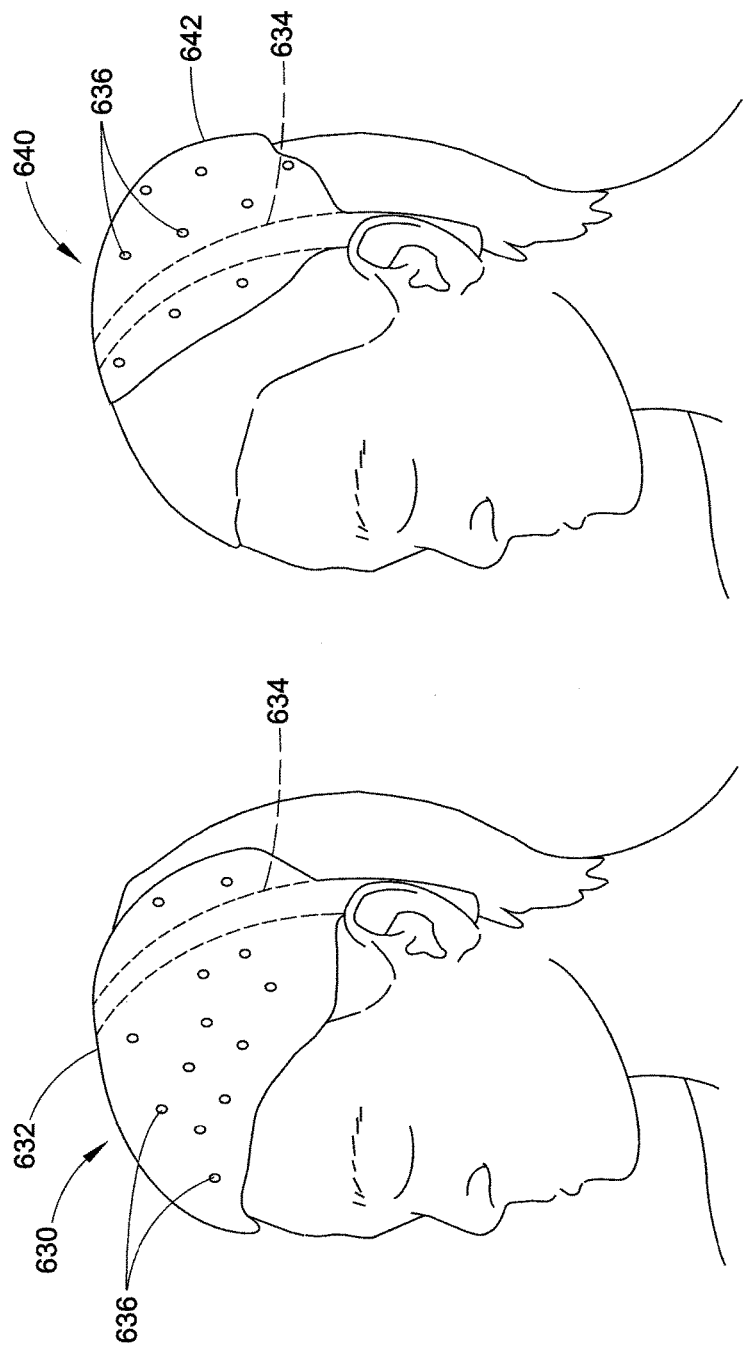

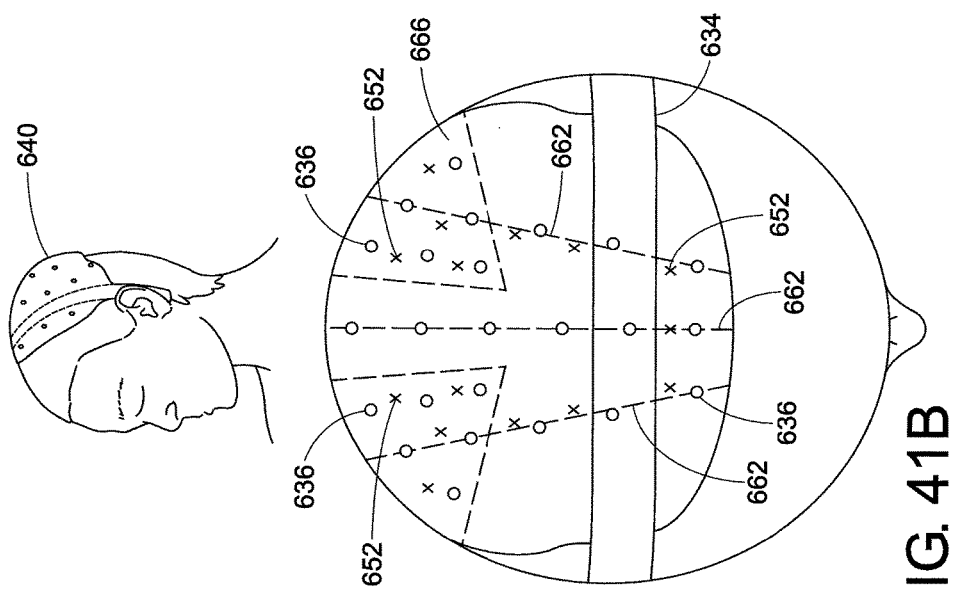
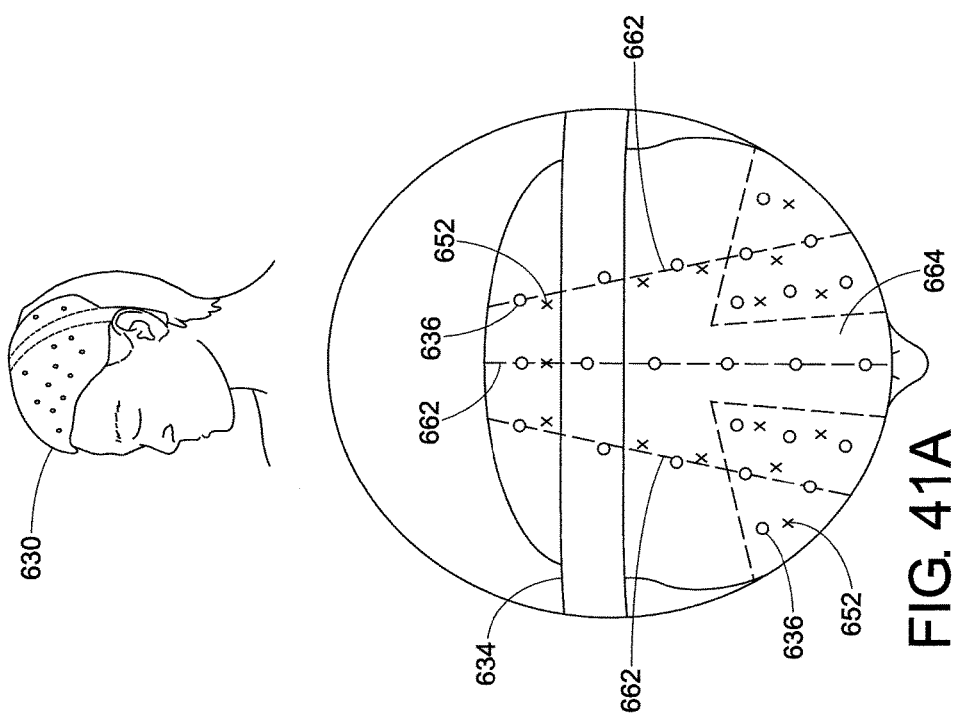
FIG. 41B
FIG. 41A

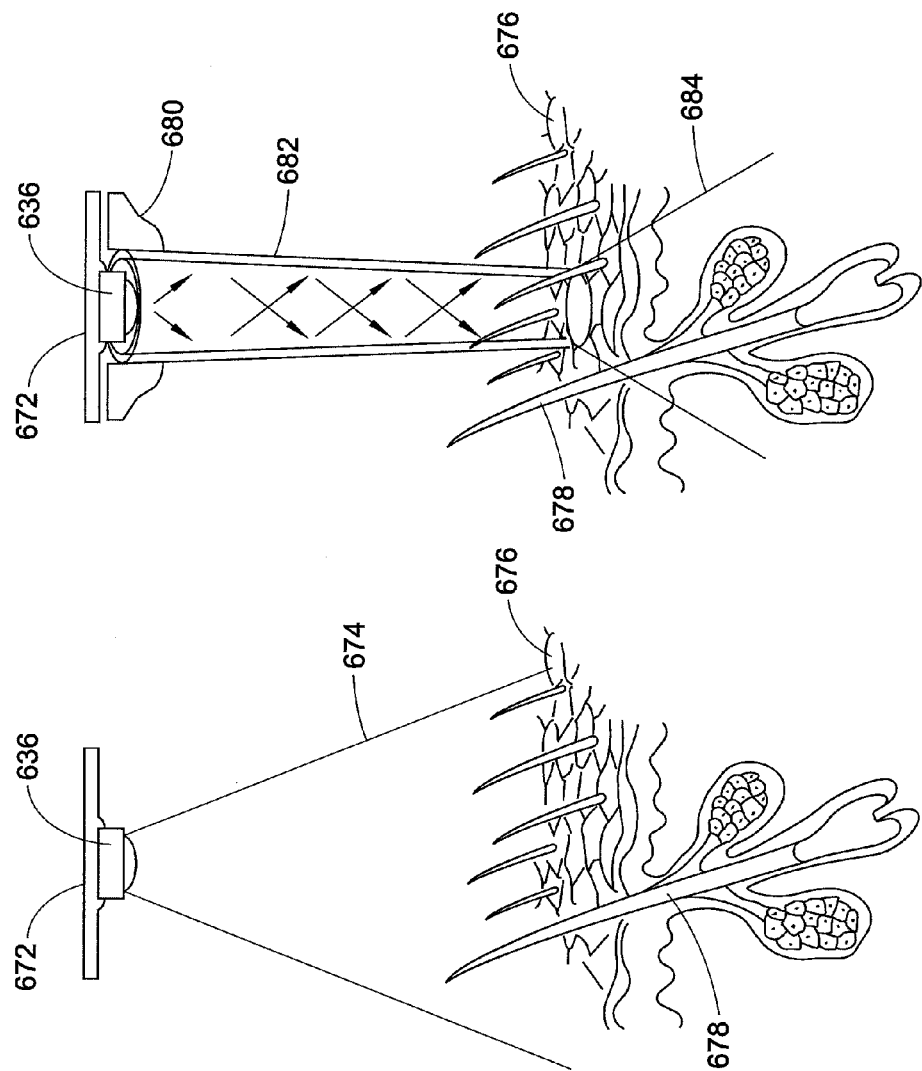

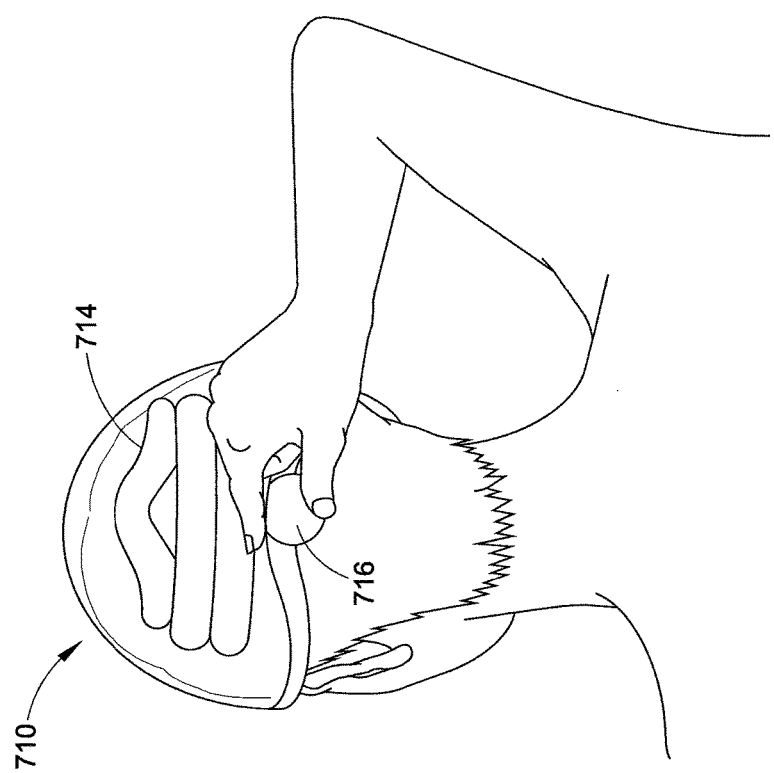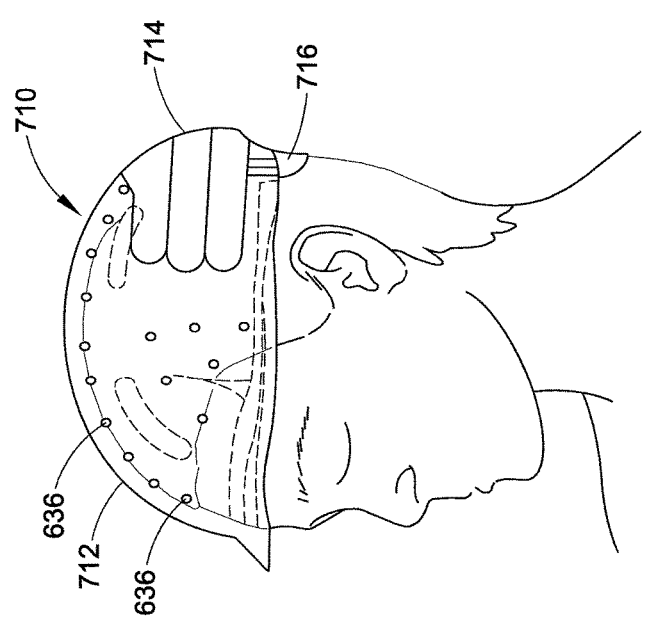
FIG. 46A
FIG. 46B

LIGHT THERAPY PLATFORM INDUCTIVE MASK AND CHARGER

This application is a continuation-in-part of U.S. patent application Ser. No. 14/324,453, filed on Jul. 7, 2014, which is a divisional of U.S. patent application Ser. No. 13/604,012, filed Sep. 5, 2012, now U.S. Pat. No. 8,771,328, which claims priority from U.S. Provisional Patent Application Ser. No. 61/532,140, filed Sep. 8, 2011, and this application is a continuation-in-part of U.S. patent application Ser. No. 14/567,552, filed Dec. 11, 2014, which claims priority to U.S. Provisional Patent Application Ser. No. 61/914,624, filed Dec. 11, 2013, the disclosures of which are incorporated herein by reference.

FIELD

The present embodiments relate to devices and methods for delivering light-based skin therapy treatments for improving skin health, such as anti-aging enhancement or acne prevention, using light-emitting diode (LED) light therapy, although other types of light radiating sources can be used.

BACKGROUND

Certain light spectrums emitted by LEDs (blue or red) are known to be therapeutic for skin treatment against maladies such as acne, or are beneficial to inhibit skin aging. However, there is a need to provide users/patients with a convenient at-home light therapy delivery device such as a wearable mask, veil or hood that is adjustable or flexible to conform to different sizes and shapes, and that is simple to use without user discomfort. Currently available at-home, consumer usable products on the market are fixed to one-size and/or usually have to be hand-held; which generally have not proven satisfactory for providing the best or desired light dispersion. The alternative is customers visiting a doctor's office to receive treatments.

Prior known light therapy devices, particularly masks, have suffered from problems relating to the exposure of the LEDs and the associated circuitry to power the LEDs to contact by users. More particularly, in an effort to maximize light communication to a patient, the LEDs have been disposed in a manner which allow them to be physically engaged (e.g., touched) by a patient, or even contact a treatment surface, which processes are debilitating to the LEDs as a result of the accumulation of dirt and oil. In addition, any such engagement can be dangerous to patients who are exposed to the sharp or hot edges of the LEDs and the associated circuitry. The exposure of detailed circuitry presents an intimidating and unpleasant experience when the therapy requires several minutes of time for completion and the mask is disposed relatively close to the face, often causing an uncomfortable, claustrophobic sensation over time to the patient.

A hands-free therapeutic experience is always better than having to hold the device in a particular position for extended periods of time during the therapy. Numerous assemblies have been conceived for mounting masks and helmet-like devices to varieties of straps, bands, wraps and cords, which can result in a pressing of the support and mounting assembly closely against the hair or scalp of a patient. There is always a need to minimize the extent of such attachment assemblies so that on the one hand the subject device is securely attached on the patient, but also that the attaching structure has minimal consequence to the patient's comfort during the therapy itself. Being relatively light in weight, and easily and minimally supported during therapeutic use are important to consumer acceptance.

As users come in a variety of shapes and sizes, devices should be size or area adjustable so that the therapy can be efficiently applied and/or selectively intensified to desired treatment areas.

Lastly, particularly in therapeutic devices treating facial areas, eye protection is needed to avoid light damage or irritation to a patient's eyes. Prior known devices have typically used separable patches which must rest on the eye area to block the therapeutic light from communication to the eye system itself. There is a need for a better way that is readily adaptable to communicate therapeutic light to areas near the eyes, particularly with regard to anti-aging treatments, and still protect the patient.

It is desired to provide alternative means of using the benefits of the light therapy in a manner to maximize therapeutic efficiencies in exposure while maintaining ease and convenience of use. For this reason, a variety of light weight, flexible and adjustable embodiments are disclosed within this disclosure incorporating a variety of energy varying applications responsive to user conditions or needs.

SUMMARY

The present embodiments comprise phototherapy systems and devices comprising a therapeutic lamp platform for radiant lamps such as LEDs are disposed in an assembly comprising a first wall to which the lamps are affixed thereto and a second wall, closer to the patient, spaced from the first wall wherein the lamps are recessed relative thereto. The second wall comprises a reflective surface facing towards a patient and a plurality of light apertures substantially aligned with the LEDs on the first wall for communicating lamp radiation from the lamps to a user. The lamps and associated circuitry are disposed between the first and second wall so that the reflective surface is relatively smooth and seamless towards the patient. The number of lamps are minimized, as is the circuitry therefor, and other assembly materials are purposefully selected for a relatively light weight assembly resulting in enhanced user comfort during therapy sessions. The walls have a malleable rigidity for flexible adjustability relative to the user. More particularly, the walls have a concave configuration relative to the face of the user which is adjustable relative to a rest position to be expandable relative to a size of the head of the user for a close fitting and secure engagement to the user during use. The device is mounted to the user with a frame comprising an eyeglass frame or goggles including lenses for shielding the user's eyes from lamp radiation. The adjustability of the embodiments is further enhanced by the walls being pivotable relative to the support frame and where the frames may include telescopic temple arms for selective adjustability relative to the head size of the user. The device is thus supported on the patient as a wearable hands-free mask or the like. A power source communicates energy to the lamps and comprises a remote battery pack and may also include a control processor for counting the number of uses by the device for the user and for indicating a need for device replacement after a predetermined number of uses.

The present embodiments comprise an adjustable/flexible platform for providing a light-based therapy that is adaptable to the user's receptive surfaces, whether based on size or condition, wherein the light therapy can be applied without limitation of the kind of light and without limitation of the ultimate purpose of the therapy, i.e., beauty, health, and/or wound healing. Such sources can vary in the form of the radiant energy delivery. Pulsed light (IPL), focused light (lasers) and other methods of manipulating light energy are encompassed within the present embodiments. Other methods of light emission may comprise continuous, pulsed, focused, diffuse, multi wavelength, single wavelength, visible and/or non-visible light wavelengths.

A present embodiment describes forms such as a shaped/fitted mask, goggles, eye mask, shroud or hood, and facial mask (collectively referred to as "mask") with LED light emitted from LED bulbs or LED strips that are capable of being adjusted to accommodate the variances in face size or areas intended for therapeutic attention. Control systems are included to vary light intensity, frequency or direction.

The platform can be secured to the head by multiple means: eyeglass frames, straps, drawstring, harness, Velcro®, turn dial or snap and buttons. As the mask is secured it can be adjusted upward, for chin to forehead coverage. It can also be adjusted outward, for side-to-side coverage. In addition, once the platform has been bent/slid to cover the face area, the distance of the platform from the skin can be adjusted for achieving a desired light intensity relative to a user's skin surface. Thus, the light therapy can be maximized in up to three physical dimensions.

The subject adjustability may be implemented through "smart" processing and sensor systems for enhanced flexibility/adjustability in the form of adjustable energy output, adjustable wavelengths, priority zones, timers, and the like. The sensors of the sensor systems will enable the subject embodiments to have the ability to evaluate the skin of the face and body of a patient with sensors for color, wrinkles, age spots, acne, lesion density, and the like, and plan a smart treatment, utilizing more or less energy on the priority zones. The subject embodiments can be smart from the standpoint of skin type, age, overall severity of problems and have the ability to customize the treatment accordingly.

In yet another embodiment, the phototherapy system device includes an aligned eye slot disposed for user to see through the device. Also included is a radiation absorbing layer interposed between the lamps and the outer wall.

In yet another embodiment, the lamps are embedded in a flexible sheet of formable material and are integrally molded as strips within a material sheet.

In addition, control systems can measure or count device usage and communicate historical usage, and indicate a time for replacement.

The present disclosure thus describes a fully flexible and adjustable LED device which provides improved usability and light dispersion.

According to another exemplary embodiment of this disclosure, provided is a therapeutic lamp platform controller comprising a power source; a control circuit operatively connected to the power source, the control circuit including one or more outputs to drive one or more radiant lamps associated with a therapeutic lamp platform; a user display; and a user control switch, the control circuit configured to control one of a plurality of therapeutic lamp platforms, each lamp platform including a plurality of radiant lamps including a unique mixed combination of different wavelength radiant energy disposed to communicate the radiant energy to a user treatment area.

According to still another exemplary embodiment of this disclosure, provided is a therapeutic lamp platform controller comprising a power source; a control circuit operatively connected to the power source, the control circuit including one or more outputs to drive one or more radiant lamps associated with the phototherapy device; a user display; and a user control switch, the control circuit configured to control a plurality of therapeutic lamp platforms, each therapeutic lamp platform including a plurality of radiant lamps including one or more wavelengths of radiant energy disposed to communicate the radiant energy to a user treatment area.

According to yet another exemplary embodiment of this disclosure, provided is a therapeutic lamp platform controller comprising a power source; a control circuit operatively connected to the power source, the control circuit including one or more outputs to drive a plurality of radiant lamps associated with a therapeutic lamp platform, the plurality of radiant lamps including a mixed combination of different wavelength radiant energy and the plurality of radiant lamps disposed to communicate the radiant energy to a user treatment area; a user display operatively connected to the control circuit; and a user control switch operatively connected to the control circuit, wherein the control circuit is configured to control a dosage amount of radiant energy communicated to the user treatment area.

According to another exemplary embodiment of this disclosure, provided is a therapeutic lamp platform controller comprising a power source; a control circuit operatively connected to the power source, the control circuit including one or more outputs to drive a plurality of radiant lamps associated with a therapeutic lamp platform, the plurality of radiant lamps including a mixed combination of different wavelength radiant energy and the plurality of radiant lamps disposed to communicate the radiant energy to a user treatment area; a user display operatively connected to the control circuit; and, a user control switch operatively connected to the control circuit, wherein the control circuit is configured to limit a number of available doses from the controller to a predetermined number.

According to yet another exemplary embodiment of this disclosure, provided is a therapeutic lamp platform controller comprising a power source; a control circuit operatively connected to the power source, the control circuit including one or more outputs to drive a plurality of radiant lamps associated with a therapeutic lamp platform, the plurality of radiant lamps including a mixed combination of different wavelength radiant energy and the plurality of radiant lamps disposed to communicate the radiant energy to a user treatment area; a user display operatively connected to the control circuit; and a user control switch operatively connected to the control circuit, wherein the control circuit is configured to display on the user display the time remaining for an active dosage treatment session.

According to still another exemplary embodiment of this disclosure, provided is a therapeutic lamp platform controller comprising a power source; a control circuit operatively connected to the power source, the control circuit including one or more outputs to simultaneously drive a plurality of therapeutic lamp platforms; a user display; and a user control switch, the control circuit configured to simultaneously control the plurality of therapeutic lamp platforms, each therapeutic lamp platform including a plurality of radiant lamps disposed to communicate radiant energy to a user treatment area.

According to another exemplary embodiment of this disclosure, provided is a therapeutic lamp platform controller comprising a down source; a control circuit operatively connected to the power source, the control circuit including one or more outputs to simultaneously drive a plurality of therapeutic lamp platforms; a user display; and a user control switch, the control circuit configured to simultaneously control the plurality of therapeutic lamp platform, each therapeutic lamp platform including a plurality of radiant lamps including a mixed combination of different wavelength radiant energy and the radian lamps disposed to communicate the radiant energy to a user treatment area.

According to yet another exemplary embodiment of this disclosure, provided is a method of charging a power source operatively associated with a therapeutic lamp platform, the therapeutic lamp platform including a plurality of radiant lamps disposed to communicate radiant energy to a user treatment area, a rechargeable power source operatively associated with powering the plurality of radiant lamps, a control circuit operatively associated with controlling a dosage of radiant energy provided to the user treatment area, and a charging port operatively associated with charging the rechargeable power source from an external power source, the method comprising connecting a power port of a computing device to the therapeutic lamp platform charging port using an electrical cable; launching a charging software application on the computing device, the charging software application configuring the computing device to utilize a port operatively associated with the computing device to charge an external device; the computing device charging the therapeutic lamp platform rechargeable power source until the rechargeable power source reaches a substantially full charge; and disconnecting the electrical cable from the therapeutic lamp platform.

According to another exemplary embodiment of this disclosure, provided is a method of charging a power source operatively associated with a therapeutic lamp platform, the therapeutic lamp platform including a plurality of radiant lamps disposed to communicate radiant energy to a user treatment area, a rechargeable power source operatively associated with powering the plurality of radiant lamps, a control circuit operatively associated with controlling a dosage of radiant energy provided to the user treatment area, and a charging port operatively associated with charging the rechargeable power source from an external power source, the method comprising connecting a power port of a computing device to the therapeutic lamp platform charging port using an electrical cable; the computing device charging the therapeutic lamp platform rechargeable power source until the rechargeable power source reaches a substantially full charge; and disconnecting the electrical cable from the therapeutic lamp platform.

According to still another exemplary embodiment of this disclosure, provided is a phototherapy device comprising a wearable therapeutic lamp platform including a plurality of radiant lamps and a reflective wall disposed to communicate radiant energy to a user treatment area; a frame for supporting the platform on a user; a control circuit operatively mounted to one of the wearable therapeutic lamp platform and the frame; a rechargeable power source operatively mounted to one of the wearable therapeutic lamp platform and the frame; and a charging port operatively mounted to one of the wearable therapeutic lamp platform and the frame, the charging port operatively associated with charging the rechargeable power source, wherein the phototherapy device is configured to be chargeable by a mobile communication device and an electrical cable operatively connected to the phototherapy device charging port and a mobile communication device port configured to charge an external device.

According to another exemplary embodiment of this disclosure, provided is a phototherapy device comprising a wearable therapeutic lamp platform including a plurality of radiant lamps including a mixed combination of different wavelength radiant energy and a reflective wall with a plurality of radiant energy communication areas aligned with the radiant lamps and disposed to communicate the radiant energy to a user treatment area, and wherein the reflective wall is further formed to disperse the radiant energy over the user treatment area; a frame for supporting the platform on a user; a control circuit operatively mounted to one of the wearable therapeutic lamp platform and the frame; a rechargeable power source operatively mounted to one of the wearable therapeutic lamp platform and the frame; and a charging port operatively mounted to one of the wearable therapeutic lamp platform and the frame, the charging port operatively associated with charging the rechargeable power source, wherein the phototherapy device is configured to be chargeable by a mobile communication device and an electrical cable operatively connected to the phototherapy device charging port and a mobile communication device port configured to charge an external device.

According to still another exemplary embodiment of this disclosure, provided is a phototherapy device comprising a wearable therapeutic lamp platform including a plurality of radiant lamps disposed to communicate radiant energy to a user treatment area; a power source; a controller operatively associated with the therapeutic lamp platform and the power source configured to limit a number of available doses of radiant energy provided to a user, and the controller configured to communicate with an ecommerce platform to obtain an additional number of available doses.

According to another exemplary embodiment of this disclosure, provided is a portable computing device operatively associated with an operatively connected wearable therapeutic lamp platform, the portable computing device comprising one or more processors and operatively associated memory storing instructions, the one or more processors configured to execute the stored instructions to perform one or more of a) executing an ecommerce application for a user to purchase a number of therapy session dosages to be provided by the therapeutic lamp platform; b) monitoring a number of available therapy session dosages available on the therapeutic lamp platform; c) perform diagnostics on the therapeutic lamp platform; d) monitoring the remaining time for an active therapy session dosage being provided by the therapeutic lamp platform; and e) controlling an execution of a therapy session dosage, wherein the portable computing device initiates the start of the therapy session dosage.

According to another exemplary embodiment of this disclosure, provided is a phototherapy system comprising a phototherapy device including a plurality of radiant lamps disposed to communicate radiant energy to a user treatment area, a rechargeable power source, and a controller operatively associated with controlling a delivery of the radiant energy to the user treatment area, wherein the plurality of radiant lamps, the rechargeable power source and controller are housed by a mask shaped therapeutic lamp platform wherein the phototherapy device is configured to inductively charge the rechargeable battery; and an inductive charger configured to charge the phototherapy device rechargeable battery.

According to another exemplary embodiment of this disclosure, provided is a phototherapy device comprising a wearable therapeutic lamp platform including a plurality of radiant lamps including a mixed combination of different wavelength radiant energy, and a reflective wall with a plurality of radiant energy communication areas aligned with the radiant lamps and disposed to communicate the radiant energy to a user treatment area and a frame for supporting the platform on a user; wherein the reflective wall is further formed to disperse the radiant energy over the treatment area, and the lamp platform includes an inductively chargeable power system.

According to yet another exemplary embodiment of this disclosure, provided is a phototherapy device comprising a therapeutic lamp platform including a mask including a plurality of radiant lamps having a mixed combination of different wavelength radiant energy and disposed to communicate the radiant energy to a user treatment area, the plurality of radiant lamps further disposed to provide radiant therapy to provide a first treatment session including a first set of wavelength radiant energy, and a second treatment session including a second set of wavelength radiant energy including at least one wavelength radiant energy not provided in the first treatment session; and a frame for supporting the mask on a user.

According to another exemplary embodiment of this disclosure, provided is a phototherapy device comprising a wearable therapeutic lamp platform including a plurality of radiant lamps including a mixed combination of different wavelength energy and a reflective wall with a plurality of radiant energy apertures aligned with the radiant lamps and disposed to communicate the radiant lamps and disposed to communicate the radiant energy to a user treatment area, and wherein the reflective wall is further formed to disperse the radiant energy over the treatment area; and a controller operatively associated operating the radiant lamps to provide a first treatment session including a first set of wavelength radiant energy, and a second treatment session including a second set of wavelength radiant energy including at least one wavelength radiant energy not provided in the first treatment session.

According to still another exemplary embodiment of this disclosure, provided is a phototherapy device comprising a wearable therapeutic lamp platform including a plurality of radiant lamps and a reflective wall disposed to communicate radiant energy from the plurality of radiant lamps to a user treatment area including a scalp of the user, and the wearable lamp platform including a headband operatively associated with supporting the plurality of radiant lamps and reflective wall above the user's scalp.

According to yet another exemplary embodiment of this disclosure, provided is a phototherapy device comprising a wearable therapeutic lamp platform including a plurality of radiant lamps disposed to communicate radiant energy from the plurality of radiant lamps to a user treatment area including a scalp of the user, and the wearable lamp platform including a helmet operatively associated with supporting the plurality of radiant lamps five above the user's scalp.

BRIEF DESCRIPTION OF THE DRAWINGS

FIGS. 20A and 20B is a schematic of a first therapeutic lamp platform controller as shown in FIG. 5, according to an exemplary embodiment of this disclosure;

FIG. 21A is a perspective view of another second therapeutic lamp platform controller according to an exemplary embodiment of this disclosure;

FIG. 21B is an exploded view of another second therapeutic lamp platform controller according to an exemplary embodiment of this disclosure;

FIGS. 33A and 33B show the docking of an inductively charged therapeutic lamp platform on an inductive charger according to an exemplary embodiment of this disclosure;

FIGS. 34A, 34B and 34C further illustrate the docking of an inductively chargeable therapeutic lamp platform according to an exemplary embodiment of this disclosure;

FIGS. 39A and 39B illustrate a therapeutic lamp platform configured to stimulate hair growth according to an exemplary embodiment of this disclosure;

FIGS. 41A and 41B are detail views of LED/Brush Bristle configurations for a therapeutic lamp platform configured to stimulate hair growth;

FIGS. 42A and 42B are detail views of radiant energy scalp coverage associated with an exemplary embodiment of a therapeutic lamp platform configured to stimulate hair including LEDs without an associated light pipe, and with an associated light pipe, respectively;

FIGS. 43A and 43B are further detail views of radiant energy scalp coverage associated with a therapeutic lamp platform without a light pipe and with a light pipe, respectively, as shown in FIGS. 42A and 42B;

FIGS. 46A and 46B illustrate another therapeutic lamp platform configured to stimulate hair growth including a helmet according to an exemplary embodiment of this disclosure.

DETAILED DESCRIPTION

Figure 1:
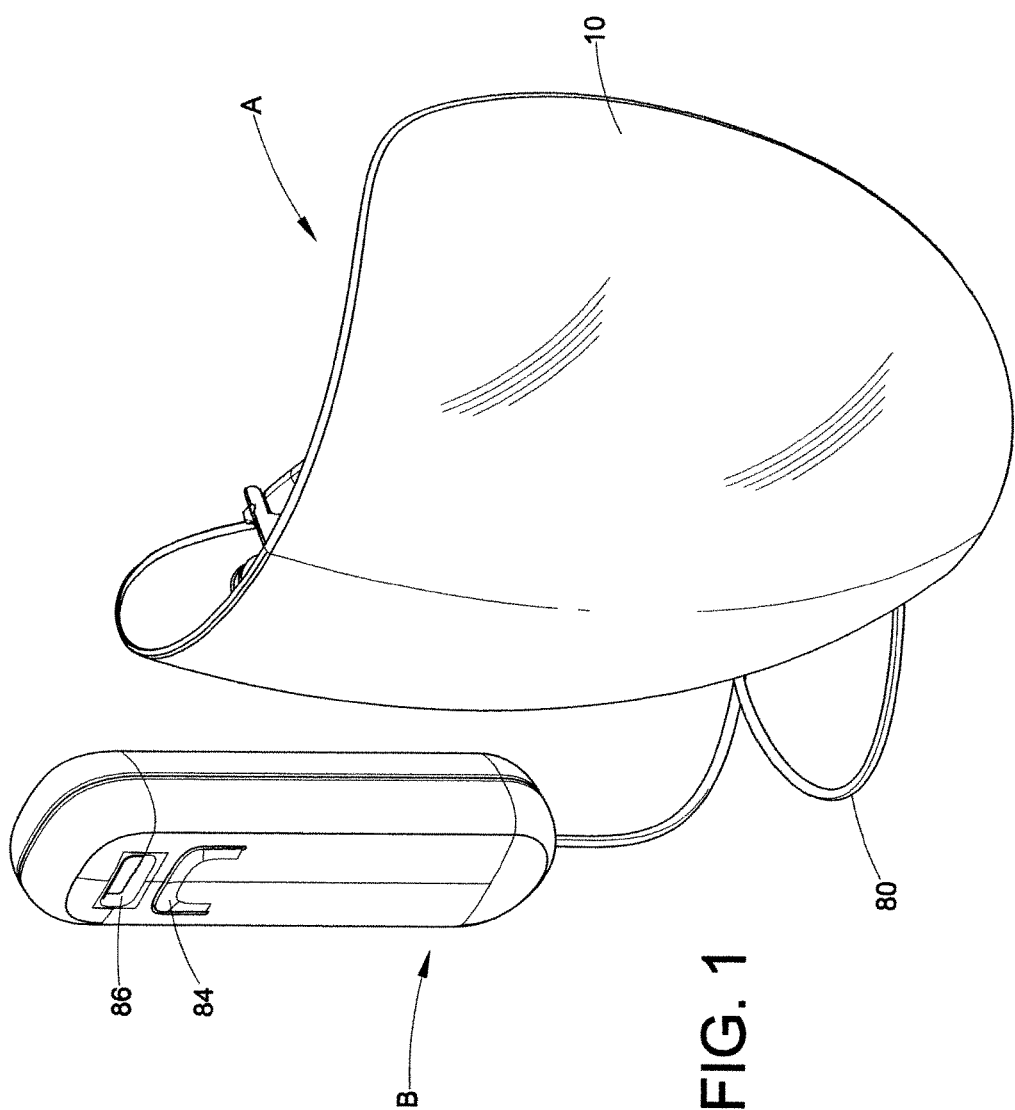
FIG. 1 is a perspective view of one embodiment of a therapeutic lamp platform comprising a wearable mask.

The subject embodiments relate to a phototherapy system including methods and devices, preferably comprising a wearable hands-free device with a remote battery pack for powering therapeutic lamps in the device. The subject devices display numerous benefits including a light platform wherein the platform and the lamps therein are properly positionable relative to a user during use with no human touch. That is, structural componentry of the device not only supports the lamp platform on the user, but functions as a guide for the appropriate disposition of the lamps relative to the treatment areas of the user. The structural assembly of the device precludes sharp or hot surfaces from being engageable by a user as the lamps are recessed relative to an inner reflective surface closest to and facing the patient treatment surface. Circuit componentry to communicate power to the lamps is also encased within the wall structure. Therapeutic light, shining through wall apertures, is communicated to the user while the lamps and the circuitry are effectively encased within the spaced wall structure. A smooth seamless surface is thus presented to the user that is properly spaced for the desired therapeutic treatments, yet provides improved ventilation so that an aesthetic and appealing device surface is presented to the user that minimizes user discomfort. Other benefits relate to the adjustability of the device in the form of a flexible mask which forms upon user receipt to match a treatment surface, e.g., a head size, of the user. Smart componentry not only measures device usage, but may also calculate lamp degradations so that a time for proper replacement can be communicated to a user. The overall assembly is purposefully constructed of relatively light weight and minimized componentry for ease of user use and comfort.

More particularly, and with reference to FIGS. 1-4, subject embodiments preferably comprise a lamp platform A and a remote battery pack B. The platform A is comprised of a wall structure 10 encasing the plurality of therapeutic lamps such as red and blue LEDs 12 and circuitry 14 for communicating power to the lamps via cable 80 and connector 83 from the battery pack B. Other radiant energy forms could also include fluorescents, lasers or infrareds. The wall structure 10 is mounted on a support frame 20 connected via snap-out pivotal connections 22 which allows the wall structure to adjust position via a slight pivot relative to the frame 20. The frame 20 also includes protective lenses 24 and a nose bridge 26. The temple arms 28 may be fixed or telescopic and hinge relative to the frame 20 so that the platform A can be mounted on a user in a hands-free support manner via resting on the nose with the nose bridge 26 and the ears with temple arms 28.

Figure 3:
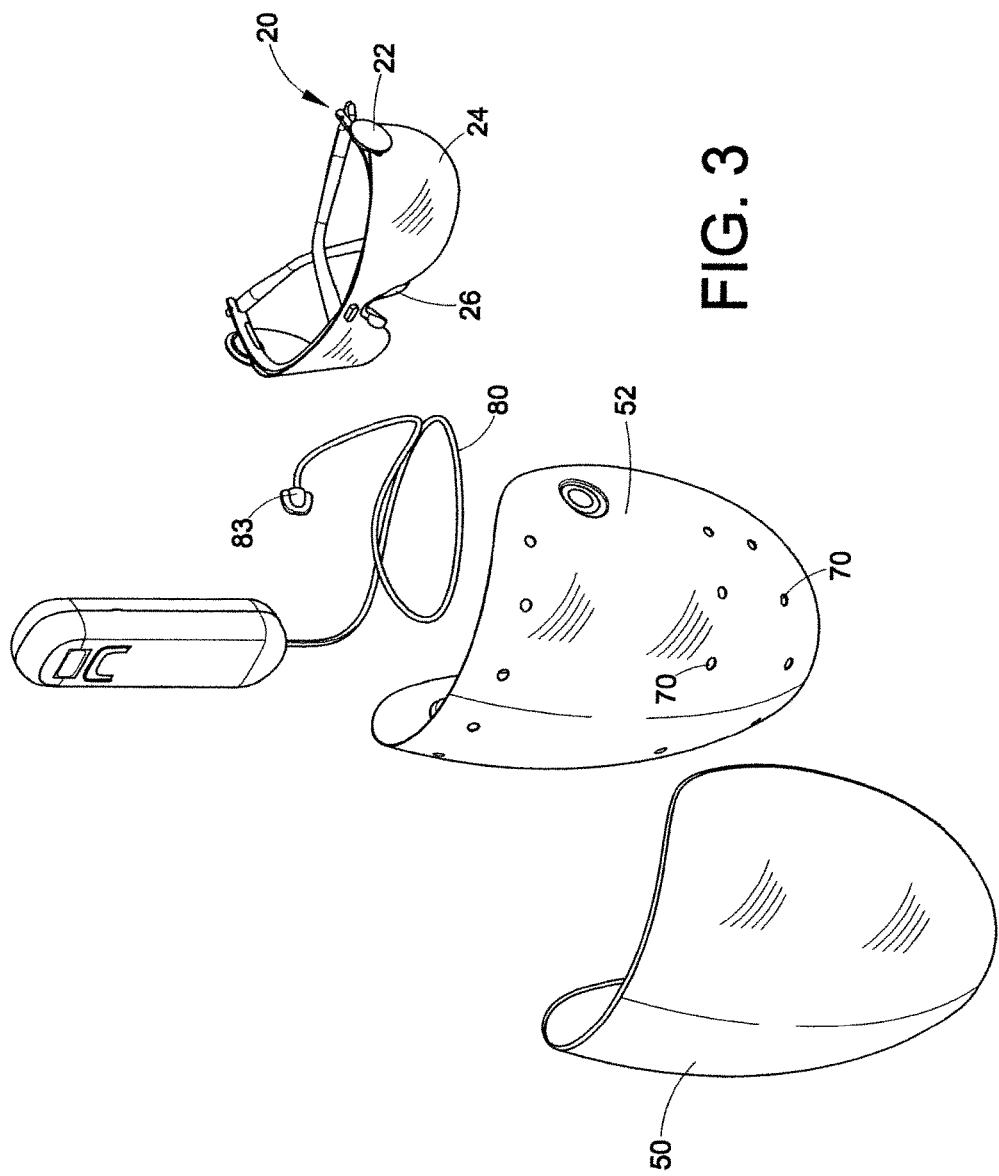
FIG. 3 is an exploded perspective view of FIG. 1.
Figure 4:
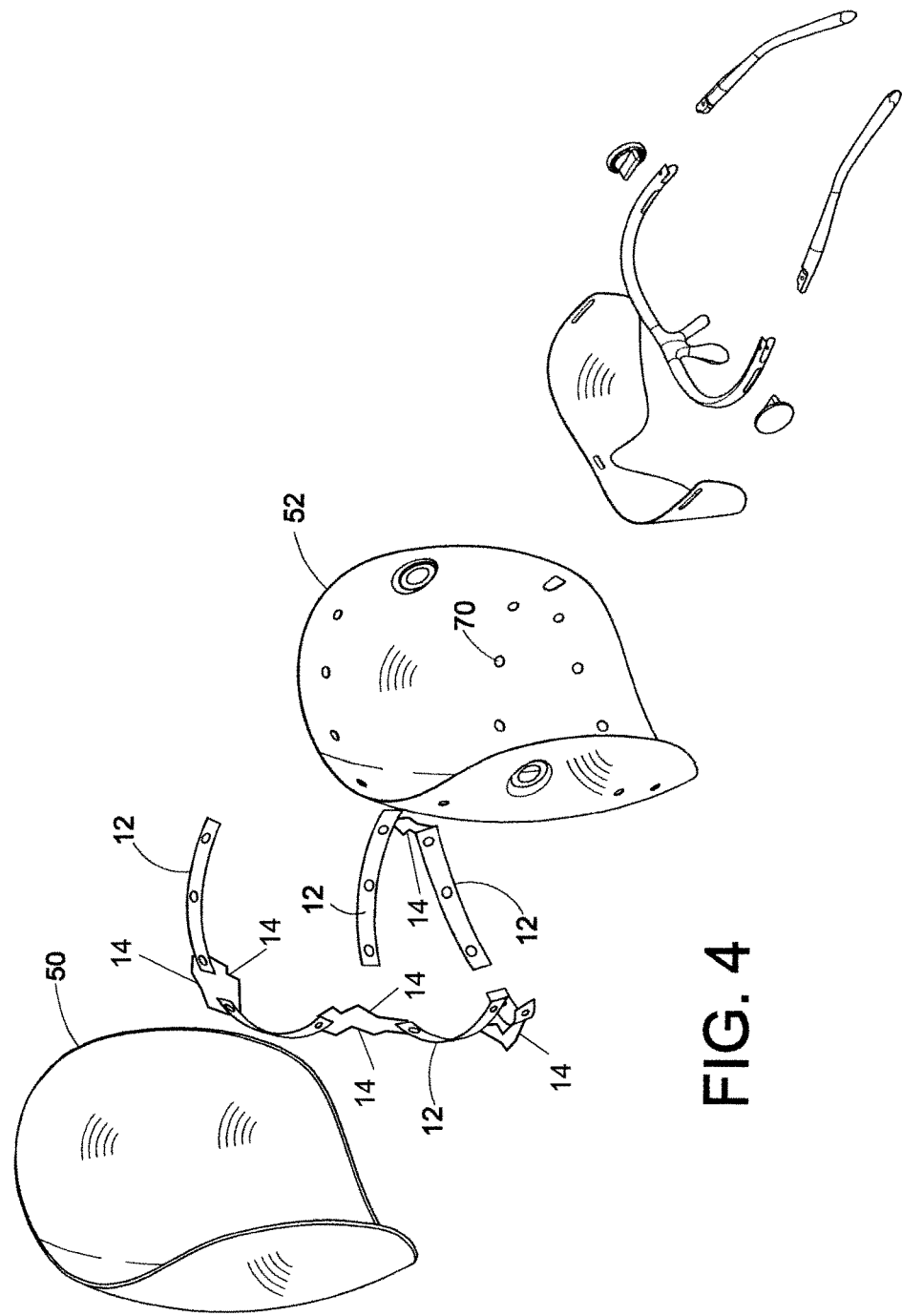
FIG. 4 is an exploded perspective view of FIG. 2.

With reference to FIGS. 3, 4, 6, 7 and 8 it can be seen that the wall structure 10 is comprised of an outer wall 50 and an inner wall 52. The outer wall is disposed furthest away from the treatment surface of the user, while the inner wall 52 is disposed closer thereto. The walls have a concave configuration in both horizontal and vertical directions and are constructed of a plastic material having a malleable rigidity so that the structure 10 can be bent and deflected slightly during use. The concavity comprises a multi-dimensional parabolic curvature for catching and reflecting the radiation back to the treatment areas. It is intended that the concavity is slightly smaller than the head of the user so that the mask has to be bent out when applied thereby providing a close but comfortable tightness on the user which will keep the assembly A in a desired position during use. The concavity also positions the therapeutic lamps or LEDs 12 in desired positions relative to the user. The spacing 54 between walls 50 and 52 receives the lamps 12 and circuitry 14 so that the lamps and circuitry are interposed between the walls for enhanced safety and convenience purposes. It can be seen that the spacing is diminished from the middle of the device towards the end portions 58, 60; however, the entire end perimeter of the assembly 10 is sealed as the walls come together. Such a mating seal is typically effected through a sonic weld arrangement. Alternatively, local sealing points (not shown) can be employed to assemble the walls together with spaced intermediate seals. Thus, the inner and outer masks have different radii of concavity but present an integral structure as far as the user is concerned. The outer wall 50 primarily functions as a support for the lamps 12 and circuitry 14. With reference to FIG. 4 it can be seen that the lamps are disposed on the wall 50 in a predetermined manner for radiating treatment areas most susceptible for the phototherapeutic treatment. A minimum number of lamps 12 are intended but still enough to provide effective therapy. Alternatively, the lamps could be fixed to the inner wall 52. Regardless of which wall supports the lamps, the lamps need to be properly aligned with apertures 70 to desired treatment areas.

Rather than placing a plurality of LEDs randomly, the subject LEDs are specifically minimized in number and disposed relative to the treatment areas and wall parabolic reflectivity to effect the desired therapy. More particularly, it can be seen that the individual lamps 12, and associated inner wall apertures 70, are disposed to treat the most common areas benefiting from the therapy. The present embodiments illustrate a placement pattern useful for skin acne treatment. Other placement patterns are certainly intended to fall within the scope of the disclosed embodiments. Here three LED strips are seen and would typically comprise two blue strips on the top and bottom of a middle red strip, as these frequencies are most useful for acne treatment. The subject invention may include only blue, only red, or any other mixed combination of LED or other radiant energy form pattern. The illustrated pattern would thus have intensified therapeutic effect on the jaw line, chin, cheek and forehead, but not the eyelids. Light sources can include LEDs, fluorescents, lasers or infrareds as an example. Such sources can vary in the form of the radiant energy delivery. Pulsed light (IPL), focused light (lasers) and other methods of manipulating light energy are encompassed within the present embodiments. Other methods of light emission may comprise continuous, pulsed, focused, diffuse, multi wavelength, single wavelength, visible and/or non-visible light wavelengths.

The inner wall 52 is comprised of a smooth seamless reflective surface facing the treatment area and includes a plurality of apertures 70 matingly aligned relative to the lamps so that the lamps can radiate the therapeutic light 57 through the apertures 70. Accordingly, the LEDs 12 are recessed relative to the inner wall 52 to preclude Contact with the treatment surface and to make it very difficult for the lamps themselves to be in any way contacted by the user. Such an assembly results in a controlled communication of radiating therapy in a manner to impart a predetermined cone of therapeutic light on to a treatment area. The apertures are disposed relative to desired treatment areas and wall parabolic configuration for even light distributions across the treatment area. A combination of such a controlled cone of light, predetermined disposition of the lamps themselves on the platform, an inner reflective surface on the inner wall 52, and a controlled positioning of the assembly relative to the treatment area via a platform position relative to contact areas of the nose and the ears, presents an assembly which presents a highly predictable distributive pattern of the light (predetermined cones of light per light source), thereby minimizing the number of lamps 12 that need to be included for effective treatment.

Figure 2:
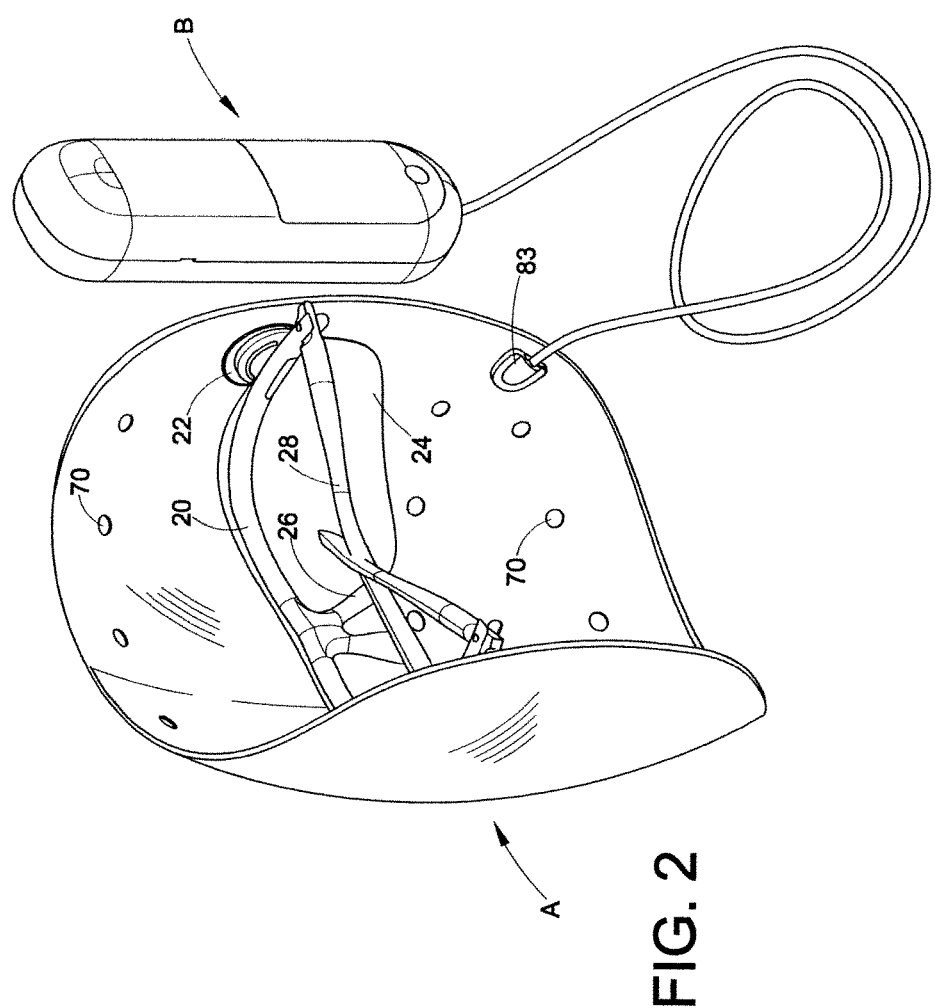
FIG. 2 is another perspective view of the device of FIG. 1.

With reference to FIGS. 2, 3 and 4, one embodiment comprises a support frame essentially comprising eyeglass frames as the associated support structure for the platform 10. Interchangeable lenses 24 can be used to adjust the level of protection afforded by the lenses or their relative shape. Although not shown therein, telescopic temple arms 28 may telescope for better sizing relative to the head size of the user. Formable ear latches can also be included as part of the temple arms. Alternatively, the arms could include a head strap. The pivotable joints 22 allow the wall structure to pivot relative to the frames so that a user may adjust light intensity relative to a treatment area by moving the layers closer or farther away. As noted above, the platform 10 is flexible with a concave parabolic bias, but still has a malleable rigidity. When the frame 10 is received on the user, it is disposed to expand the platform parabolic bias to form a match to the size of the user. Eyeglass frame reference contact points of the user may comprise the nasion area, the nose bridge and the ears of the user. Alternatively, the support frame can comprise a goggle and head strap configuration relying on the nasion area.

Battery pack B (FIG. 5) holds the supply batteries 81 and processing controller 82 that is in electrical communication with the lamps through wire 80. The wiring between connectors 83 and LED strips 12 is not shown to avoid drawing clutter but is contained between walls 50, 52. The battery pack will include an on-off switch 84 and a user interface 86. The processing controller 82 may include a variety of control systems indicating device usage to the user. Such a system would be a counter. The user interface may comprise a display for a variety of useful information from the controller control systems to the user, such as a count of the number of times of usage and communication that the device has been used enough times such that the LEDs themselves have degraded and a replacement is recommended for the therapy.

Figure 11:
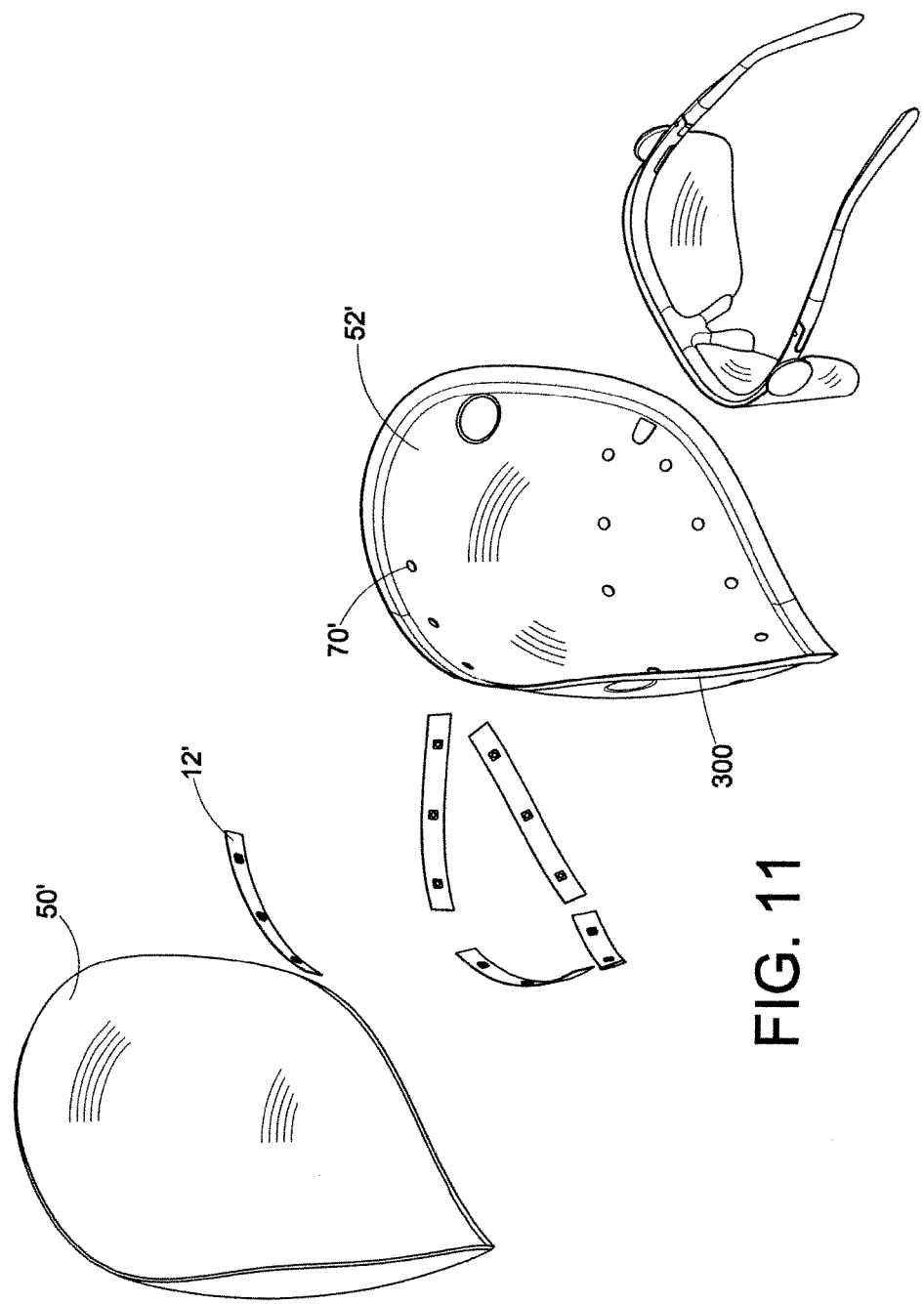
FIG. 11 is an exploded view of an alternative embodiment wherein the mask walls are spaced by a flange.
Figure 12:
FIG. 12 is an embodiment of a packaging assembly containing the device of FIG. 1.
Figure 13:
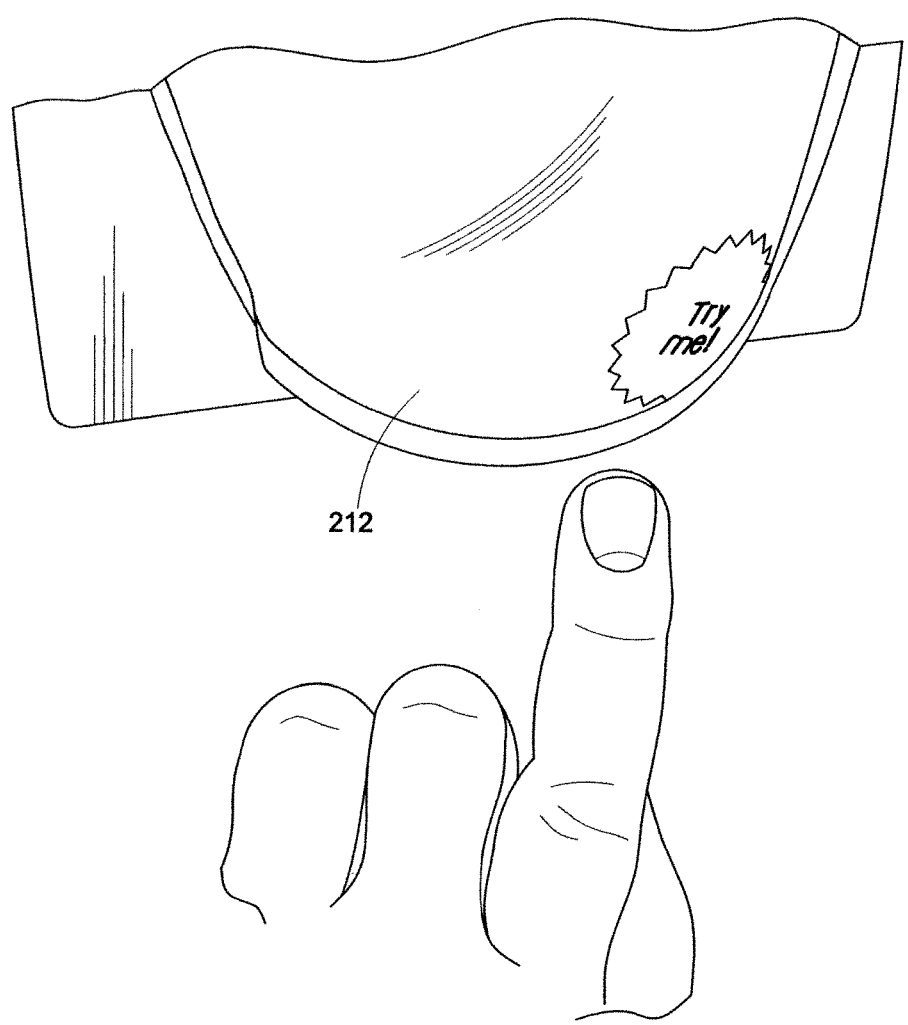
FIG. 13 illustrates a try-me feature of the packaging of FIG. 11 wherein a user can view a sample operation of the device.

"Try-me packaging", FIGS. 11 and 12, presents a demonstrative use opportunity to a potential user while still packaged. The subject embodiments further include a packaging assembly 210 containing the device wherein a switch S1 (not shown) for operating the lamp assembly has a multi-position effect functionality including an on-mode, an off-mode and a try-me mode. The try-me mode is accessible while the lamp assembly is contained in packaging for displaying lamp operation to a user. The packaging includes a clear or translucent cover 212 over the device A. A try-me time-out circuit is included for limiting the try-me display time of lamp operation, such as, for example two seconds. Lamp on-time as measured by the counter is segregable from the try-me mode so that try-me usage will not affect dosage count of the device for actual therapy. It is assumed try-me usage time will be negligible relative to a dosage use time.

The subject devices include multiple benefits to the user in a wearable hands-free device with a remote battery pack. The device is properly positionable in a relatively automatic way with minimal human touch by exploiting user reference contact points, and is particularly hand-free during use. No sharp or hot surfaces are engageable by the user. A smooth seamless surface faces the user and is properly spaced from the treatment area to provide enhanced ventilation and minimal discomfort during treatment.

Figure 14:
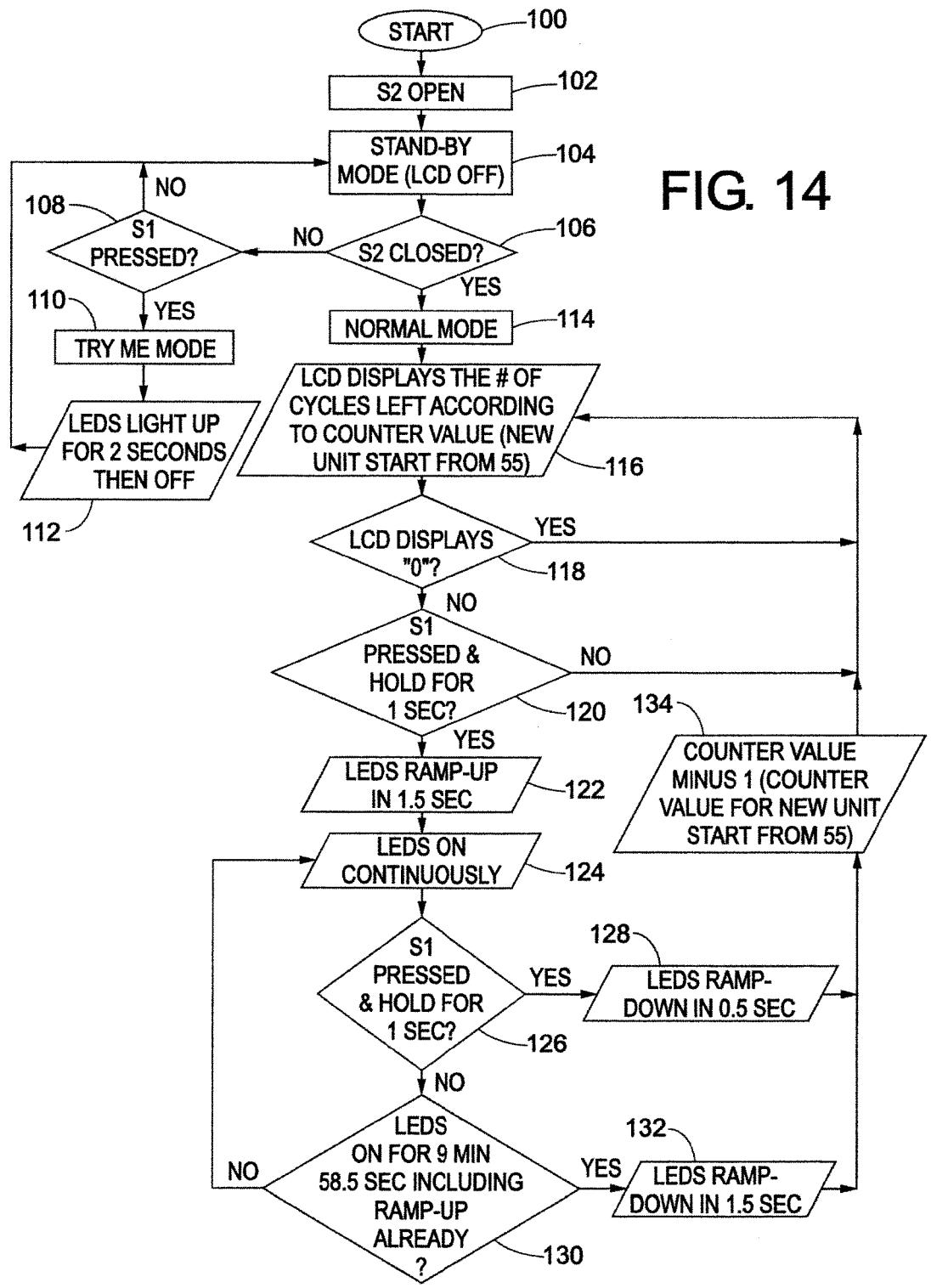
FIG. 14 is a flowchart of operational device control.

With particular reference to FIG. 14, a flowchart illustrating an operational embodiment of a device control is illustrated. The device visioned as operational by FIG. 10 includes two switches, S1, S2, at least one of which are required to be closed to communicate energy from an energy source to the therapeutic lamps. S2 is a safety switch which is open when the device is in sales packaging so that only the "try-me" mode is enabled when S2 is open. After removal from the packaging, S2 can be closed and the device can be operated in a normal mode. Accordingly, after start 100, and in a situation when S2 is opened 102, such as when the device is still within the packaging, the system will remain in a stand-by mode wherein the GUI interface (such as a LCD) is off 104. If S2 remains closed 106 but S1 is pressed 108 (e.g. FIG. 12), then the device can enter the "try-me" mode 110 wherein the LEDs will light up for two seconds, then turn off 112. Such a "try-me" mode operational demonstration to a user while the device is in a packaging communicates to the user actual operation and can assist in a decision to purchase, or have a better understanding of how the device operates. If the device is removed from the packaging, and S2 is closed, the device will enter normal mode 114 wherein the GUI will include a LCD displaying the number of cycles left according to a counter value 116. Note that counter value 134 is not affected by any try-me sampling operation.

In one embodiment, the unit will count down from 55 to 1, as 55 uses is deemed to be enough to diminish enough LED efficiency from the peak operational mode of LEDs when they are used as the therapeutic radiant lamps. Accordingly, upon a user picking up the device, they will immediately know how many cycles are left for acceptable and recommended operation of the device from 55 more uses all the way down to 0 118. If the display shows a count greater than 0, and the user is interested in a therapy session, the user will turn the unit on by pressing S1 120 wherein the LEDs will ramp up to radiant operation 122 in approximately 1.5 seconds and then will radiate continuously 124 until either the user desires to turn off the unit by again pressing S1 126 so that the LEDs can ramp down 128 or until a therapy session has timed out 130 such as for remaining radiant for approximately ten minutes. After completing an appropriate run time of a therapy session, the LEDs will ramp down 132 and the GUI display to the user will subtract 1 from the counter value 134.

Figure 9:
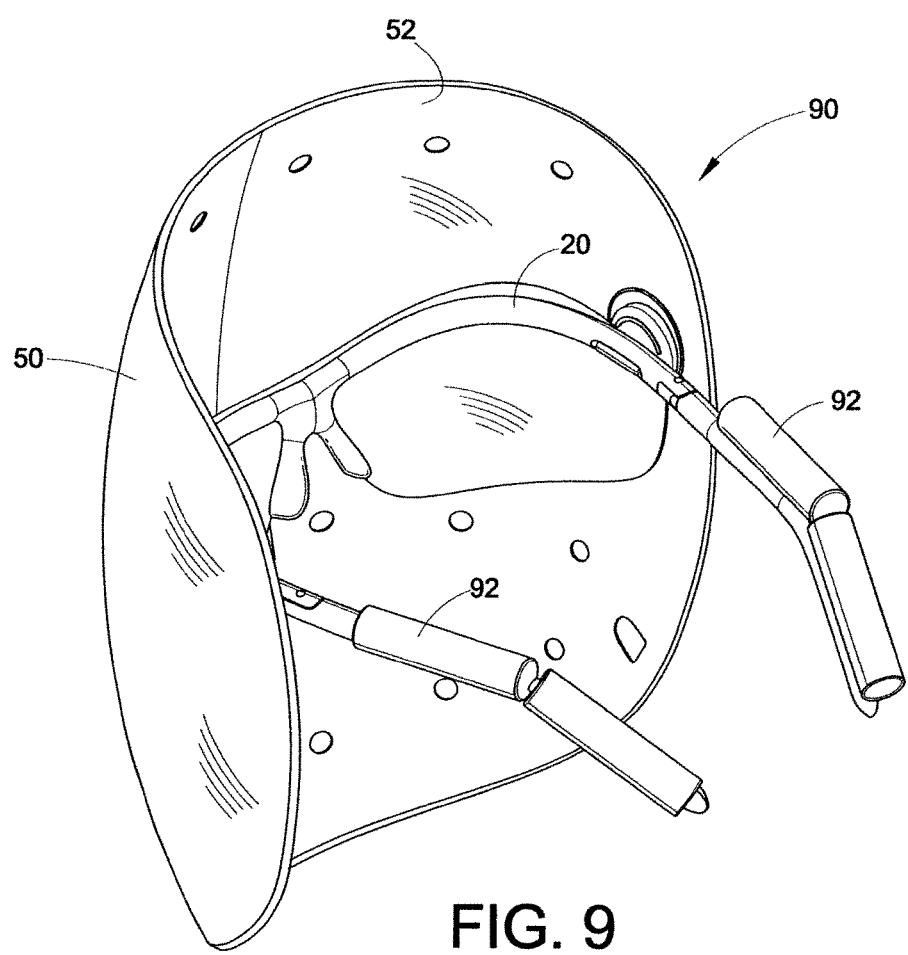
FIG. 9 is a perspective view of an alternative embodiment wherein the power supply and control circuitry are integrally formed with the mask assembly.
Figure 10:
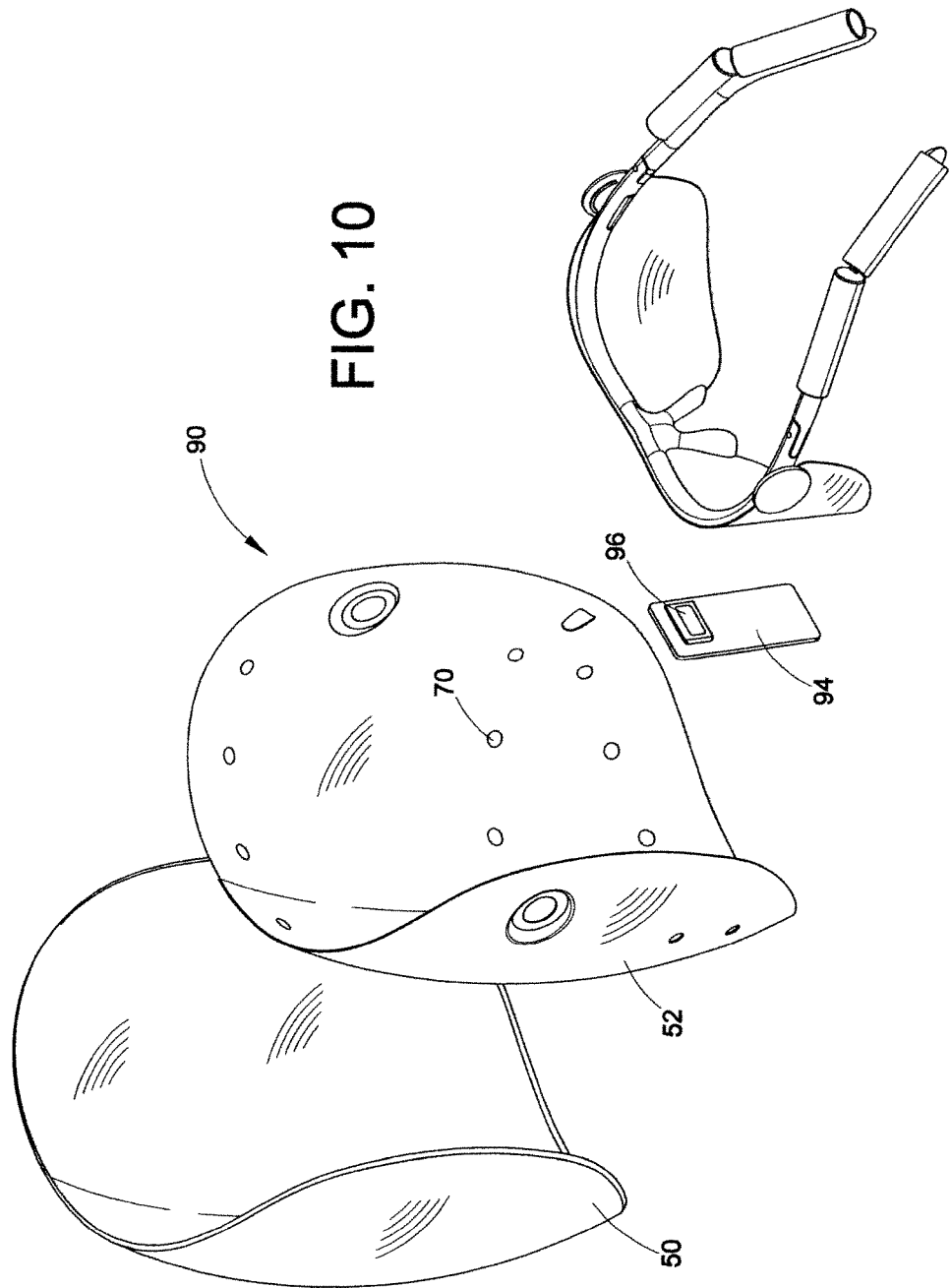
FIG. 10 is an exploded view of the device of FIG. 9.

With reference to FIGS. 9 and 10, an alternative embodiment is shown wherein a controller B is eliminated and the energy source and processing control are all integrally assembled in the device 90. In this case, the platform 20 and walls 50, 52 remain substantially the same as per the FIG. 1 device. However, the energy source such as batteries 92 are disposed as part of the eyeglass temple arms wherein wires provide energy from the batteries 92 to the LEDs through the hinge points of the frame 20 and into the spacing 54 for ultimate connection to the LEDs themselves. The controller 94 including LCD display 96 is also housed behind the reflective wall 52 relative to the user, which wall 52 can include a relatively small cutout (not shown) for the screen 96.

The embodiment of FIGS. 9 and 10 is thus even more compact than the embodiment of FIG. 1, and more hands-free therefrom, as it eliminates the need to somehow manage the controller B during operation.

FIG. 11 shows yet another alternative embodiment wherein the outer wall 50' and the inner wall 52' are not spaced by being configured with different curvatures. Rather, the walls 50', 52' have the same curvature, but the inner wall 52 has an off step 300 depending from the wall perimeter to form a flange raised from the surface of the wall 52' towards the outer wall 50' to effectively form a spacer between the two. In one embodiment, the flange 300 is about 8 millimeters wide, continues around the entire perimeter of the wall 52' and is about 0.5 millimeters thick for effecting the desired spacing between the inner and outer walls. In this embodiment the flange 300 is part of the inner wall 52', and as in the foregoing embodiment, both walls are vacuumed formed plastic, either PET or PVC. The assembly of FIG. 11 can be sonic welded, glued, or adhered with double-sided adhesive. Alternatively, a plurality of intermediate sealing points (not shown) could be used instead of a continuous seal. In this embodiment it can be seen that there is an alternative number of LEDs 12' opposite the forehead portion of the assembly relative to the user so that the number of apertures 70' and LEDs 12' are reduced from the foregoing embodiment from eighteen to fifteen. Either number are viable implementations of the desired therapy, although the other componentry of the assembly FIG. 11 is substantially the same as that shown in the foregoing figures.

Another alternative embodiment from the device shown in FIG. 1, etc. includes disposition of a transparent flexible polymer sheet (not shown) incorporating working LED lights between outer wall 50 and inner wall 52. Such a configuration would comprise the polymer film being coated with a transparent thin layer of carbon nanotubes in a specific configuration to act as the wire pathways to connect LED lights. The polymer would protect the LEDs from user contact. Such protective polymers are available under the Lumisys® brand.

Yet another alternative embodiment includes such a transparent flexible polymer sheet wherein a reflective film is applied on top of the flexible polymer sheet including cutouts opposite the LEDs for allowing the radiant light to communicate through a reflective area in a manner as shown in the relationship of FIG. 4 between the LEDs' 12 inner wall 52 through aperture 70. This arrangement may also include a flexible outer wall 50 on the other side of the flexible polymer sheet to provide malleable rigidity to the film, reflective coating assembly.

Yet another alternative embodiment includes a plurality of sensors (not shown), such as temperature or radiant energy sensors, disposed relative to inner wall 52 to monitor radiant energy exposure of a user during therapy. If such exposure is deemed inappropriate for any reason, sensing thereof is recognized by controller B and the therapy can be halted.

Figure 15:
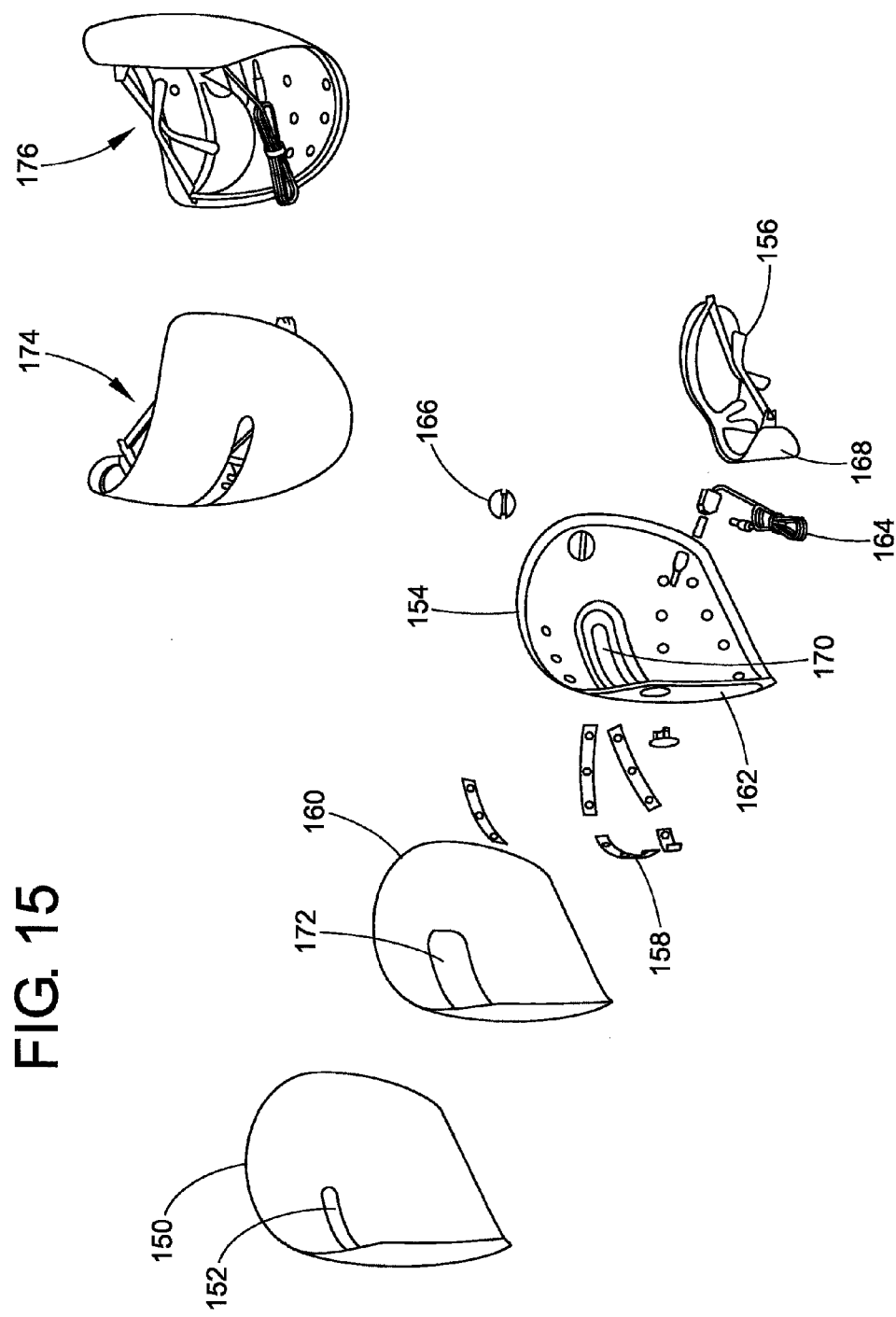
FIG. 15 is an exploded view of an alternative embodiment including a see-through slot and a third light absorbing layer.
Figure 16A:
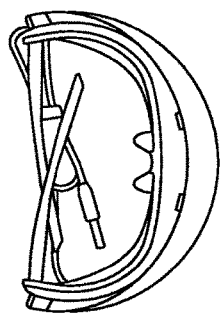
FIGS. 16 (A) (B) (C) and (D) are elevated views of the assembled device of FIG. 15.
Figure 16D:
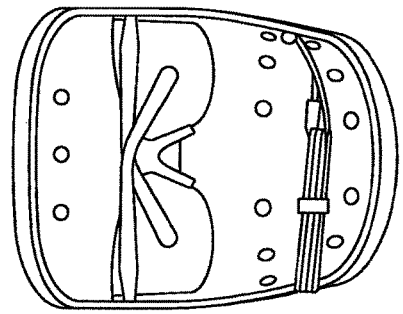
Figure 16C:
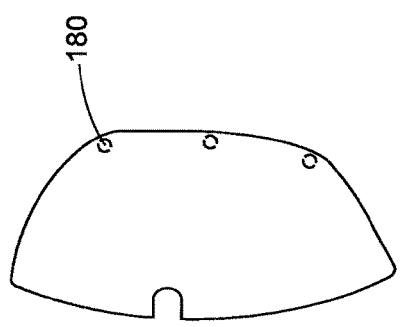
Figure 16B:
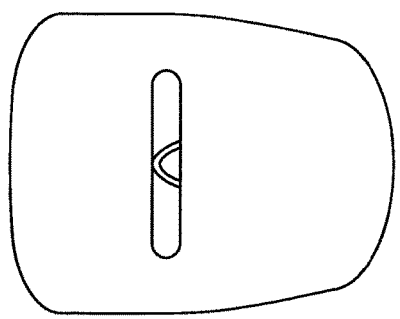

FIG. 15 shows yet another alternative embodiment including an outer shield 150 including a see-through slot 152, an inner reflective shield 154, and eyeglass assembly 156, and LED strips 158. These elements are substantially similar, but for the see-through slot 152 and corresponding aligned slots, as the foregoing embodiments. Alternatively, this embodiment includes a third layer 160 intermediate the outer shield 150 and the inner shield 154. Layer 160 preferably comprises a thin opaque black plastic sheet which serves to absorb or block out lamp radiation and eliminate all light leakage from the front of the mask, i.e., out through the outer shield 150. Layer 160 is preferably affixed to the inside of the outer layer 150 and then the LED strips are affixed to the layer 160. The strips 158 still remain recessed relative to the inner surface 162 of the inner shield 154 for the benefits noted above. FIG. 15 also shows a controller assembly cable 164 and an eyeglass assembly mounting post 166. The eyeglass assembly lenses 168 are tinted but do not preclude a user to see through the inner shield slot 170, the third layer slot 172 and the outer shield see-through slot 152. The aligned slots 152, 170, 172 comprise a continuous viewing opening that is an integral part of the mask. A layer 160 is sized to provide perimeter spacing from the outer perimeter of the outer shield 150. When the unit is operating and the LEDs are illuminated, this provides a perimeter illumination to an observer of the user which not only communicates that the unit is in operation but provides an aesthetically pleasing appearance.

In one embodiment the LED strips 158 are preferably attached to the intermediate third layer 160 by being received in corresponding pockets (not shown) in the layer 160. Alternatively, they can be adhesively applied to the layer 160. The wires between the strips 158 are very thin and just rest between the middle layer and the inner shield 154, i.e., no special wire routing. There is accommodation for the main cable and strain relief—leading to the first LED strip. The whole middle layer assembly fits into the chamfered recess in the inner shield 154, and there are locating points top/bottom and left/right. This is secured with double-sided tape. The middle layer/LED strips/inner shield assembly is completed by the outer shield 150 (also by double-sided tape). There are several sonic welds 180 (FIG. 16) that permanently secure the layers together. Assembled perspective views 174, 176 are shown. FIGS. 16 (A), (B), (C), and (D) illustrate elevated views of the embodiment of FIG. 15 when assembled.

Figure 17:
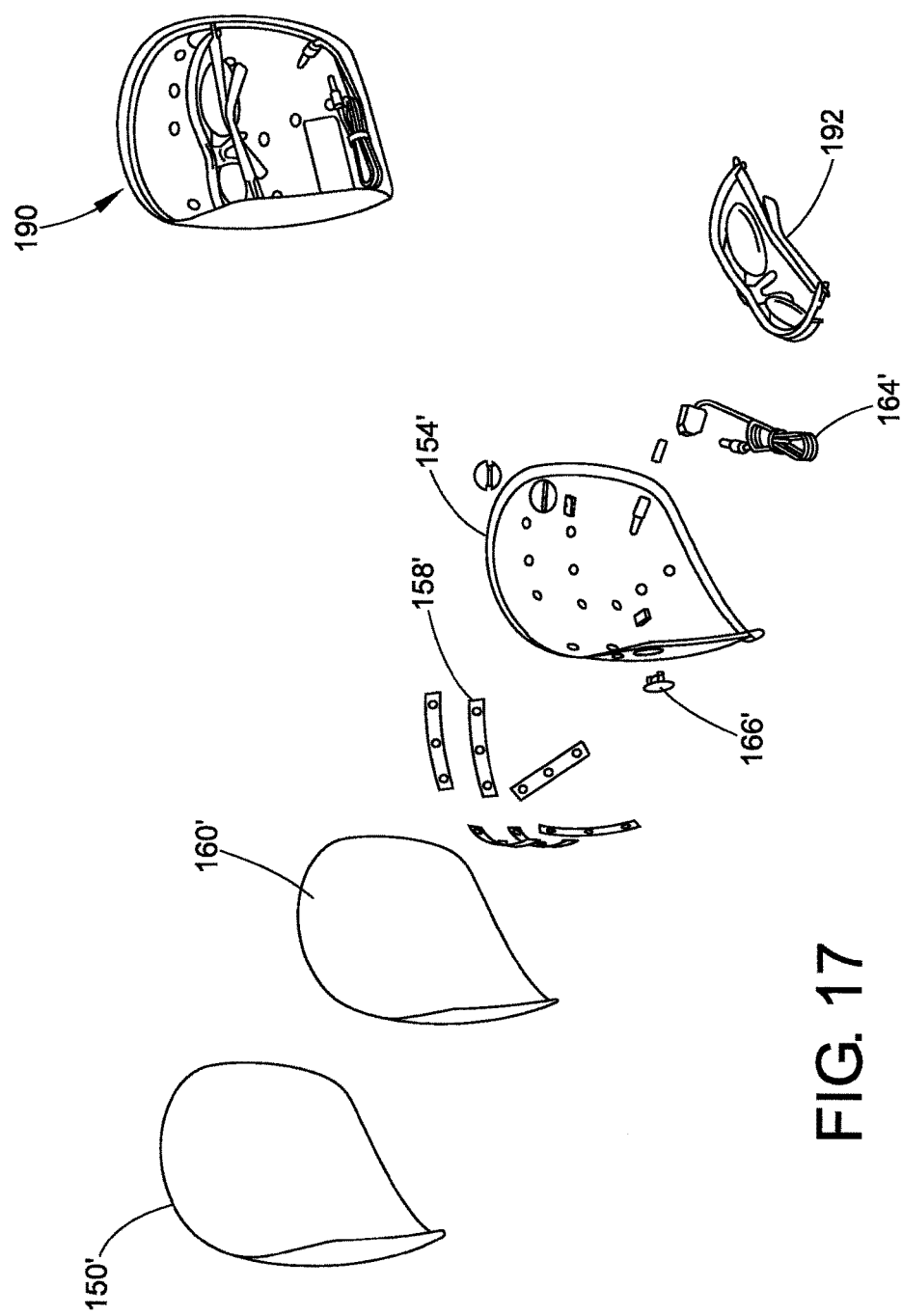
FIG. 17 is an exploded view of an alternative embodiment including eye protecting goggles.

FIG. 17 is yet another alternative embodiment which differs from the embodiment of FIG. 15 in that the see-through slots 152, 170, 172 have been eliminated and the eyeglass assembly 190 no longer has tinted lenses, but radiant light blocking goggles 192. Like elements from FIG. 15 are same numbered and primed. In this embodiment, the eyes are to be protected from any of the radiant energy emitted by the lamps. Such an embodiment is particularly useful for a phototherapeutic treatment of red and infrared light for an anti-aging therapy. A red light evens skin tone and reduces roughness. Infrared light reduces the appearance of fine lines and wrinkles. However, whatever radiant energy may be employed, the goggles 192 completely shield the eyes from the radiant energy.

Figure 18:
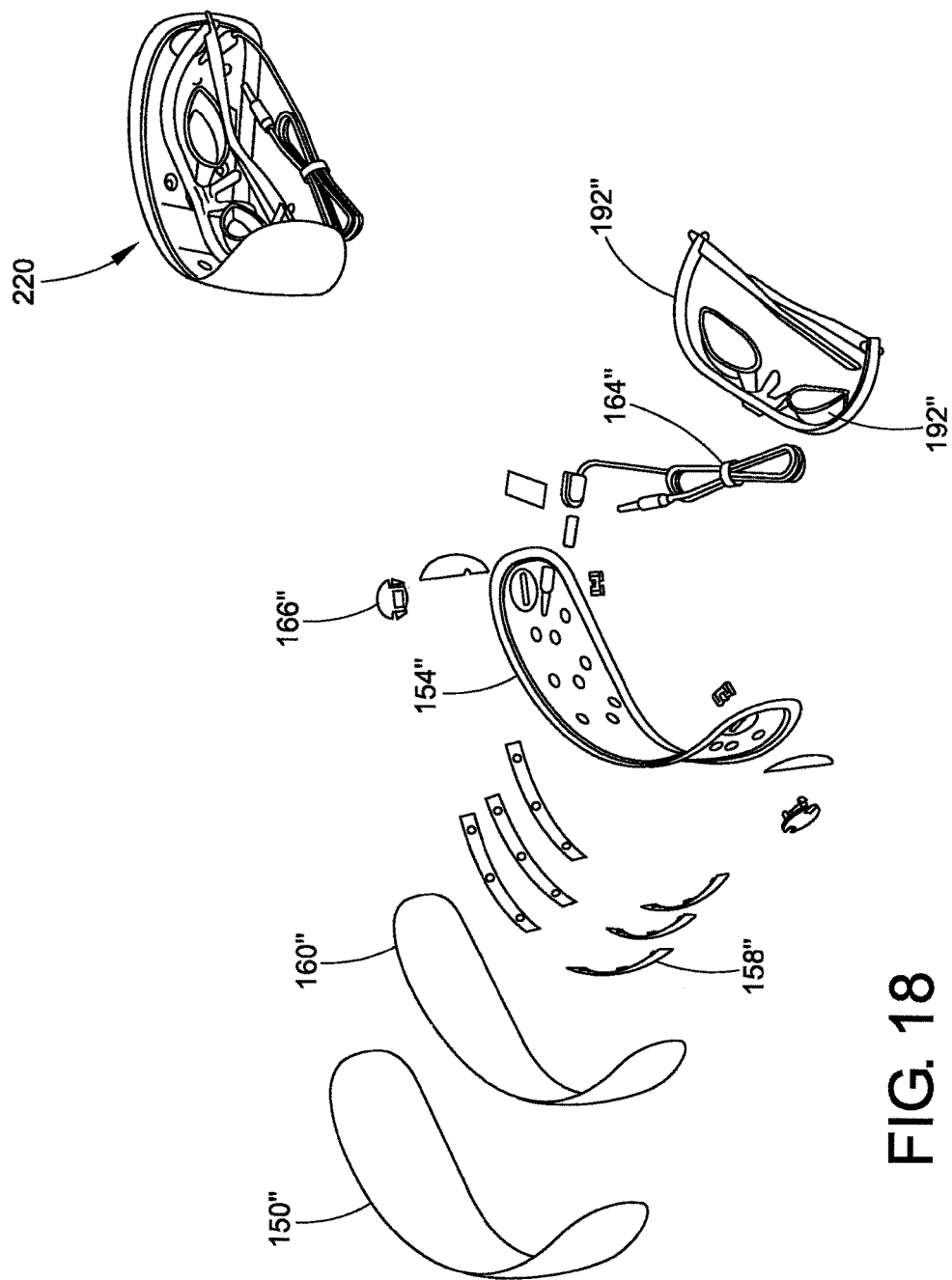
FIG. 18 is an exploded view of an alternative embodiment having a mask sized for applying the LED therapy to the eye area.

FIG. 18 is yet another embodiment where the mask assembly 220 is sized to only treat the eye area of a patient so that the assembled mask is much smaller than that shown in FIG. 17. The LED strips 158" are disposed in a different arrangement from that FIG. 16 but the other elements are essentially the same including the protective goggles 192".

It is a common feature of the embodiments described thus far that the LED lamps remain recessed relative to the inner surface 162 of the inner shield 154 for comfort and safety purposes relative to the user.

Figure 19A:
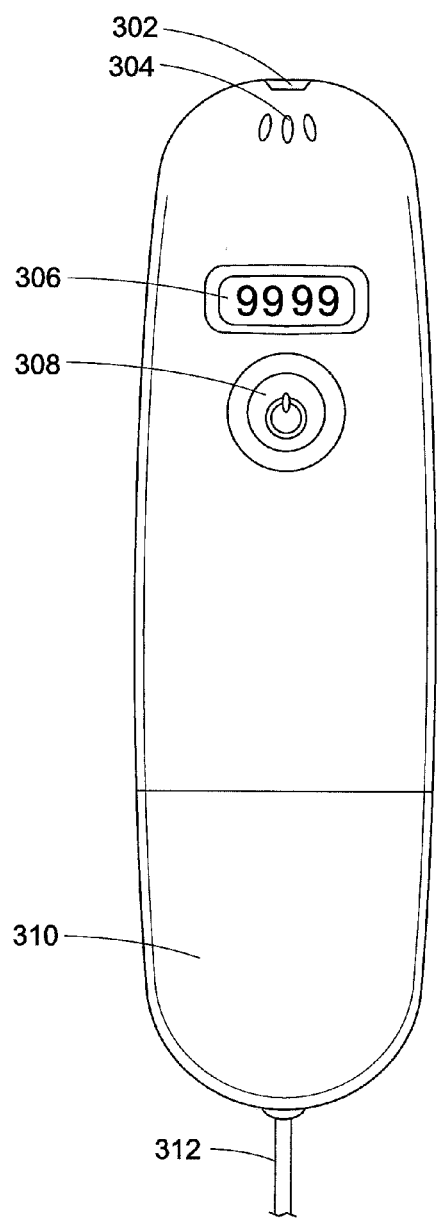
FIGS. 19A and 19B illustrate a front view and side view respectively of a therapeutic lamp platform controller including a SIM cartridge refill according to an exemplary embodiment of this disclosure.
Figure 19B:
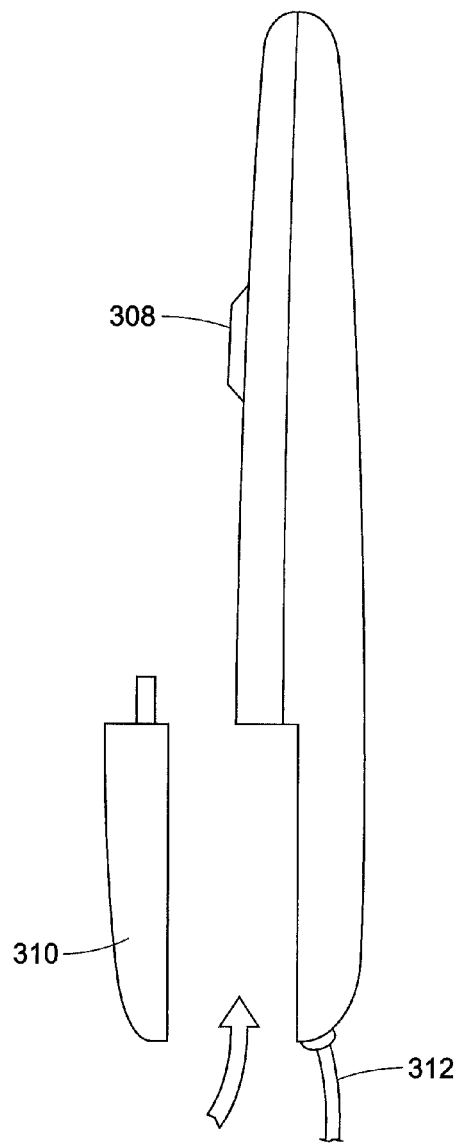

With reference to FIGS. 19A and 19B, illustrated is a front view and side view respectively of a therapeutic lamp platform controller including a SIM cartridge refill according to an exemplary embodiment of this disclosure.

As shown, the controller includes a battery charger port 302, a charge state indication 304, a LCD display 306, an On/Off button 308, a dosage refill cartridge 310 and a cable 312 which is operatively connected to a light therapy platform mask.

The SIM cartridge refill 310 provides a manner for a user to purchase additional dosages for the device. For example, a user may purchase a SIM cartridge refill cartridge which authorizes an additional 30, 60, or 90 dosages. In operation, the controller communicates with the SIM cartridge after the user attaches to the device and a series of program instructions are performed to validate the SIM cartridge and activate an additional number of available dosages to be delivered by the device. In addition, controller program instructions are provided to deactivate the use of SIM cartridge refill after the controller dosage counter has been increased by the SIM cartridge refill replenishment dosage amount.

Figure 5:
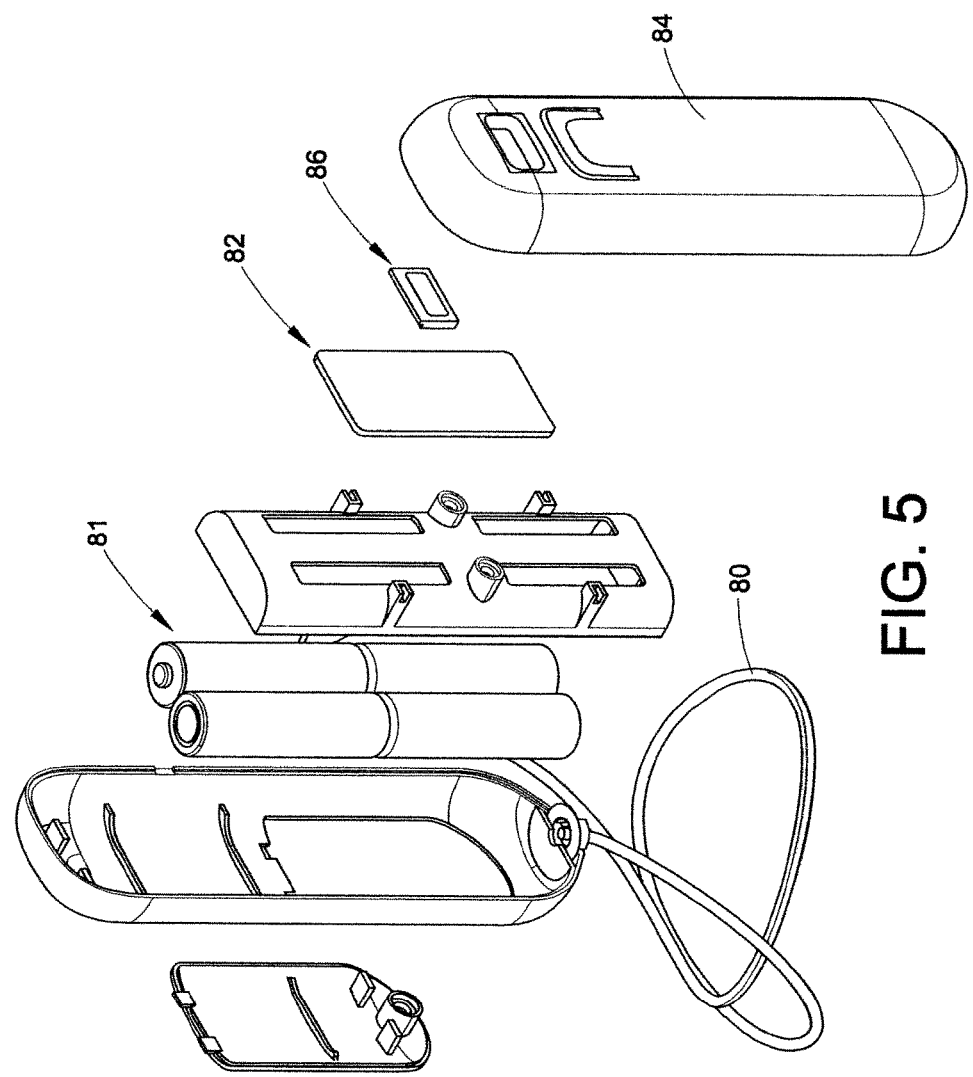
FIG. 5 is an exploded perspective view of the controller B.
Figure 6:
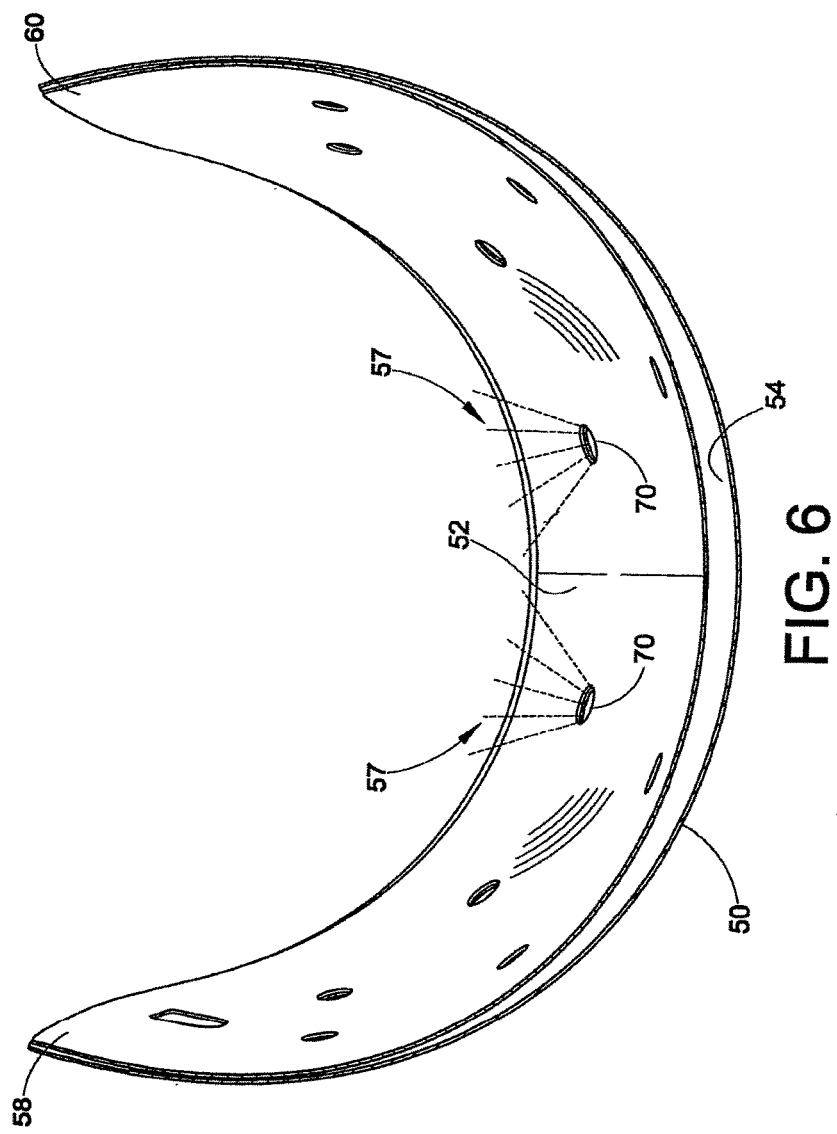
FIG. 6 is a cross-sectional view showing a two-wall structure of the embodiment of FIG. 1 wherein an inner wall includes light apertures aligned with the LEDs for communicating the therapeutic light to the user.
Figure 7:
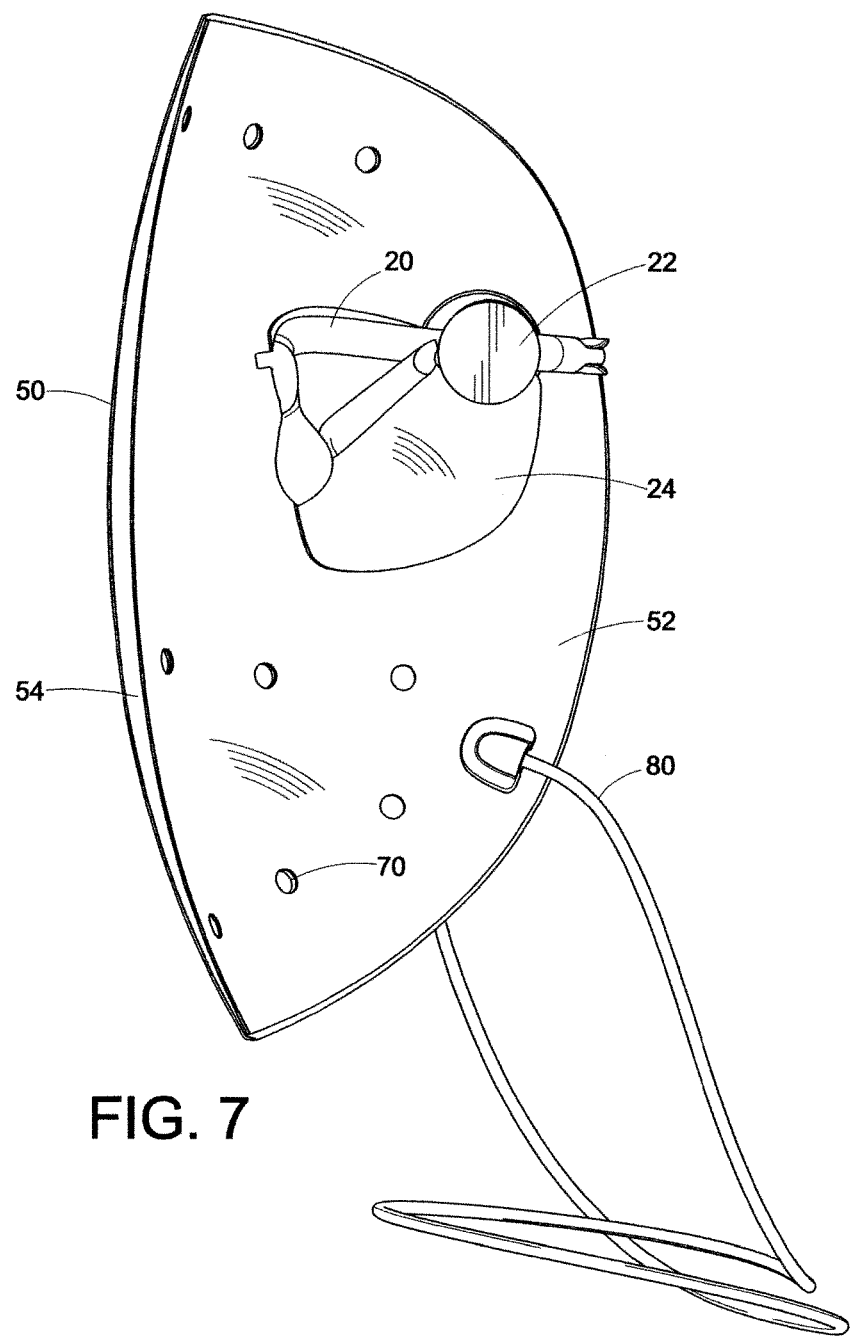
FIG. 7 is a second cross-sectional view taken along a vertical center-line.
Figure 8:
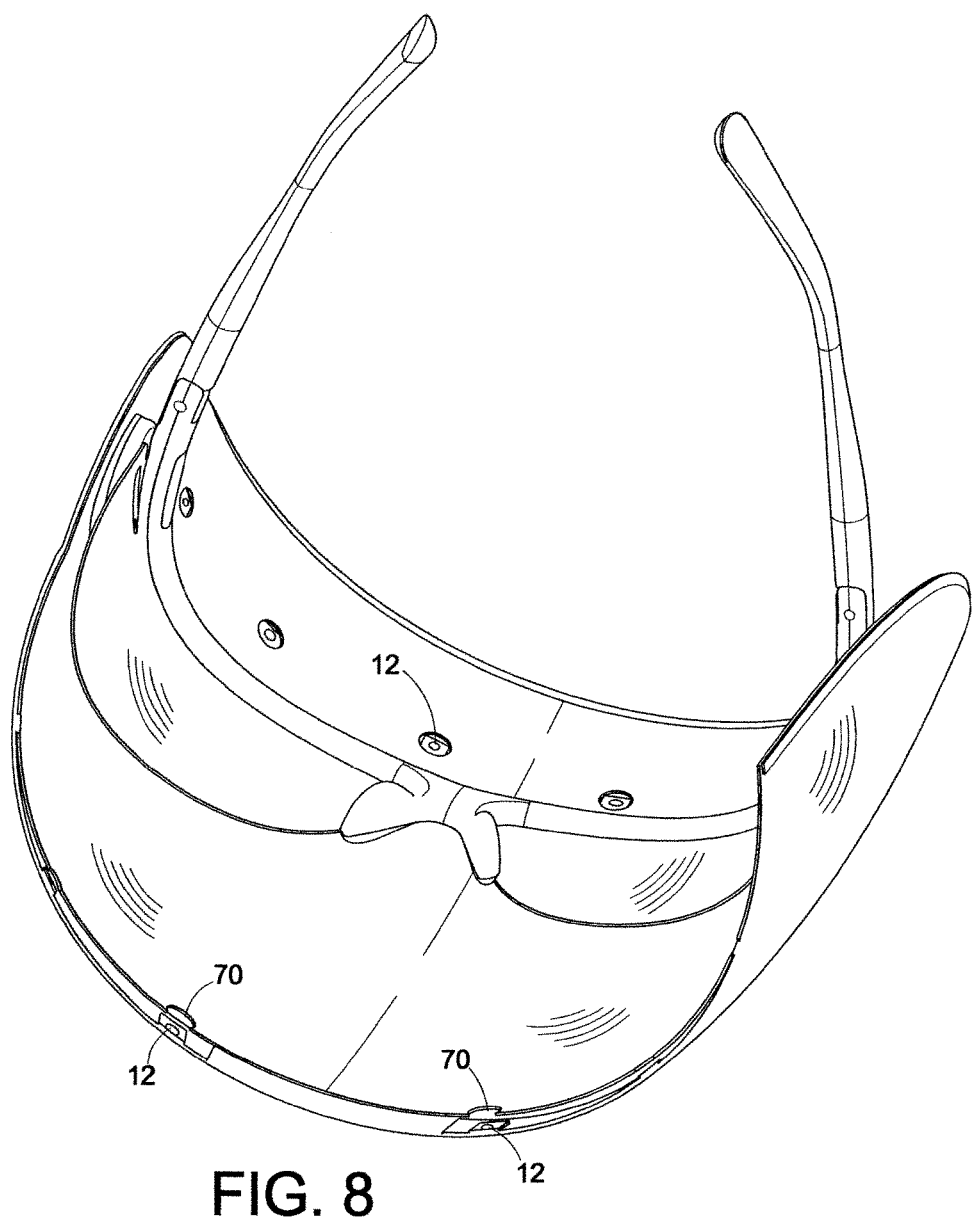
FIG. 8 is a partial cross-sectional perspective view illustrating disposition of recessed LED lamps relative to inner wall apertures.
Figure 20A:
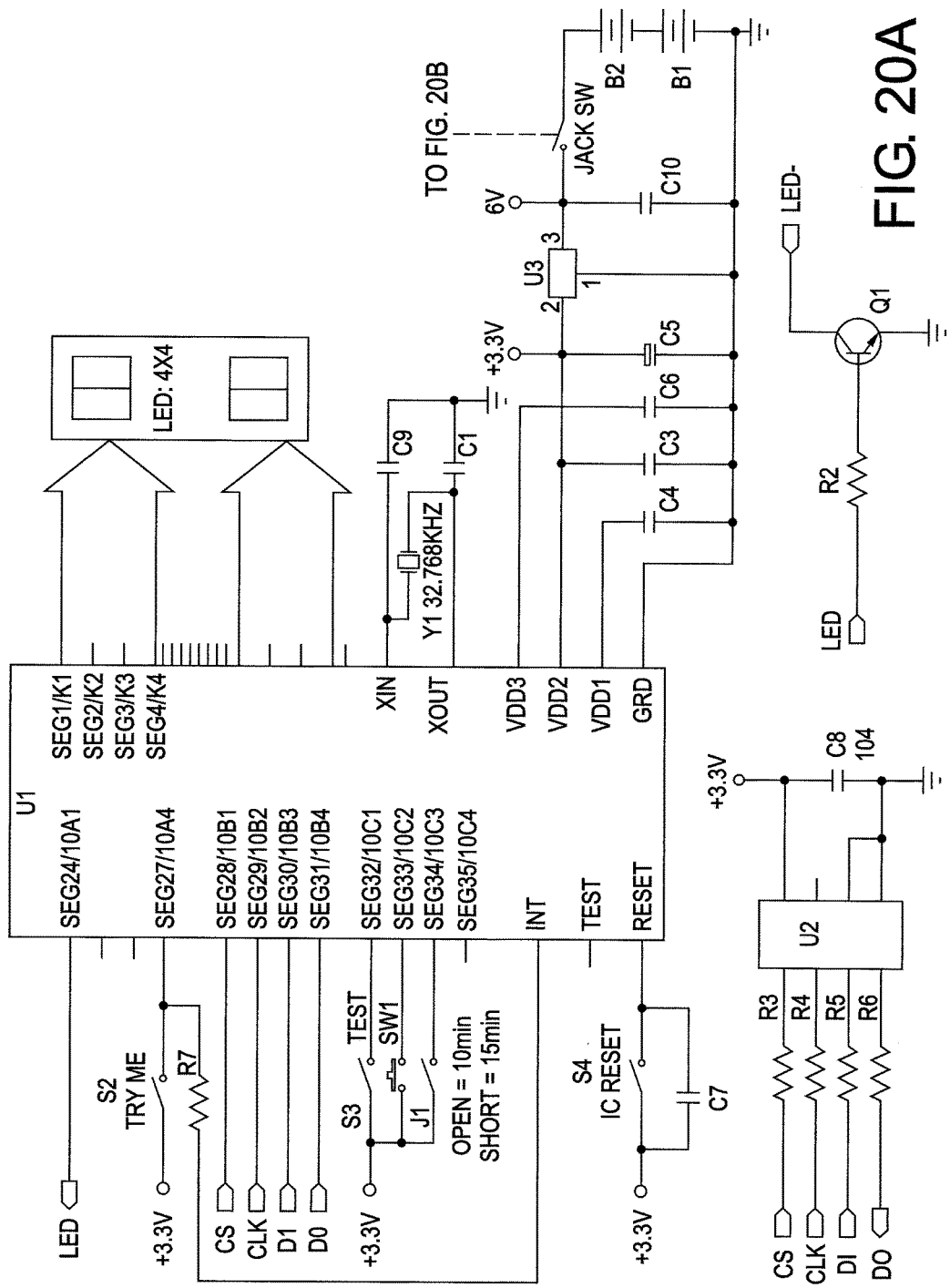

With reference to FIGS. 20A and 20B, shown is a schematic of a first therapeutic lamp platform controller as shown in FIG. 5, according to an exemplary embodiment of this disclosure.

As shown, the controller includes a microcontroller U1 which executes program instructions based on a control program, as well as inputs associated with switch SW1 (On/Off Button), S2 (Try Me Switch) and switch S4 which resets the device. The microcontroller U1 drives a 4×4 LCD as well as the lamp radiation LEDs D1-D18 using circuitry including capacitors C4, C3, C6, C5, and C10, Batteries B1 and B2, Resistors R70, R80, R9, R10, R11, R12, R13, R14, R15, R8, R22, R23, R21, R20, RR19, R18, R17, and R16, and driver circuit including resistor R2, and transistor Q1.

With reference to FIG. 21A, illustrated is a perspective view of another second therapeutic lamp platform controller according to an exemplary embodiment of this disclosure, and FIG. 21B, shows an exploded view of another second therapeutic lamp platform controller according to an exemplary embodiment of this disclosure.

As shown, the controller 320 includes a front housing 322, a LCD display 324, an On/Off button switch 326, a PCB 328, a rear housing 338, a plurality of batteries 344 and a battery cover 348.

Figure 22A:
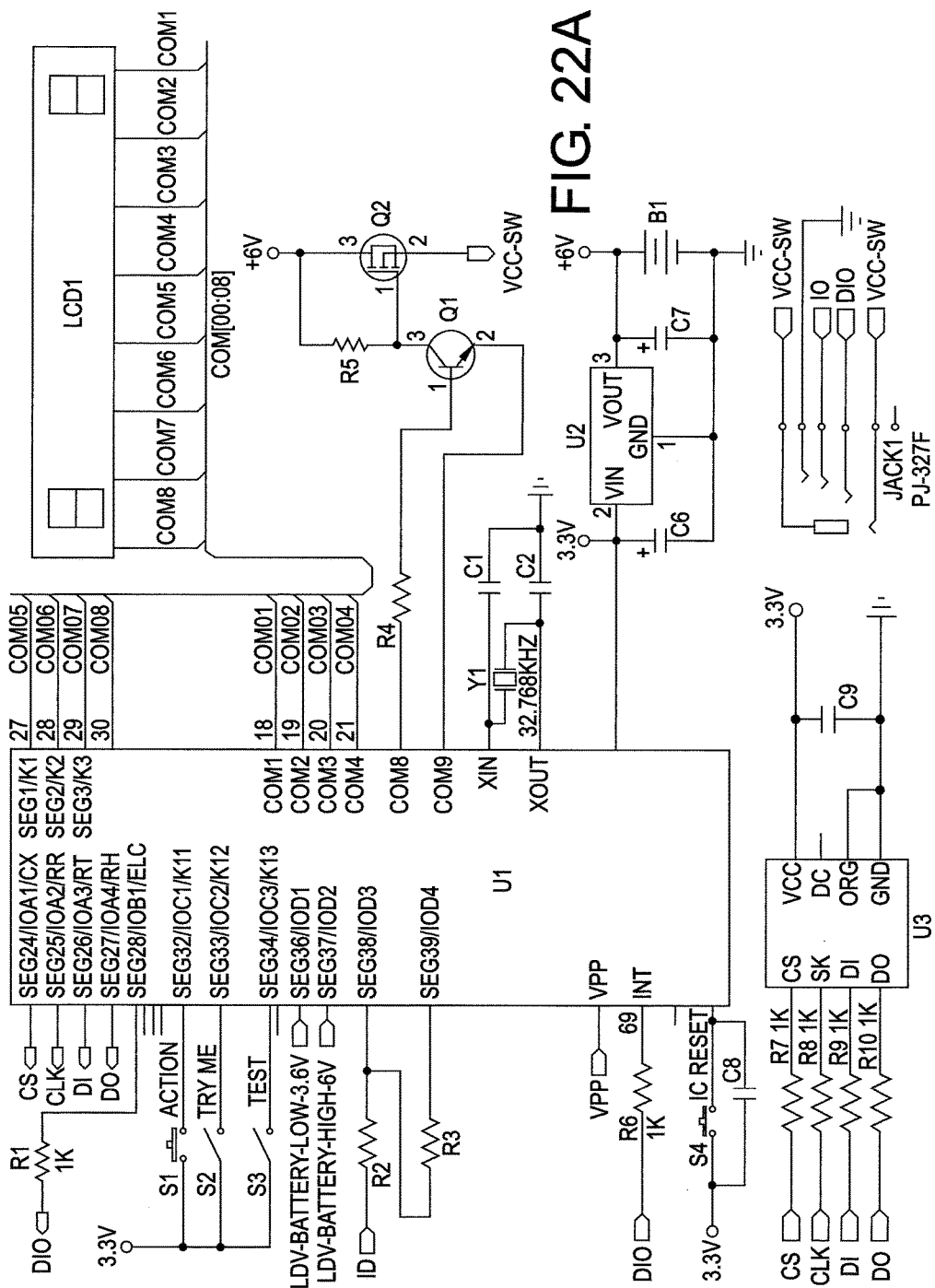
FIGS. 22A, 22B and 22C is a schematic of the second therapeutic lamp platform controller shown in FIG. 21, according to an exemplary embodiment of this disclosure.
Figure 22B:
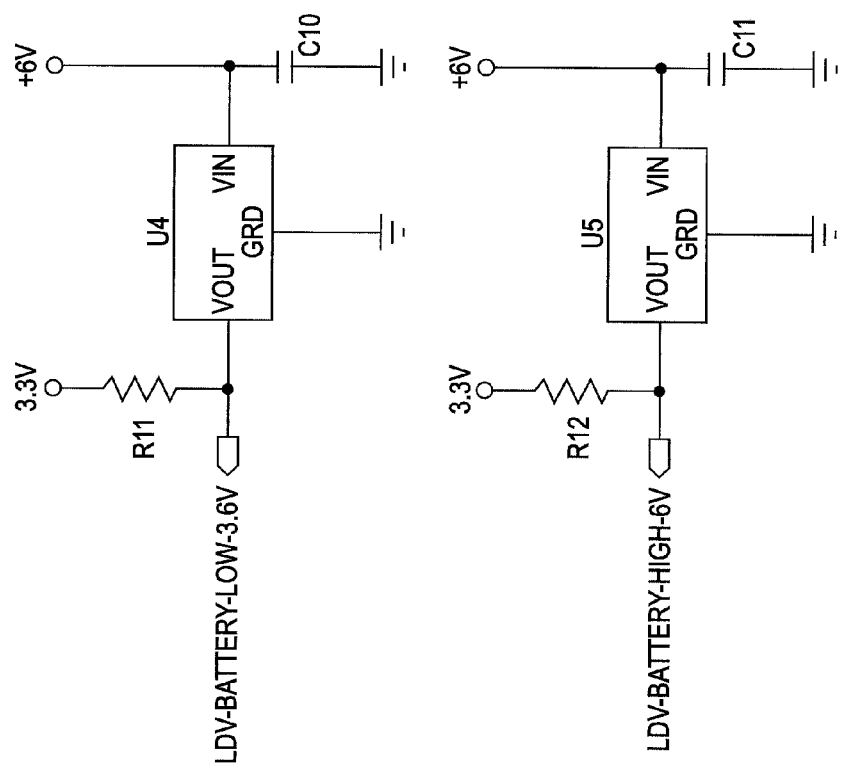
Figure 22C:
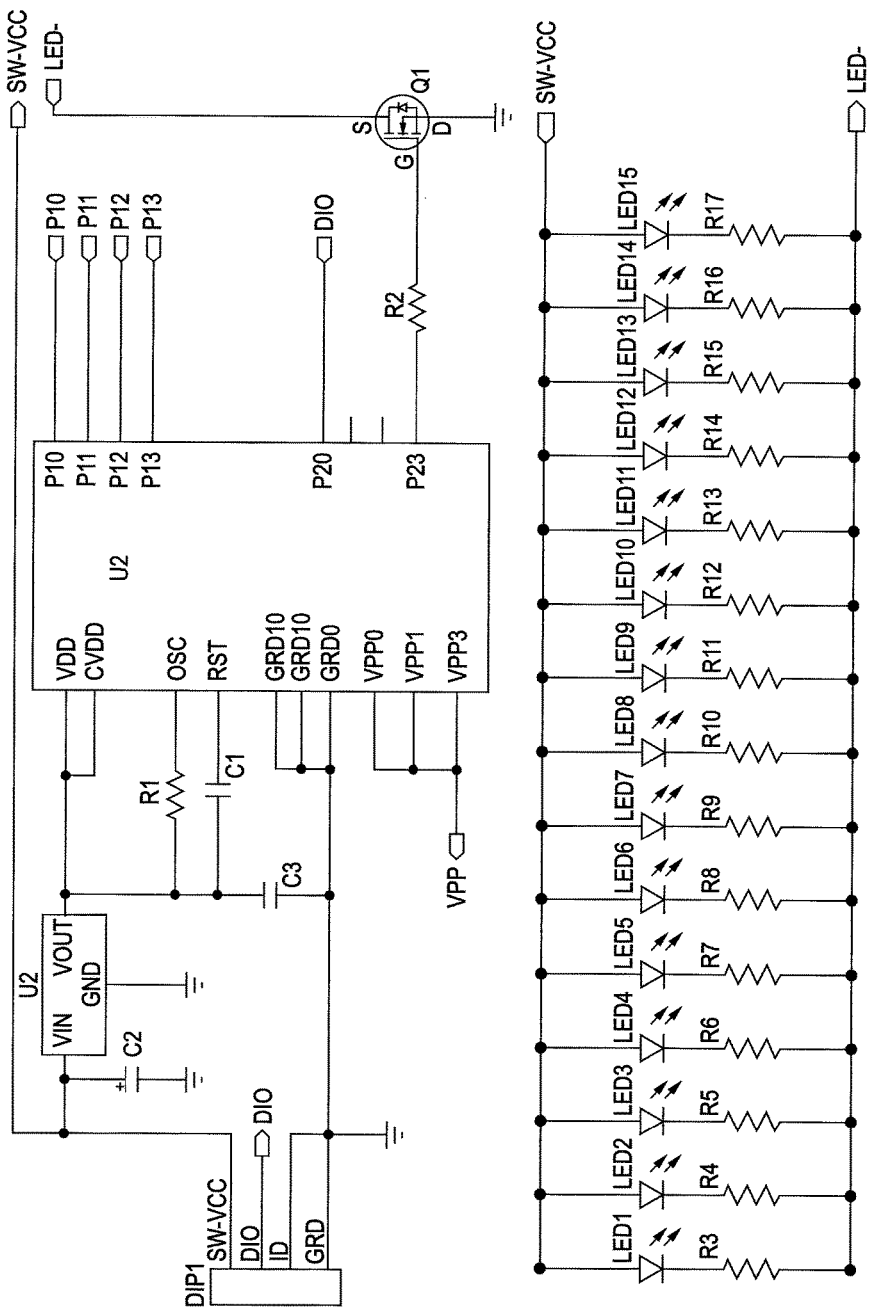

With reference to FIGS. 22A, 22B and 22C, illustrated is a schematic of the second therapeutic lamp platform controller shown in FIG. 21, according to an exemplary embodiment of this disclosure.

As shown, the controller includes a microcontroller U1 which drives LCD 1, and communicates with microcontroller U2 which is housed within a mask. The circuitry shown in FIG. 22A resides in the controller and the circuitry shown in FIG. 22B resides in the mask.

By operating a second microcontroller housed within the mask, microcontroller U1 can execute instructions to determine if a mask is authorized to be operated by the controller.

In contrast to the controller illustrated schematically in FIGS. 20A and 20B, the controller shown in FIGS. 22A, 22B and 22C includes circuitry to monitor various states of the battery to provide notification to a user that the battery requires charging/replacement, in addition to insuring adequate power for executing an active dosage request.

Figure 23:
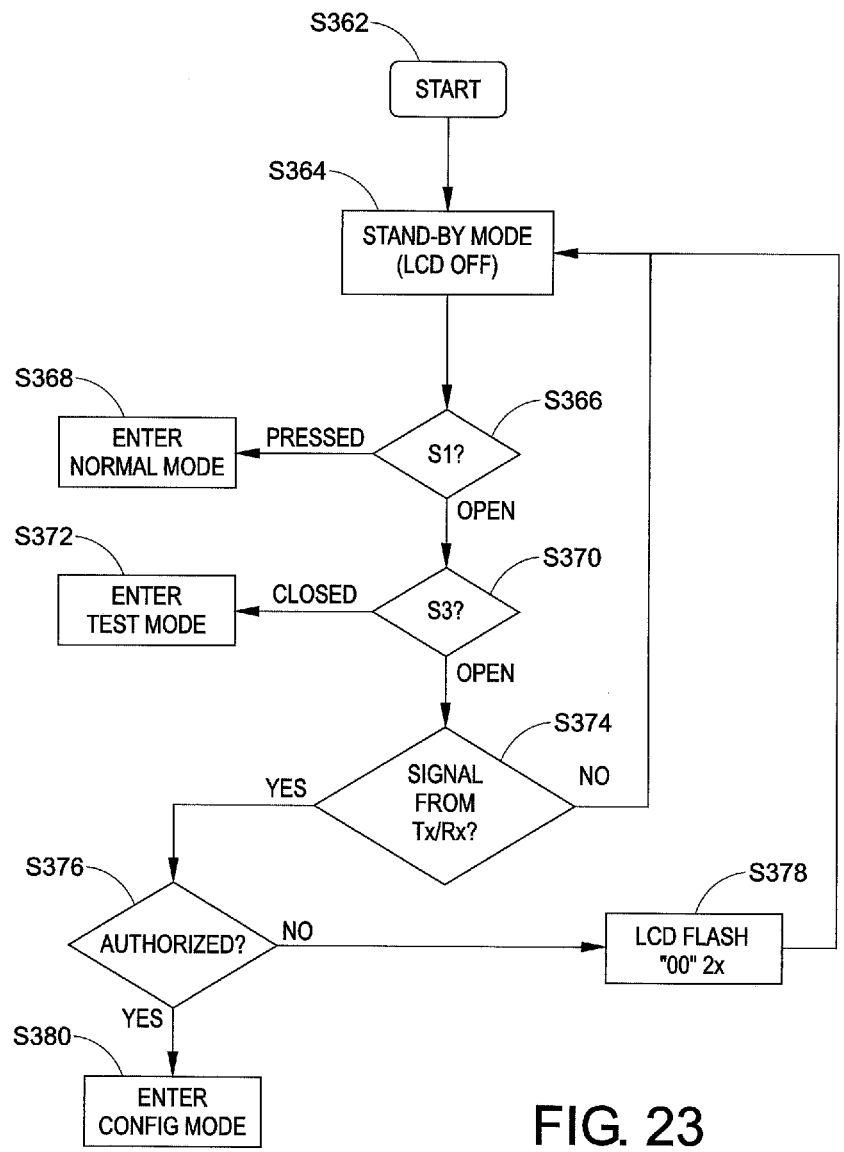
FIG. 23 is a flow chart of the operational control of a therapeutic lamp platform according to an exemplary embodiment of this disclosure, the operational control including a Stand-By Mode, Normal Mode, Test Mode and Configure Mode.

With reference to FIG. 23, shown is a flow chart of the operational control of a therapeutic lamp platform according to an exemplary embodiment of this disclosure, the operational control including a Stand-By Mode, Normal Mode, Test Mode and Configure Mode.

Figure 24:
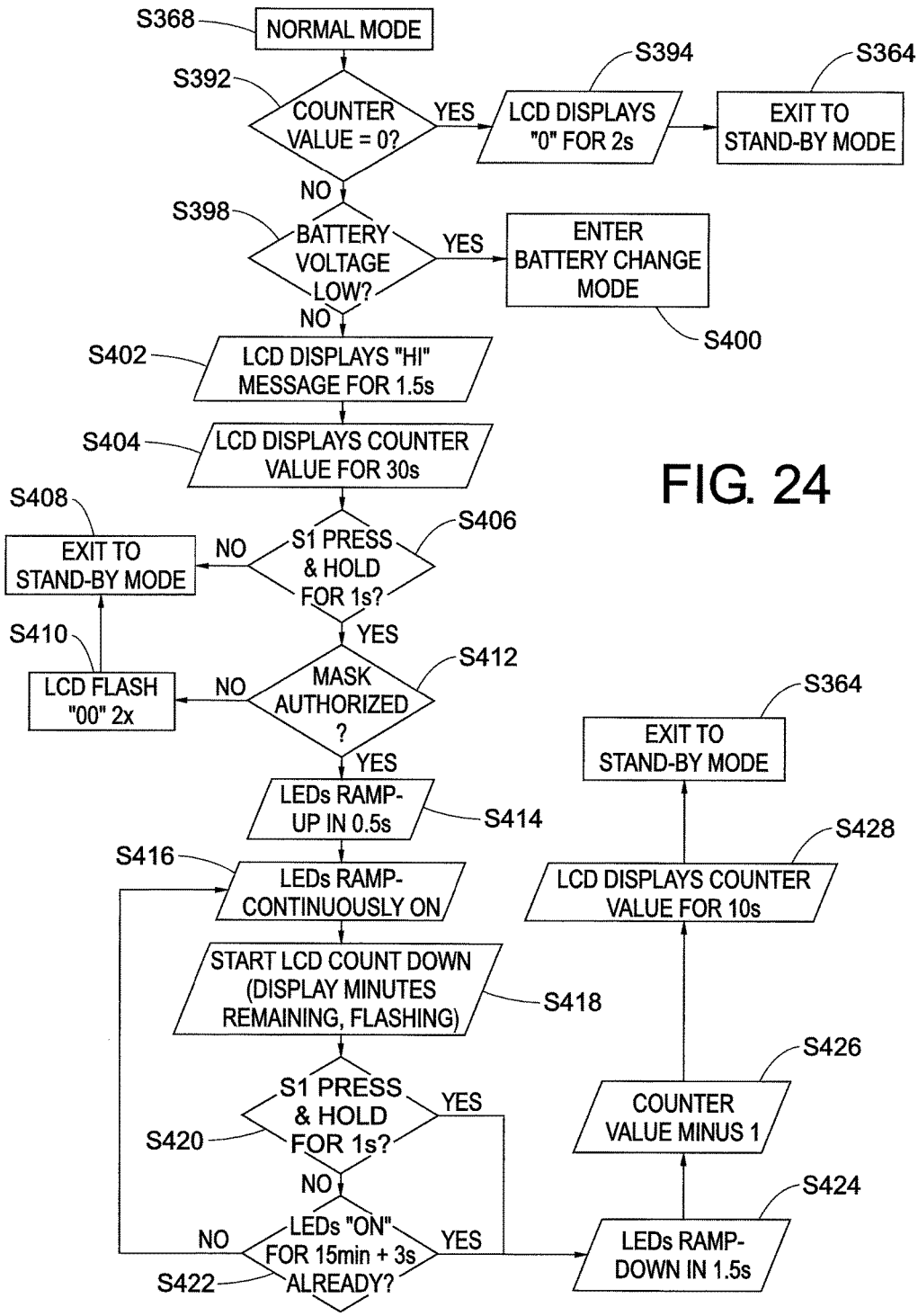
FIG. 24 is a flow chart of the operational control of a Normal Mode associated with a therapeutic lamp platform controller according to an exemplary embodiment of this disclosure.

With reference to FIG. 24, illustrated is a flow chart of the operational control of a Normal Mode S368 associated with a therapeutic lamp platform controller according to an exemplary embodiment of this disclosure.

At step S392, the control program determines if a dosage counter value is 0, and if true proceeds to step S394 to display "0" notifying the user that the controller requires additional dosage authorization or replacement, and then proceeds to exit to Stand-By Mode at step S364.

If the dosage counter is greater than 0, the control program proceeds to step S398 to determine if the battery voltage is low. If a low battery voltage condition is detected, the control program proceeds to step S400 and enters Battery Charge Mode.

If the battery voltage is acceptable, the control program executes step S402 to display "Hi" and step S404 displays the dosage counter.

At step S406, the control program waits for the On/Off button to be pressed for 1 second, where the control program exits to Stand-By Mode if switch S1 is not pressed for 1 second. After S1 switch is pressed for 1 second, the control program proceeds to step S412 to determine if the mask is authorized to be operated with the controller.

If the mask is not authorized, the control program flashes "00" two times on the LCD at step S410 and then proceeds to Stand-By Mode at step S408. If the mask is authorized, the control program proceeds to step S414 to ramp up power to the LEDs in 0.5 seconds, and step S416 to turn the LEDs continuously "On", step S418 to start the LCD countdown indicating the amount of time remaining for the current active dosage session.

At step S420, the control program monitors S1, where the user pressing the On/Off button for 1 second will initiate the terminating of the active dosage session by the control program executing step S424 to ramp-down the LED power in 1.5 seconds, step S426 to decrement dosage counter by 1, step S428 to display on the LCD the remaining number of dosages available and step S364 to exit to Stand-By Mode.

If, at step S420, switch S1 is not pressed, the control program executes step S422 to monitor the time expired for the current active dosage session and executes steps S416, S418, S420 and S422 until the dosage time limit has been reached, at which point steps S424, S426, S428 and S364 are sequentially executed during an LED power down process as previously described.

Figure 25:
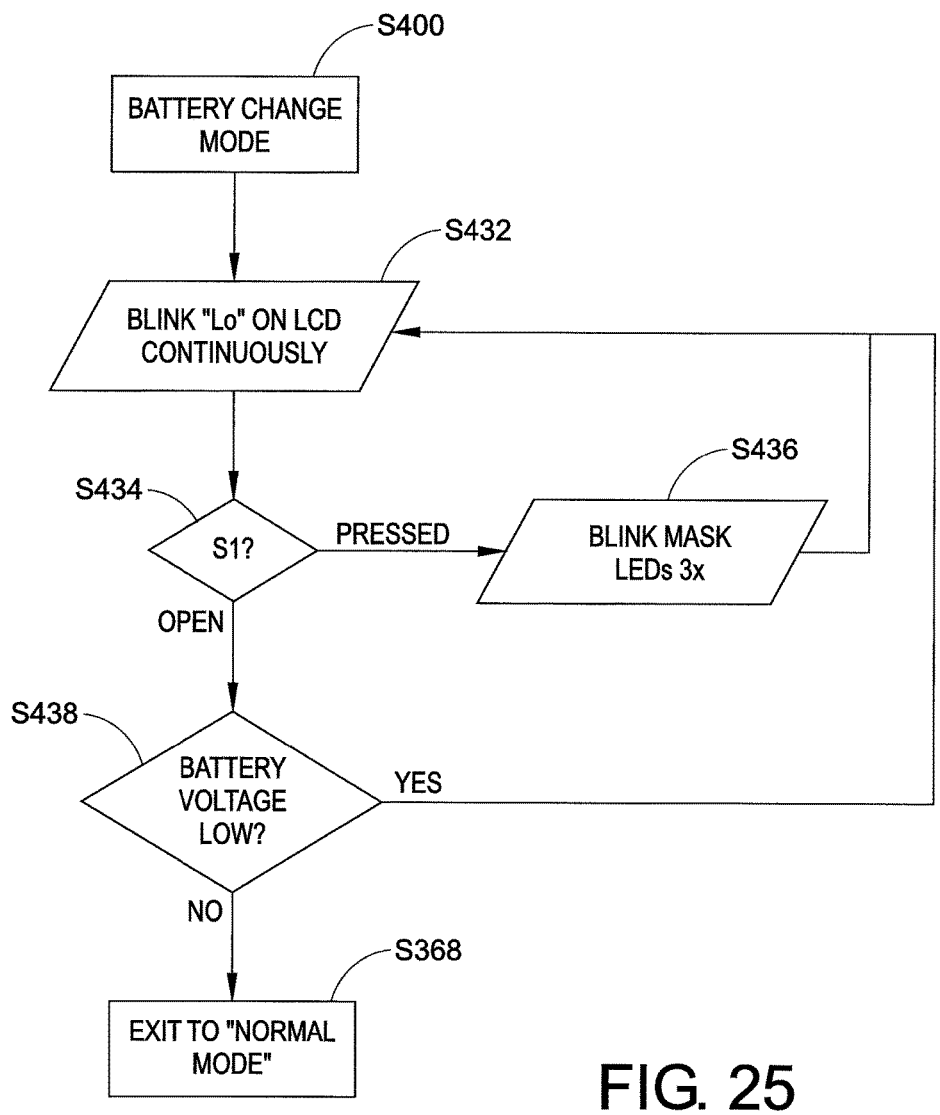
FIG. 25 is a flow chart of the operational control of a Battery Charge Mode associated with a therapeutic lamp platform controller according to an exemplary embodiment of this disclosure.

With reference to FIG. 25, shown is a flow chart of the operational control of a Battery Charge Mode S400 associated with a therapeutic lamp platform controller according to an exemplary embodiment of this disclosure.

As shown, the control executes step S432 to blink "Lo" on the LCD continuously to notify the user the battery is low, and if the user presses the On/Off control switch (S1) while the battery is low, step S436 blinks the mask LEDs to provide additional notification to the user the battery needs recharged/replaced.

Figure 26:
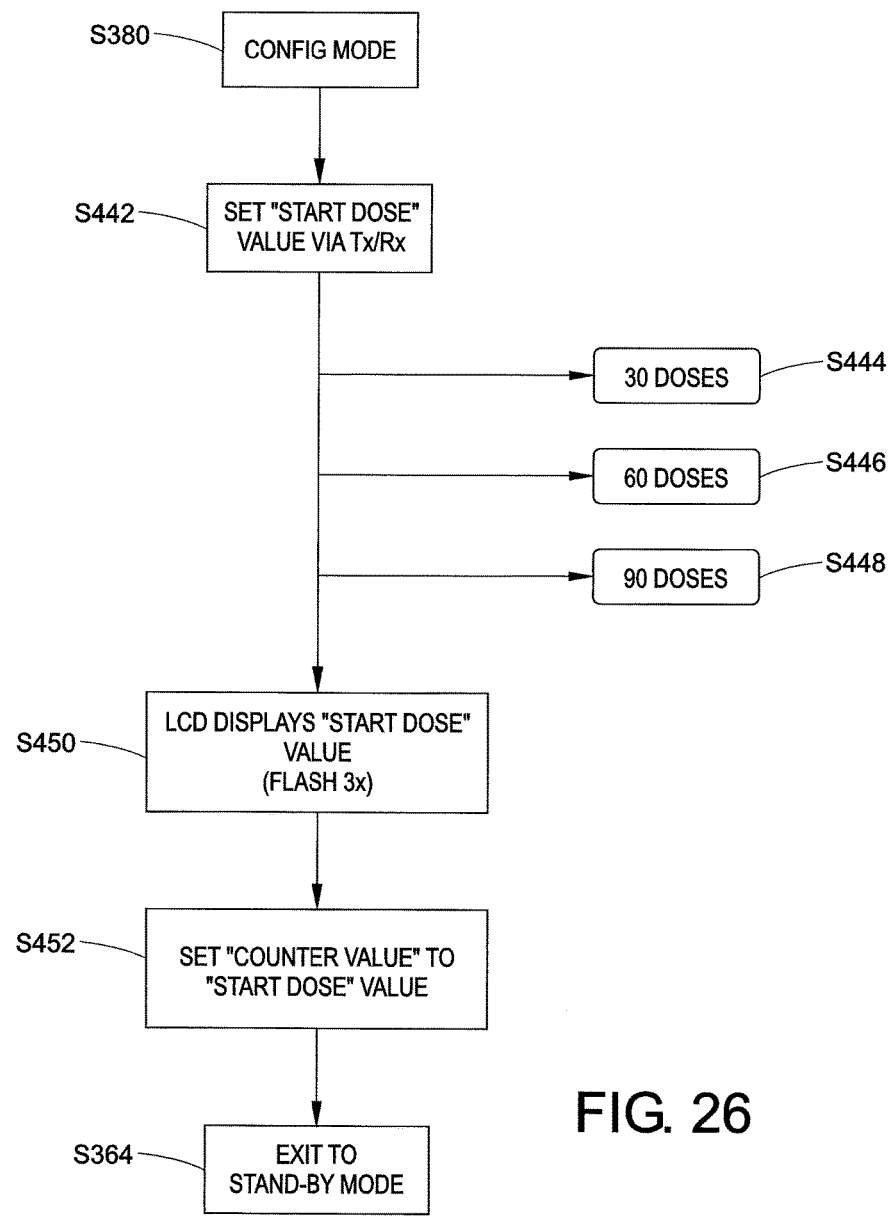
FIG. 26 is a flow chart of the operational control of a Configuration Mode associated with a therapeutic lamp platform controller according to an exemplary embodiment of this disclosure.

With reference to FIG. 26, illustrated is a flow chart of the operational control of a Configuration Mode S380 associated with a therapeutic lamp platform controller according to an exemplary embodiment of this disclosure.

As shown, the controller executes step S442 to get a "Start Dose" value via Tx/Rx, where step S444 sets the dosage limit at 30 doses, step S446 provides 60 doses and step S448 provides 90 doses.

At step S450, the control program displays the "Start Dose" value selected, and at S452 the "Counter Value" is set to the value selected, i.e. 30, 60, or 90 doses.

At step S364, the control program exits to Stand-By Mode.

As shown, after the control program enters Test Mode, step S462 is executed to provide a LCD Quick Display Test, step S464 displays the LCD bonding status, step S466 sets "Display Value" to 01. "=05", step S468 blinks "Display Value" and step S470 proceeds to exit to Stand-By Mode at step S364 unless switch S3 is closed by the user, in which case the control program proceeds to step S472 and if S1 is not pressed, the control program repeats execution of step S468. If switch S1 is pressed, the control program proceeds to step S474 and compares the counter dosage value with the start dosage value.

If the counter dosage value is not equal to the start dosage value, the control program returns to step S468, otherwise step S478 lights up the LEDs for 2 seconds and step S476 decrements the displayed dosage counter value.

At step S480, if the display value equals 0, then the control program proceeds to step S468, otherwise the control program proceeds to step S482 and displays "00" for 2 seconds and then exits to Stand-By Mode at step S634.

Figure 27:
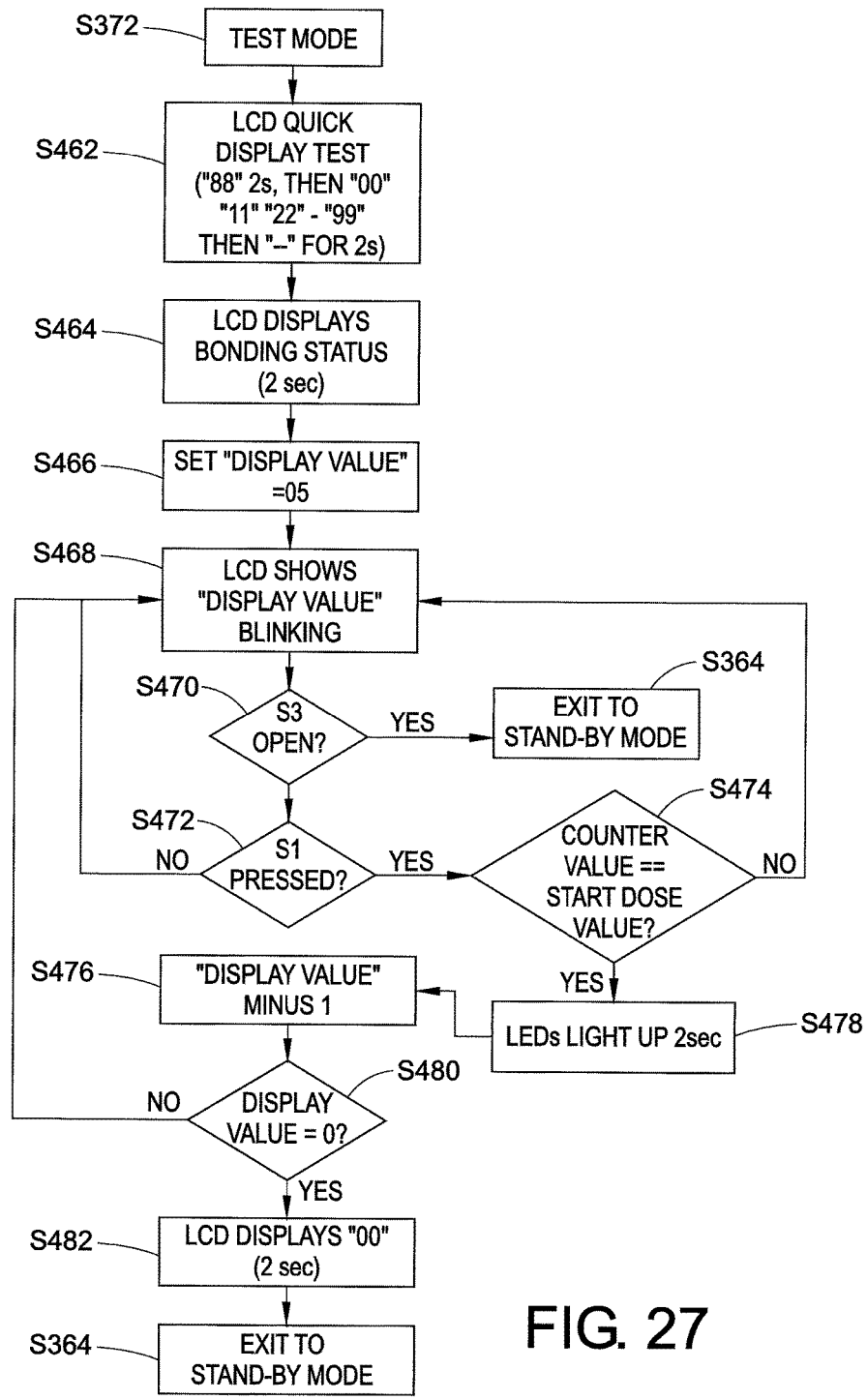
FIG. 27 is a flow chart of the operational control of a Test Mode associated with a therapeutic lamp platform controller according to an exemplary embodiment of this disclosure.

With reference to FIG. 27, shown is a flow chart of the operational control of a Test Mode S372 associated with a therapeutic lamp platform controller according to an exemplary embodiment of this disclosure.

Figure 28:
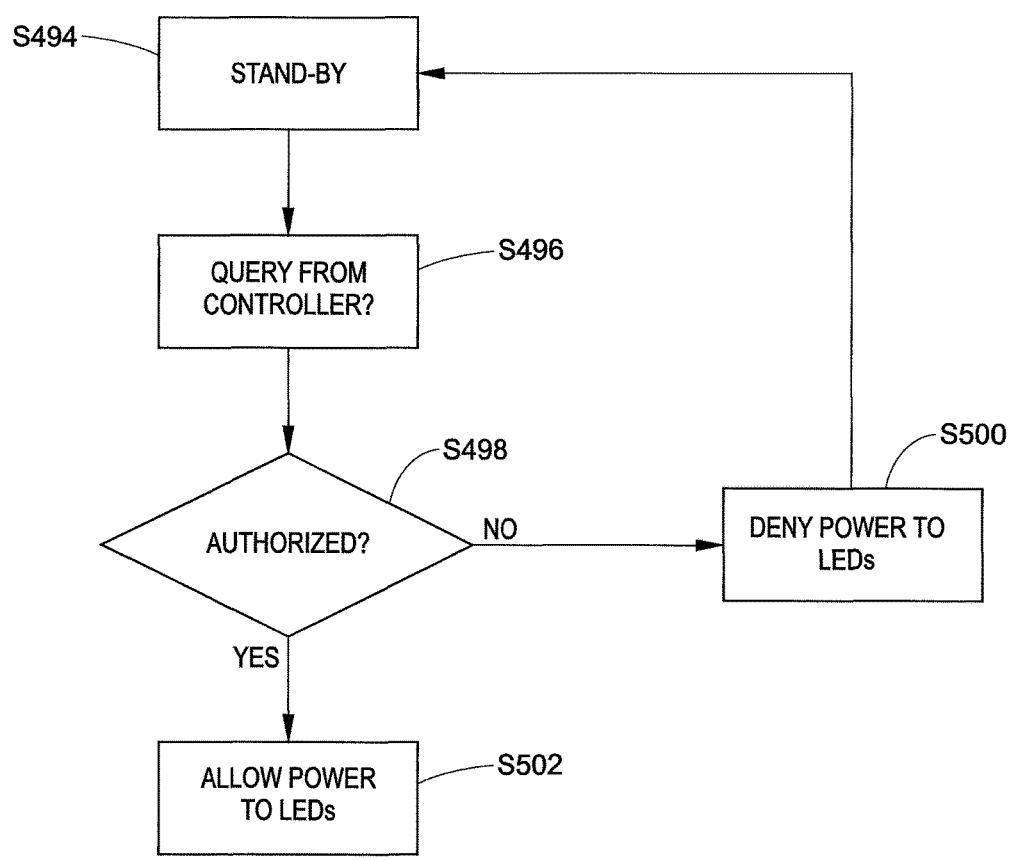
FIG. 28 is a flow chart of the operational control of a Stand-By Mode associated with a therapeutic lamp platform controller including an independent mask controller configured to determine authorization of a mask/controller combination, according to an exemplary embodiment of this disclosure.

With reference to FIG. 28, illustrated is a flow chart of the operational control of a Stand-By Mode S949 associated with a therapeutic lamp platform controller including an independent mask controller configured to determine authorization of a mask/controller combination, according to an exemplary embodiment of this disclosure.

As shown, at step S496, the mask controller receives an authorization query from the controller.

At step S498, the mask controller determines if the controller/mask is authorized to be operated, where step S500 denies power to the LEDs if proper authorization is not obtained and S502 allows power to the LEDs if the controller/mask is authorized.

Figure 29:
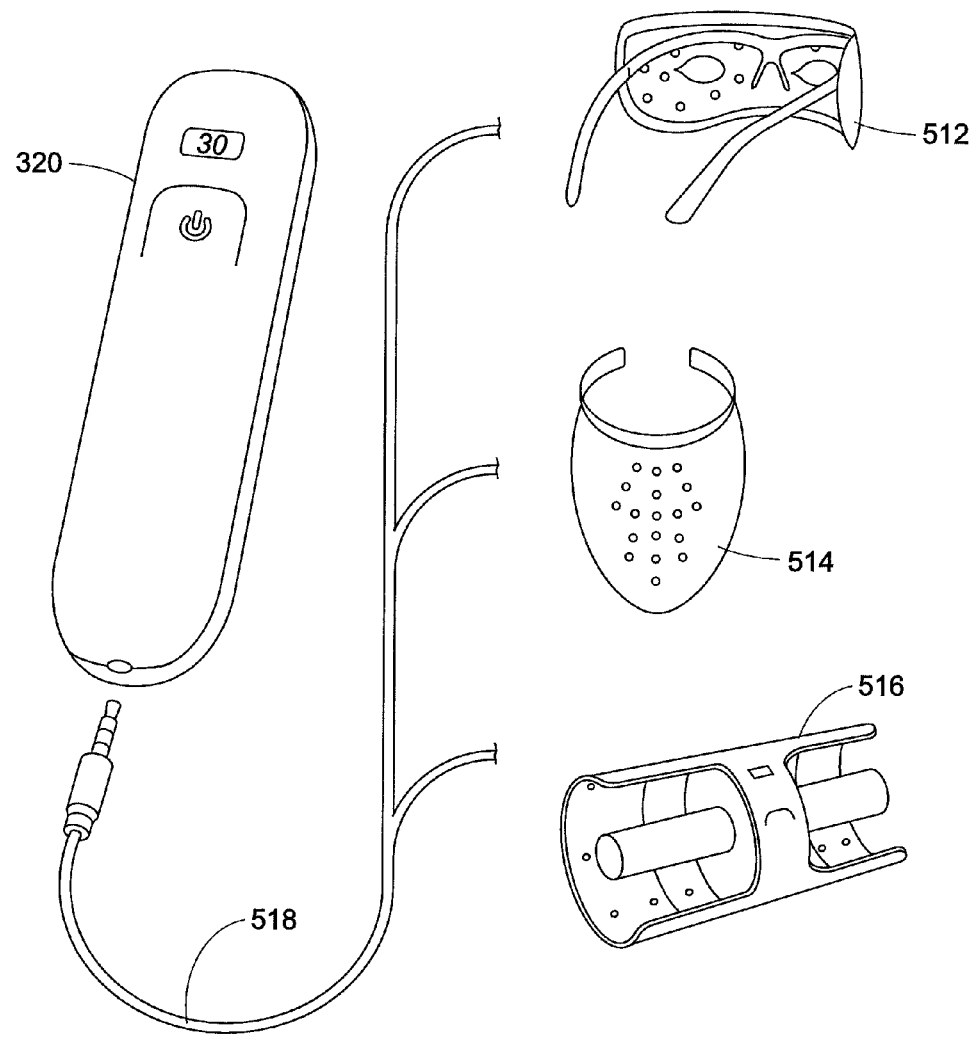
FIG. 29 is a system diagram including a therapeutic lamp platform controller simultaneously powering a plurality of phototherapy devices, including an Eye Mask, a Décolletage Device and a Hand Rejuvenation Device.

With reference to FIG. 29, shown is a system diagram including a therapeutic lamp platform controller 320 simultaneously powering a plurality of phototherapy devices, including an Eye Mask 512, a Décolletage Device 514 and a Hand Rejuvenation Device 516, operatively connected with cable 518. According to an exemplary embodiment, the controller multiplexes electrical power delivered to the phototherapy devices to utilize a limited power capacity of the device. Alternatively, the controller can include a sufficient battery capacity to drive all devices continuously and/or include separate LED driving circuits, one for each device.

Simultaneous powering of multiple phototherapy devices provides a manner of treating multiple user treatment areas at the same time. According to one exemplary embodiment, multiple treatment areas of a user's body are treated with one single dosage period. Alternatively, multiple dosage periods can be used where each device utilizes one dosage period. In addition, the controller is configured to execute program instructions to authenticate any device operatively attached to controller 320 via cable 518, for example, by executing a data handshake with the phototherapy device.

Figure 30:
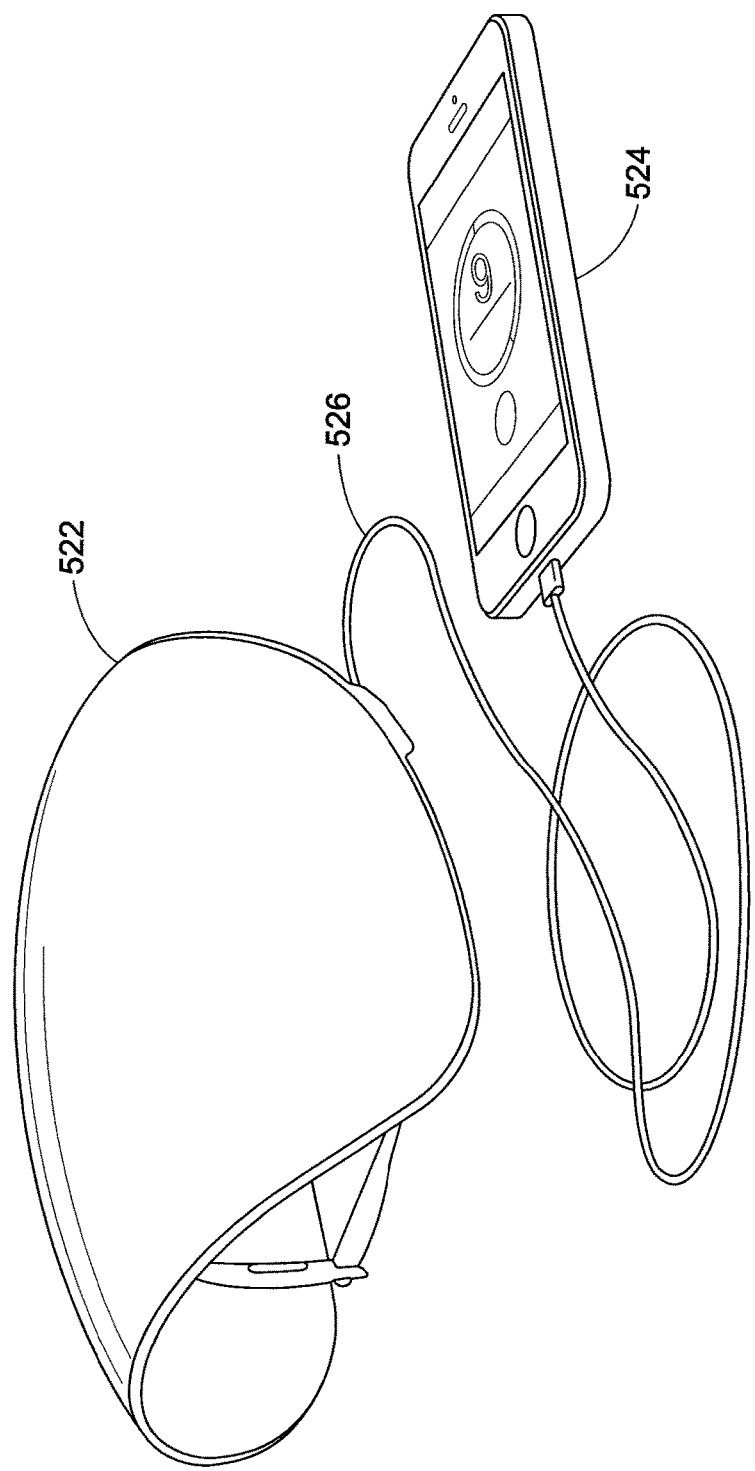
FIG. 30 illustrates a mobile device operatively associated with powering a therapeutic lamp platform according to an exemplary embedment of this disclosure.

With reference to FIG. 30, illustrated is a mobile device 524 operatively associated with powering a therapeutic lamp platform 522 using an operating connected cable according to an exemplary embedment of this disclosure.

According to an exemplary embodiment, the therapeutic lamp platform 522 is a reusable mask and mobile device 524 is a smart phone. The smart phone provides a platform to conduct ecommerce through the use of a lamp platform application where a user can electronically purchase additional dosages to be delivered by the mask 522. Cable 526 provides both power to the LEDs and enables authorization of the mask to "turn on", verifying that the user has a valid dose remaining, where circuitry housed within the mask communicates with the smart phone.

Due to power limitations, i.e. limited current draw, associated with some mobile devices, power to the mask LEDs can be multiplexed. For example, a smart phone supplies power at 3.5 volts at 150 mA to the mask, and control circuity housed within the mask multiplexes the array of mask LEDs to provide a reduced amount of radiation to the user treatment area, where an increased dosage period of time may be provided by the controller.

In addition to providing powering of the mask, the mobile device also can provide functionality and control of the mask. In other words, the mobile device provides the controller functionality previously described and also additional functionality, such as tracking of skin improvement using images of the treatment area captured by the mobile device camera.

Figure 31:
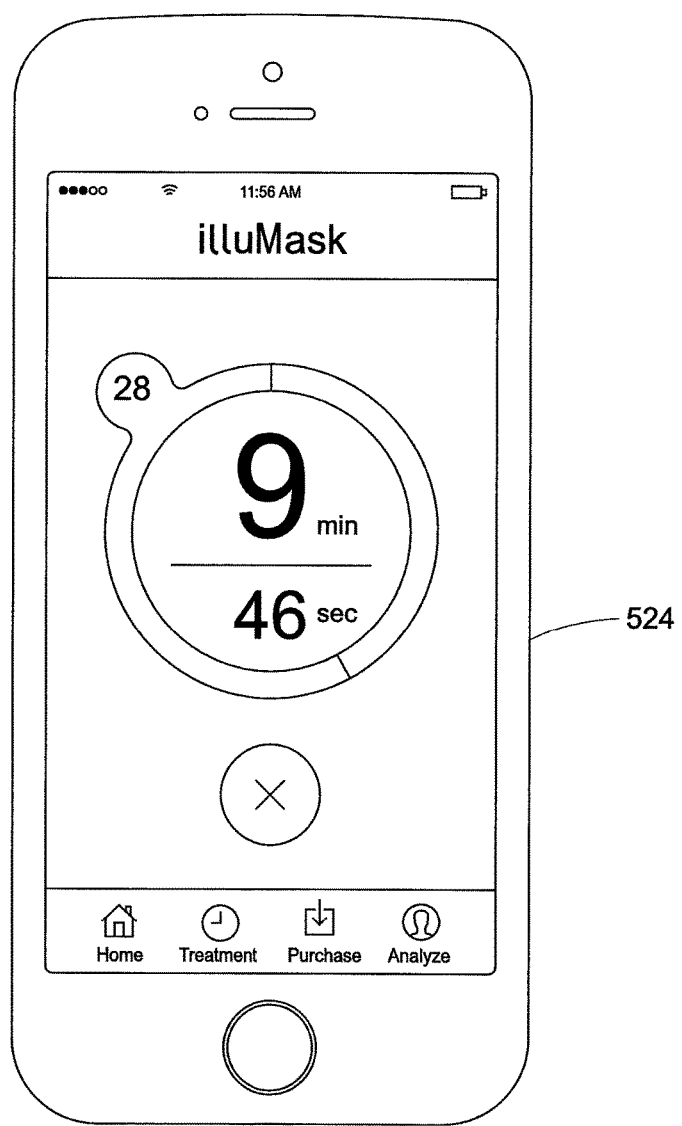
FIG. 31 is a detail view of the mobile device shown in FIG. 30.

With reference to FIG. 31, shown is a detail view of the mobile device shown in FIG. 30.

Figure 32B:
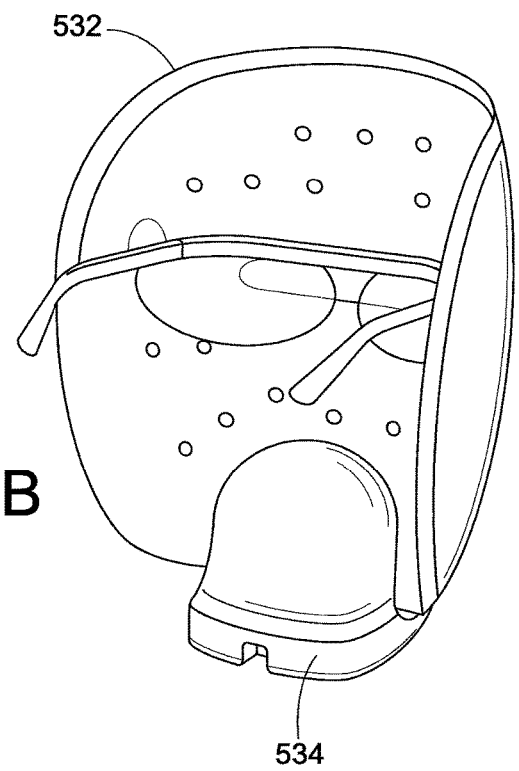
FIGS. 32A and 32B illustrate a therapeutic lamp platform including an inductively charged mask with an integrated controller, rechargeable battery, and inductive charger, according to an exemplary embodiment of this disclosure.
Figure 32A:
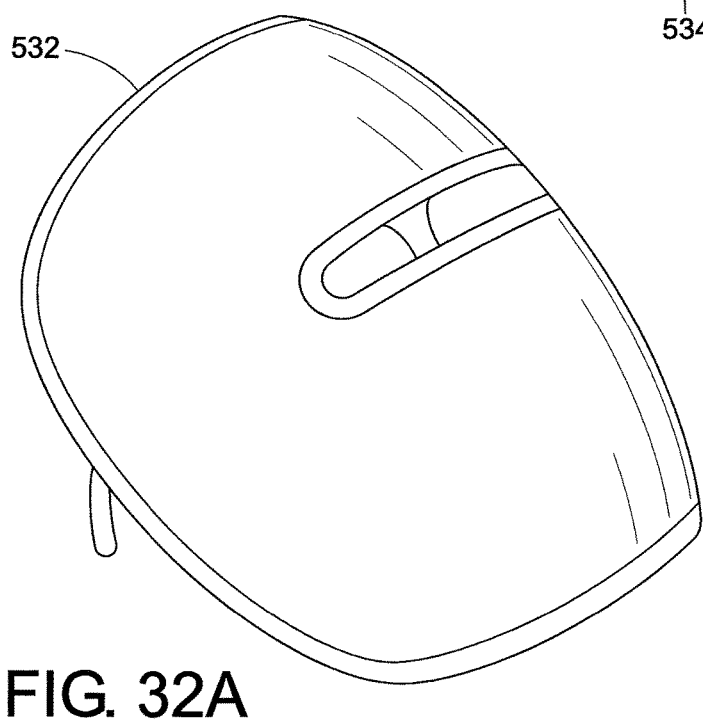

With reference to FIGS. 32A and 32B, illustrated is a therapeutic lamp platform including an inductively charged mask 532 with an integrated controller, rechargeable battery, and inductive charger 534, according to an exemplary embodiment of this disclosure.

With reference to FIGS. 33A and 33B, shown is the magnetic docking of an inductively charged therapeutic lamp platform 532 on an inductive charger 534 according to an exemplary embodiment of this disclosure.

Figure 34C:
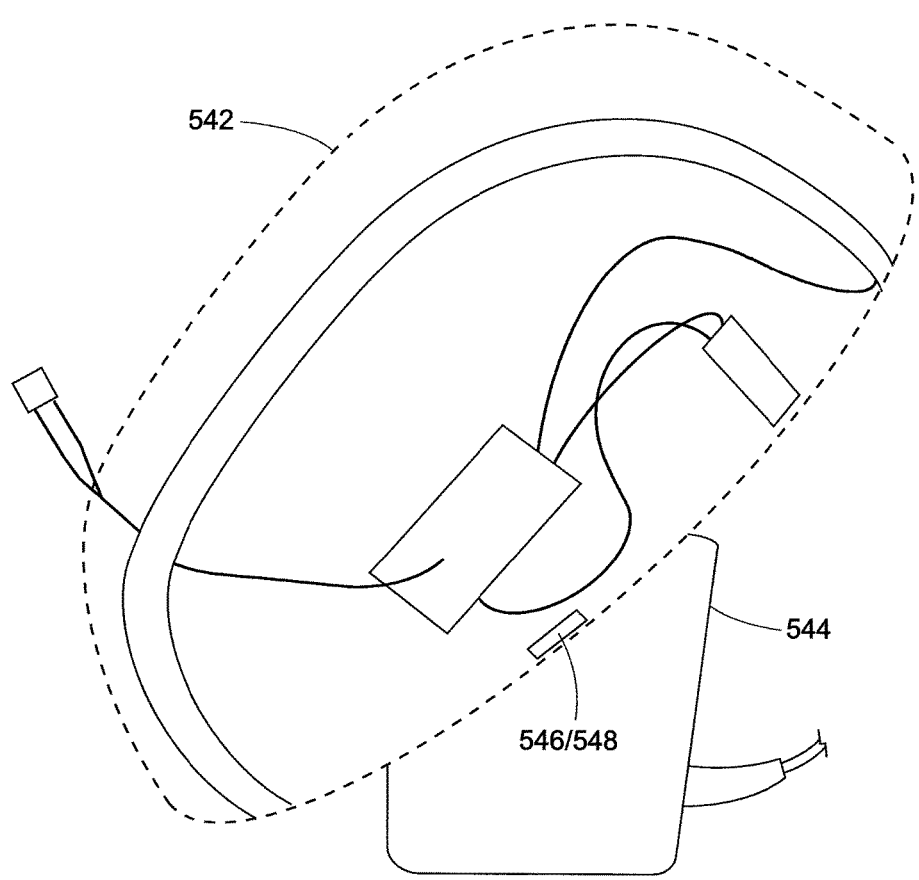

With reference to FIGS. 34A, 34B and 34C, further illustrated is the magnetic docking of an inductively chargeable therapeutic lamp platform 542 according to an exemplary embodiment of this disclosure.

As shown, the inductive charging system includes a mask 542 and an inductive charger 544. The mask 542 includes a charger coil 546 and the inductive charger 544 includes a corresponding charger coil 544. In addition, the mask 542 includes a light 550, a controller 552 and LED strips 554. During a charging operation, the mask charger coil 546 and the inductive charger coil 544 are operatively mated on the charging dock to inductively charge the mask battery, as shown in FIG. 34C.

Figure 35B:
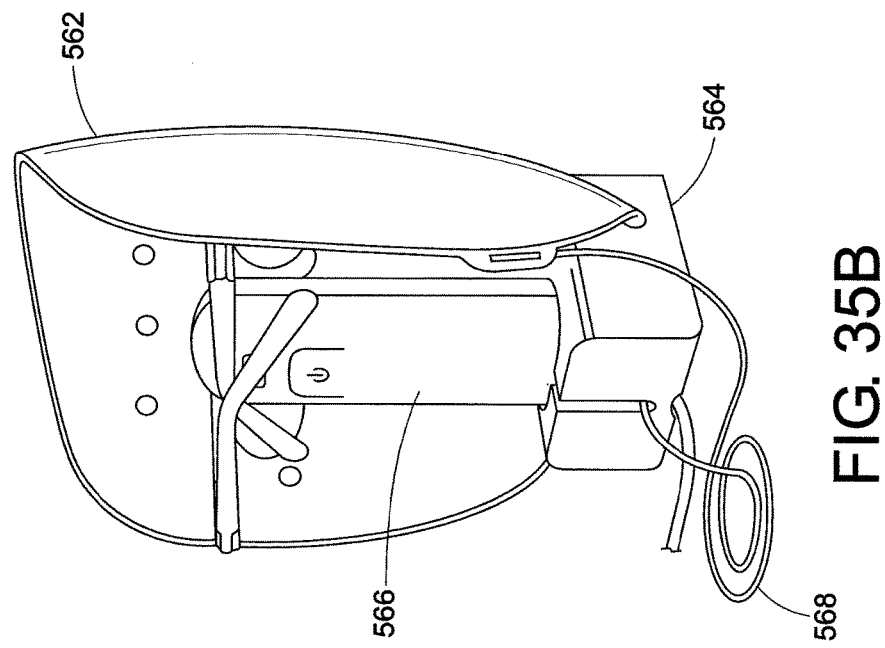
FIGS. 35A and 35B show a corded therapeutic lamp platform including an inductively charged controller and inductive charger.
Figure 35A:
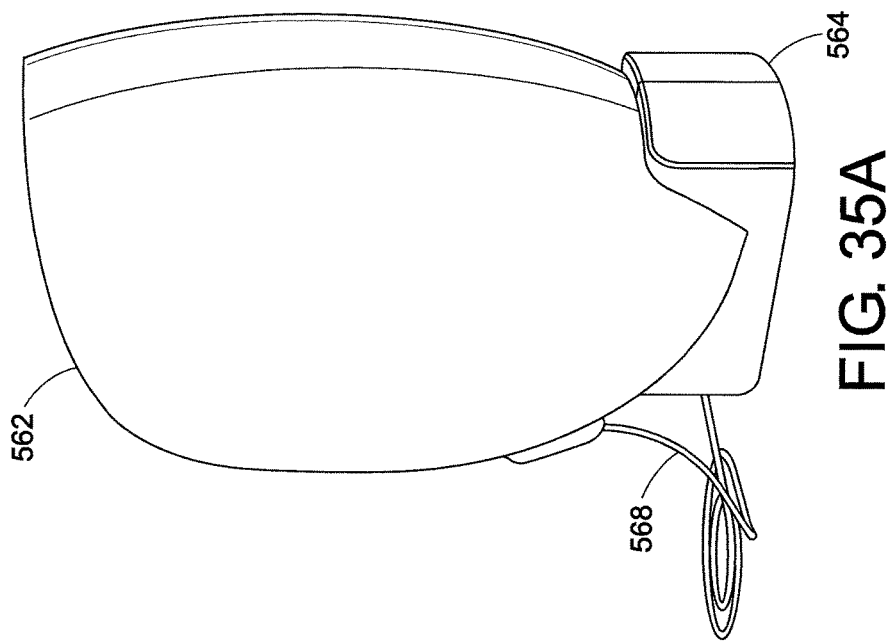

With reference to FIGS. 35A and 35B, shown is a corded 568 therapeutic lamp platform 562 including an inductively charged controller 566 and inductive charger 564.

Figure 36:
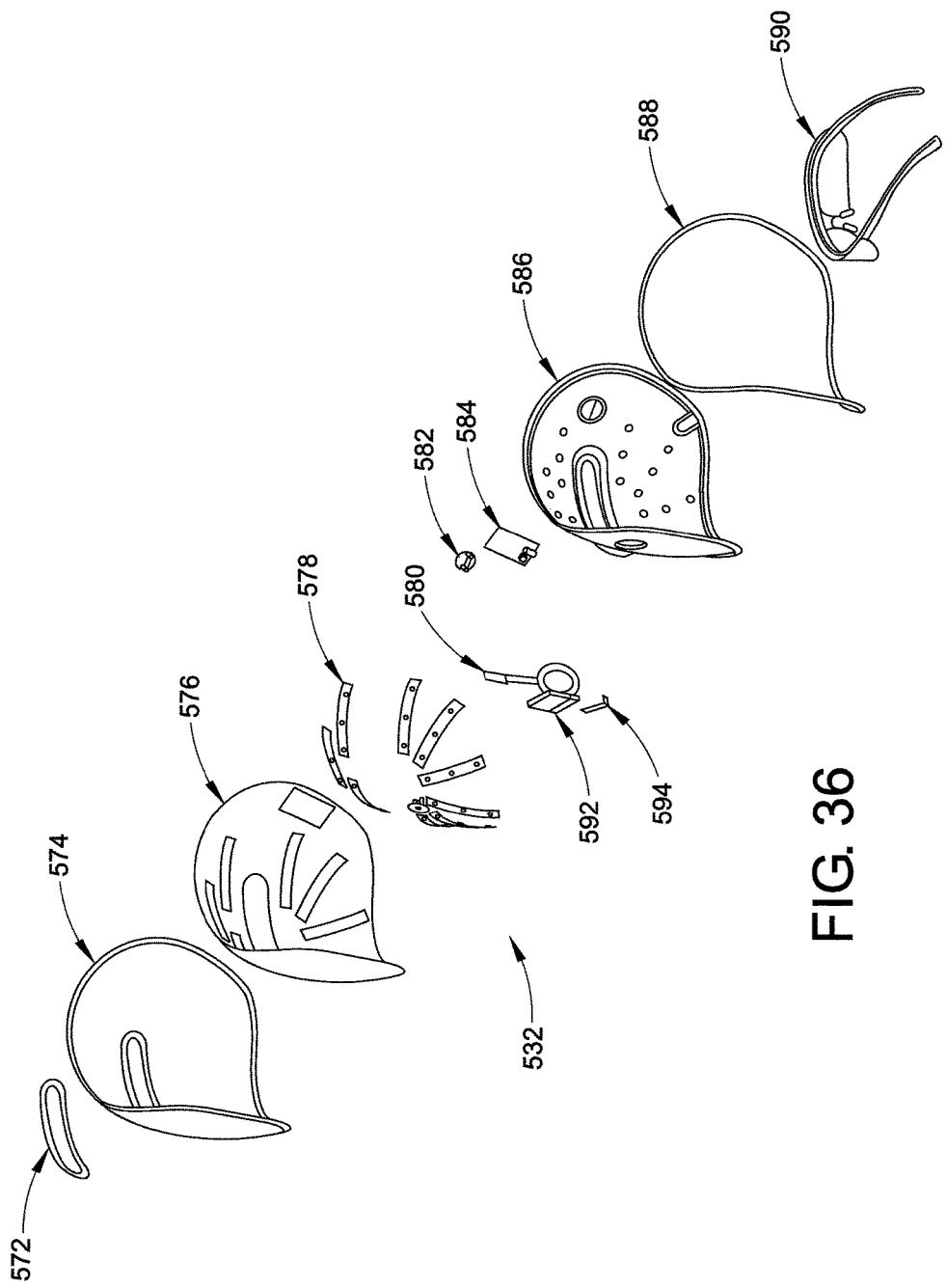
FIG. 36 is an exploded view of the inductively charged therapeutic lamp platform shown in FIG. 32.

With reference to FIG. 36, illustrated is an exploded view of the inductively charged therapeutic lamp platform 532 shown in FIG. 32.

As shown, the therapeutic lamp platform 532 includes a mask trim 572, outer layer 574, middle layer 576, LED strips 578, inductive charging assembly 580, locator plate 582, a PCB 584, inner layer 586, trim 588, eyeglass frame 590, LIPO battery 592 and trim 594.

According to an exemplary embodiment of a light therapy platform inductive mask and charger, the mask includes a parabolic shape, comfort glasses, 27 LEDs, view through window and integrated power button. The inductive charging technology shown in the figures provides wireless charging of the mask. In addition, magnetic docking the charger converts 110 VAC→an appropriate DC charging voltage, such as 5 VDC, and the magnetic alignment using the coils previously referred to provide for optimal alignment of the mask with the charger to efficiently charge the mask battery.

Figure 37:
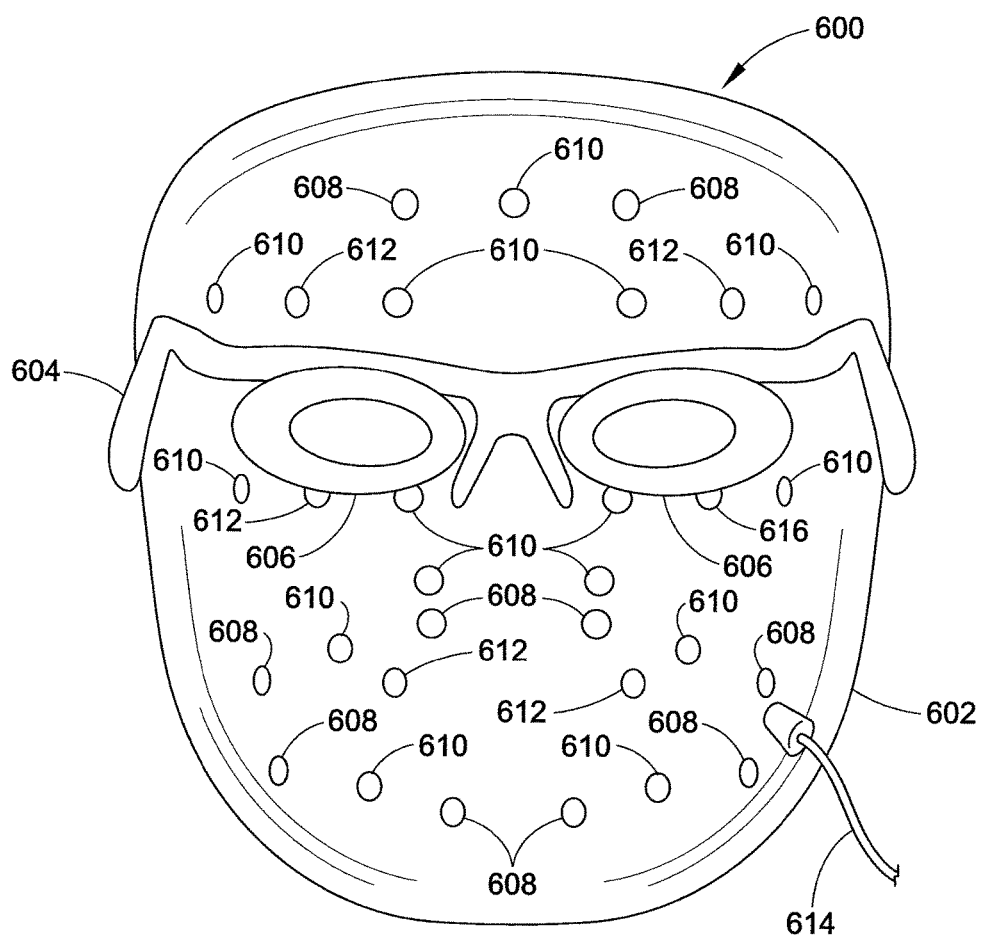
FIG. 37 illustrates a combination therapeutic lamp platform mask providing for a plurality of treatment radiation combinations, e.g. Acne and Anti-Aging, according to an exemplary embodiment of this disclosure.

With reference to FIG. 37, illustrated is a combination therapeutic lamp platform mask 600 providing for a plurality of treatment radiation combinations, e.g. Acne and Anti-Aging, according to an exemplary embodiment of this disclosure.

As shown, the combination therapeutic lamp platform includes mask structure 602, eyeglass frame 604, eye covers 606, LED1 608, LED2 610, LED3 612, and cable 614 which is operatively connected to a controller.

During operation, a user can select a desired treatment from one of a plurality of treatments provided by the mask LEDs placement, radiation wavelength and/or controller configuration.

Figure 38:
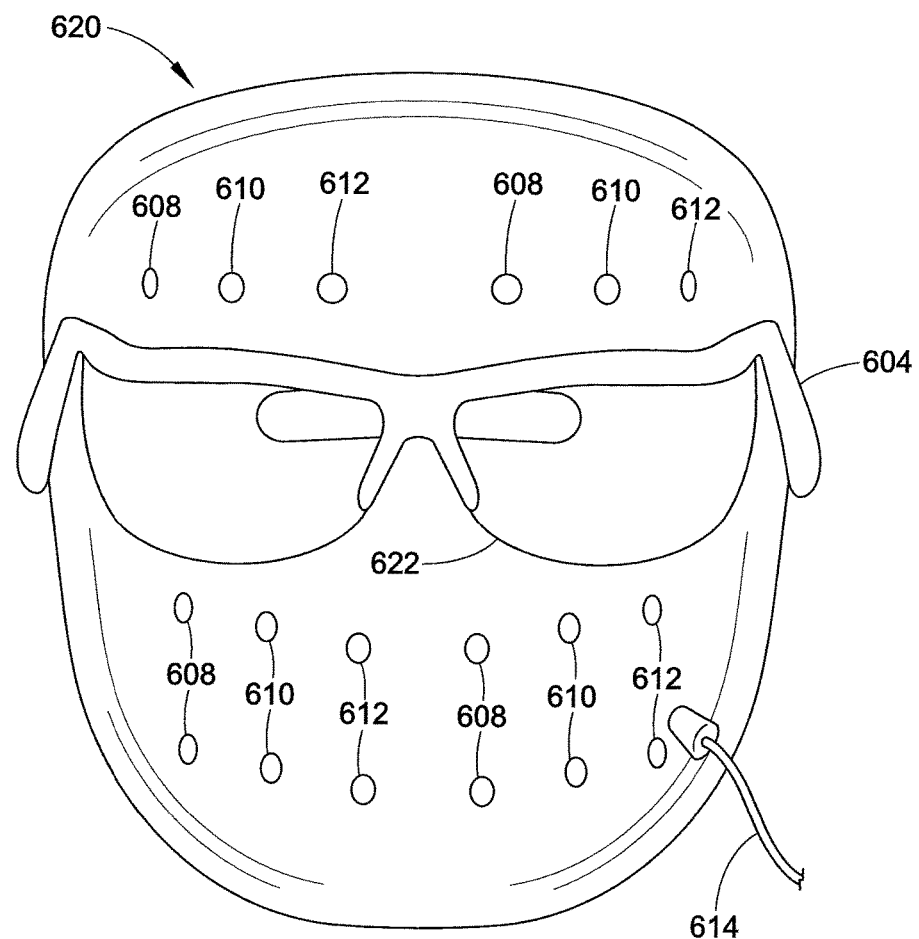
FIG. 38 illustrates another combination therapeutic lamp platform mask providing for a plurality of treatment radiation combinations, e.g. Acne and Anti-Aging, according to an exemplary embodiment of this disclosure.

With reference to FIG. 38, illustrated is another combination therapeutic lamp platform mask 620 providing for a plurality of treatment radiation combinations, e.g. Acne and Anti-Aging, according to an exemplary embodiment of this disclosure, where a lens 622 is provided.

Other variations of the combination lamp platform mask include a specific layout of LEDs for each treatment, for example anti-aging radiation LEDs aligned to areas of the face normally affected by age. Another example includes aligning acne LEDs to key facial features in the T-zone and around the jawline.

Furthermore, control variations include a combination treatment where all LEDs are radiating simultaneously to provide a plurality of treatments, such as acne and anti-aging; configurable controller settings for a user to choose a specific treatment and treatment schedule; and configurable controller settings to program the mask to start with a first treatment and run until completion and then begin a second treatment.

According to another exemplary embodiment of a combination lamp platform, multi-color LEDs are mounted to the mask, the multi-color LEDs wavelength, i.e. color, controllable by the device controller to select a treatment regimen they would like to implement and the appropriate LEDs, along with radiation wavelength, are activated. Other control options include cycling the LED colors through various treatment modes, providing simultaneous treatment of multiple skin conditions, and allowing the user to program which areas of their face require specific treatments, e.g. acne on the forehead and anti-aging around smile lines, where the control software turns on the appropriate LED in these specific facial regions. Furthermore, the combination lamp platform can be connected to a mobile device such as a smart phone with a dedicated application, an image of the user treatment area captured by the smart phone and the software application performs an analysis of the user's skin condition(s) and custom tailors the LED treatment regimen based on the image analysis.

With reference to FIGS. 39A and 39B, illustrated is a therapeutic lamp platform configured to stimulate hair growth according to an exemplary embodiment of this disclosure.

As shown in FIG. 39A, the therapeutic lamp platform, i.e., hair growth light therapy device 630, includes a LED 636 support structure 632 attached to a head band 634. FIG. 39B shows a hair growth light therapy device 640 including an extended LED support structure 642 for additional coverage of a scalp.

To use the device 630, a user uses the headband 634 to removably attach the device to the scalp area, where the placement of the headband behind the users ears provide positioning of the LEDs as indicated.

Figure 40B:
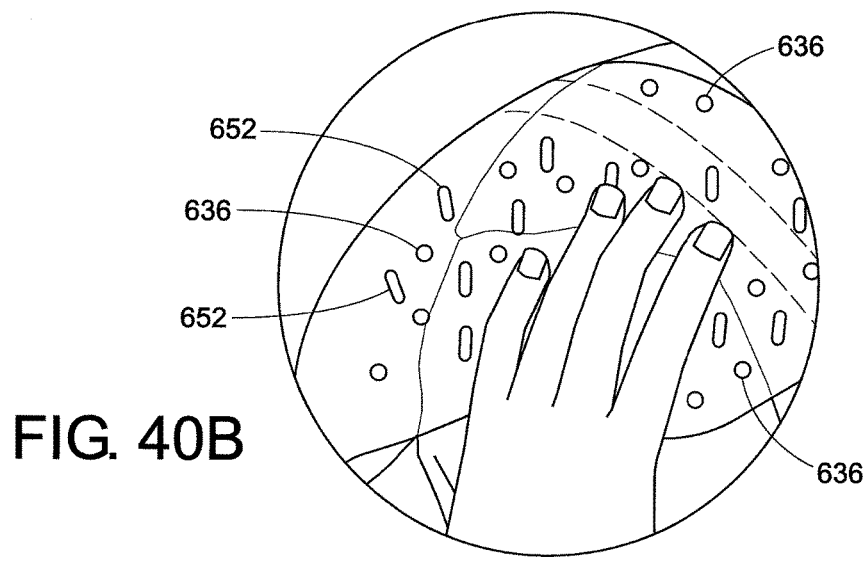
FIGS. 40A and 40B illustrate a therapeutic lamp platform configured to stimulate hair growth including an integrated comb according to an exemplary embodiment of this disclosure.
Figure 40A:
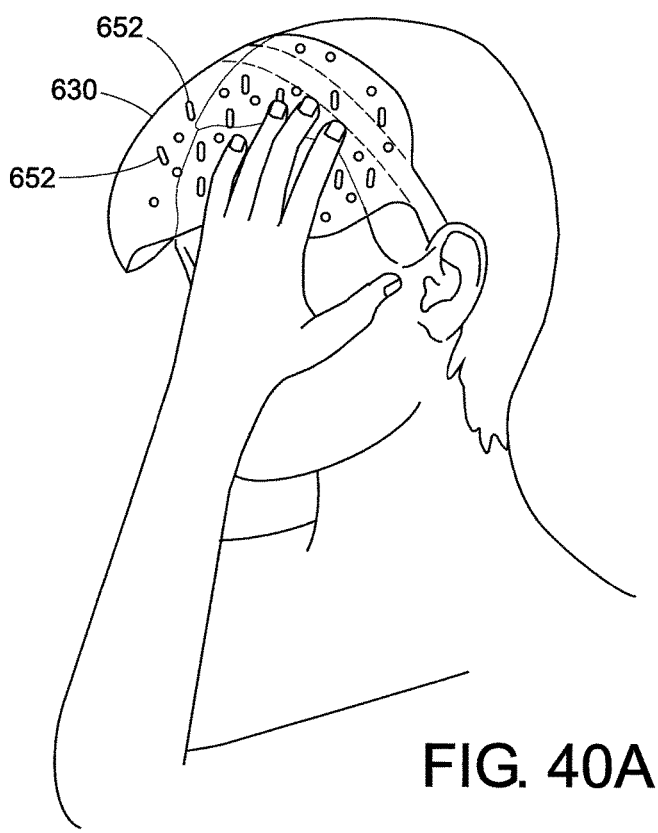

With reference to FIGS. 40A and 40B, illustrated is a therapeutic lamp platform configured to stimulate hair growth including an integrated comb 652 according to an exemplary embodiment of this disclosure. The integrated comb bristles provide parting of hair to improve the efficiency of the radiation treatment provided by LEDs 636.

With reference to FIGS. 41A and 41B, shown are detail views of LED/Brush Bristle configurations for a therapeutic lamp platform 630 and 640 configured to stimulate hair growth. Part lines 662 are provided by brush/bristles 652, and a recessed hair line is indicated as reference character 664 and crown area by reference character 666.

With reference to FIGS. 42A and 42B, illustrated are detail views of radiant energy scalp coverage 674 and 684 associated with an exemplary embodiment of a therapeutic lamp platform configured to stimulate hair including LEDs 636 without an associated light pipe, and with an associated light pipe 682, respectively.

As shown in FIG. 42A, the therapeutic lamp platform includes an outer housing 672, and LED 636 with generating radiation cone 674 providing hair growth coverage on a scalp 676, including hair follicles 678.

In comparison, FIG. 42B includes a light pipe 682 which provides a radiation cone 684 which is narrower than radiation cone 674, but has the advantage of an increased in radiation intensity for a given controller output, controlled by the light pipe diameter.

With reference to FIGS. 43A and 43B, shown are further detail views of radiant energy scalp coverage associated with a therapeutic lamp platform without a light pipe and with a light pipe, respectively, as shown in FIGS. 42A and 42B.

Figure 44B:
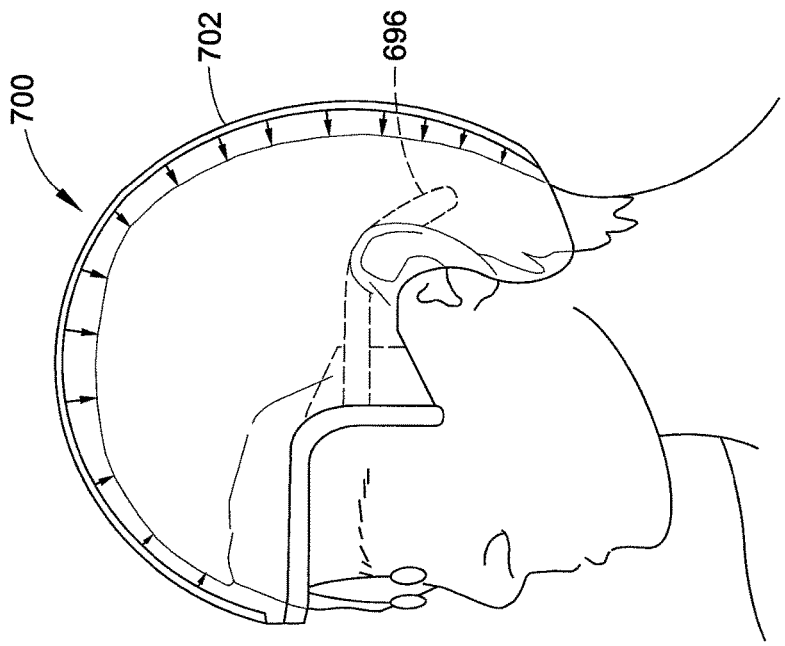
FIGS. 44A and 44B illustrate another therapeutic lamp platform configured to stimulate hair growth including an eye glass frame and reflective layer, according to an exemplary embodiment of this disclosure.
Figure 44A:
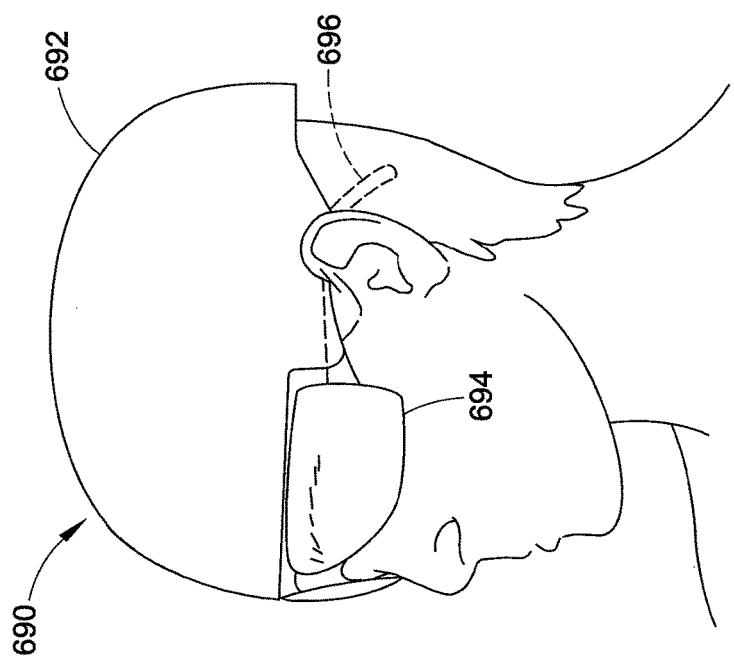

With reference to FIGS. 44A and 44B, illustrated is another therapeutic lamp platform 690 and 700 configured to stimulate hair growth including a helmet design with an eye glass frame 696 reflective layer 702 and lens 694, according to an exemplary embodiment of this disclosure.

Figure 45:
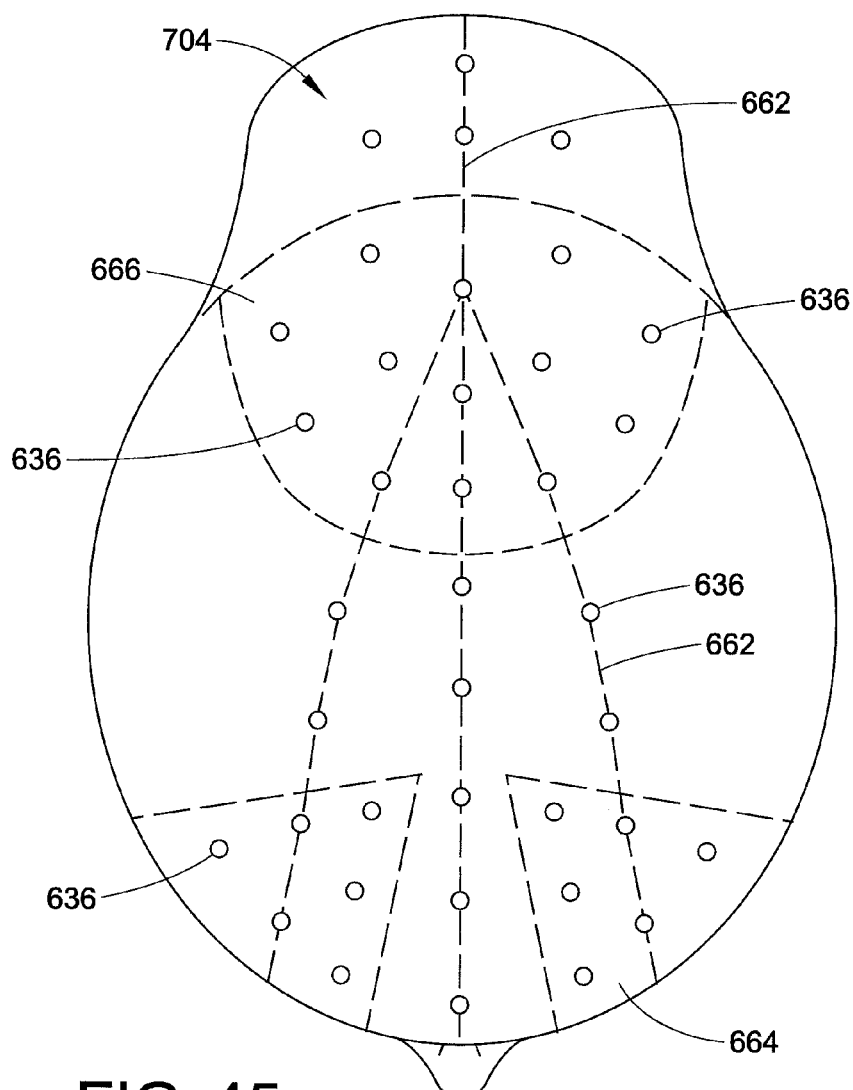
FIG. 45 is a detail view of an LED configuration of a therapeutic lamp platform configured to stimulate hair growth as shown in FIGS. 44A and 44B.

With reference to FIG. 45, shown is a detail view of an LED configuration of a therapeutic lamp platform configured to stimulate hair growth as shown in FIGS. 44A and 44B, where LEDs 636 are aligned along part lines 662 associated with recessed hair line 664 and crown 666. Area 704 is associated with an extended coverage area provided by the lamp platform. This configuration provides a radiation bath which targets all problem areas at once. A reflective layer attached to the inside surface of the helmet provides a more intense treatment.

With reference to FIGS. 46A and 46B, illustrated is another therapeutic lamp platform configured to stimulate hair growth including a helmet 710 according to an exemplary embodiment of this disclosure. The hair growth lamp platform includes a plurality of LEDs mounted to a shell 712, where an adjustable tensioner 714 and knob arrangement control the fitting of the helmet to a user's head. Extra padding at the back of the helmet provides additional support and comfort.

Figure 47:
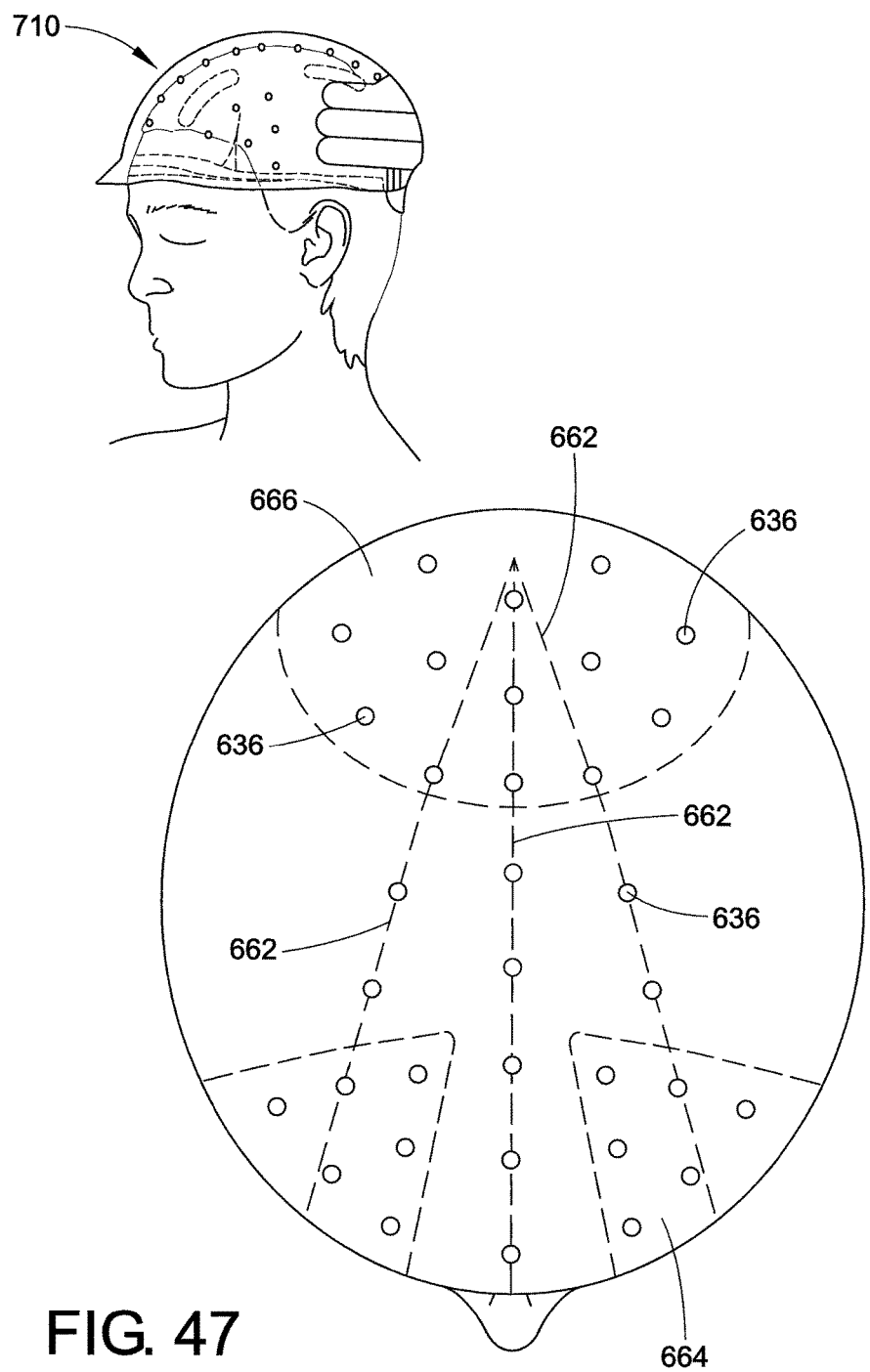
FIG. 47 is a detailed view of an LED configuration of a therapeutic lamp platform as shown in FIGS. 45A and 45B, configured to stimulate hair growth according to an exemplary embodiment of this disclosure.

With reference to FIG. 47, shown is a detailed view of an LED 636 configuration of a therapeutic lamp platform as shown in FIGS. 45A and 45B, configured to stimulate hair growth according to an exemplary embodiment of this disclosure. As shown, the detailed view includes a crown area 666, recessed hair line area, and part lines 662 which are substantially aligned with LEDs 636.

Some portions of the detailed description herein are presented in terms of algorithms and symbolic representations of operations on data bits performed by conventional computer components, including a central processing unit (CPU), memory storage devices for the CPU, and connected display devices. These algorithmic descriptions and representations are the means used by those skilled in the data processing arts to most effectively convey the substance of their work to others skilled in the art. An algorithm is generally perceived as a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be understood, however, that all of these and similar terms are to be associated with the appropriate physical quantities and are merely convenient labels applied to these quantities. Unless specifically stated otherwise, as apparent from the discussion herein, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The exemplary embodiment also relates to an apparatus for performing the operations discussed herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general-purpose systems may be used with programs in accordance with the teachings herein, or it may prove convenient to construct more specialized apparatus to perform the methods described herein. The structure for a variety of these systems is apparent from the description above. In addition, the exemplary embodiment is not described with reference to any particular programming language. It will be appreciated that a variety of programming languages may be used to implement the teachings of the exemplary embodiment as described herein.

A machine-readable medium includes any mechanism for storing or transmitting information in a form readable by a machine (e.g., a computer). For instance, a machine-readable medium includes read only memory ("ROM"); random access memory ("RAM"); magnetic disk storage media; optical storage media; flash memory devices; and electrical, optical, acoustical or other form of propagated signals (e.g., carrier waves, infrared signals, digital signals, etc.), just to mention a few examples.

The methods illustrated throughout the specification, may be implemented in a computer program product that may be executed on a computer. The computer program product may comprise a non-transitory computer-readable recording medium on which a control program is recorded, such as a disk, hard drive, or the like. Common forms of non-transitory computer-readable media include, for example, floppy disks, flexible disks, hard disks, magnetic tape, or any other magnetic storage medium, CD-ROM, DVD, or any other optical medium, a RAM, a PROM, an EPROM, a FLASH-EPROM, or other memory chip or cartridge, or any other tangible medium from which a computer can read and use.

Alternatively, the method may be implemented in transitory media, such as a transmittable carrier wave in which the control program is embodied as a data signal using transmission media, such as acoustic or light waves, such as those generated during radio wave and infrared data communications, and the like.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:

1. A phototherapy device comprising:
a wearable therapeutic lamp platform including a plurality of radiant lamps emitting radiant energy at two or more wavelengths and a reflective wall including an external reflective surface directed towards a user treatment area, the external reflective surface including a plurality of radiant energy communication areas aligned with the plurality of radiant lamps and disposed to communicate the radiant energy to the user treatment area, each of the plurality of radiant energy communication areas aligned with a single respective radiant lamp and wherein the reflective wall is further formed to disperse over the user treatment area radiant energy reflected from the user treatment area back to the user treatment area; and
a frame adapted to support the therapeutic lamp platform on the user and adapted to position the therapeutic lamp platform on the user, the frame positioning the reflective wall towards the first and second user treatment areas and spacing the reflective wall from the first and second user treatment areas, the reflective wall covering a complete nose of the user and the reflective wall spaced from the complete nose of the user to provide ventilation and clearance between the reflective wall and the complete nose of the user; and
wherein the therapeutic lamp platform includes an inductively chargeable power source operatively connected to the plurality of radiant lamps and configured to receive an inductive charge from an operatively associated inductive charger.

2. The phototherapy device according to claim 1, wherein the wearable therapeutic lamp platform is configured to provide radiant energy for one or both of acne treatment and anti-aging treatment.

3. The phototherapy device according to claim 1, wherein the wearable therapeutic lamp platform includes an integrated controller configured to drive the plurality of radiant lamps, and the plurality of radiant lamps includes a mixed combination of different wavelength radiant energy.

4. The phototherapy device according to claim 1, wherein the wearable therapeutic lamp platform includes a user control switch.

5. The phototherapy device according to claim 1, wherein the inductive charger includes a docking area configured to physically support the therapeutic lamp platform while the inductively chargeable power source is being charged by the inductive charger.

6. The phototherapy device according to claim 1, wherein the wearable therapeutic lamp platform includes a charging port operatively connected to the inductively chargeable power source.

7. The phototherapy device according to claim 1, wherein the wearable therapeutic lamp platform is mask shaped.

8. The phototherapy device according to claim 7, wherein the wearable therapeutic lamp platform includes an integrated controller operatively connected to the plurality of radiant lamps and the inductively chargeable power system.

9. The phototherapy device according to claim 8, wherein the wearable therapeutic lamp platform includes a user control switch operatively connected to the integrated controller.

10. A phototherapy device comprising:
a wearable therapeutic lamp platform including a plurality of radiant lamps including a mixed combination of different wavelength radiant energy and a malleable flexible reflective wall including an external reflective surface, the external reflective surface including a plurality of apertures optically aligned with the plurality of radiant lamps and disposed to communicate the radiant energy to a user treatment area, each of the plurality of apertures aligned with a single respective radiant lamp and wherein the reflective wall is further formed according to a substantially parabolic bias for dispersing the radiant energy across the user treatment area and reflecting the radiant energy from the user treatment area back to the user treatment area, and wherein upon device receipt on a user the reflective wall parabolic bias expands to a form to match a size of the user treatment area; and
a frame adapted to support the therapeutic lamp platform on the user and adapted to position the therapeutic lamp platform on the user, the frame positioning the reflective wall towards the first and second user treatment areas and spacing the reflective wall from the first and second user treatment areas, the reflective wall covering a complete nose of the user and the reflective wall spaced from the complete nose of the user to provide ventilation and clearance between the reflective wall and the complete nose of the user; and
wherein the therapeutic lamp platform includes an inductively chargeable power source operatively connected to the plurality of radiant lamps and configured to receive an inductive charge from an operatively associated inductive charger.

11. A phototherapy device comprising:
a wearable therapeutic lamp platform including a plurality of radiant lamps including a mixed combination of different wavelength radiant energy and a malleable flexible reflective wall including an external reflective surface, the external reflective surface including a plurality of apertures optically aligned with the radiant lamps and disposed to communicate the radiant energy to a user treatment area, each of the plurality of apertures aligned with a single respective radiant lamp and wherein the reflective wall is further formed according to a substantially parabolic bias for dispersing the radiant energy across the user treatment area and reflecting the radiant energy from the user treatment area back to the user treatment area, and wherein upon device receipt on a user, the reflective wall parabolic bias expands to a form to match a size of the user treatment area; and
a frame adapted to support the therapeutic lamp platform on the user and adapted to position the therapeutic lamp platform on the user, the frame positioning the reflective wall towards the first and second user treatment areas and spacing the reflective wall from the first and second user treatment areas, the reflective wall covering a complete nose of the user and the reflective wall spaced from the complete nose of the user to provide ventilation and clearance between the reflective wall and the complete nose of the user;

wherein the therapeutic lamp platform includes an inductively chargeable power source operatively connected to the plurality of radiant lamps and configured to receive an inductive charge from an operatively associated inductive charger.

12. The phototherapy device according to claim 11, wherein the wearable therapeutic lamp platform is configured to provide radiant energy for one or both of acne treatment and anti-aging treatment.

13. The phototherapy device according to claim 11, wherein the wearable therapeutic lamp platform includes an integrated controller configured to drive the plurality of radiant lamps, and the plurality of radiant lamps includes a mixed combination of different wavelength radiant energy.

14. The phototherapy device according to claim 11, wherein the wearable therapeutic lamp platform includes a user control switch.

15. The phototherapy device according to claim 11, wherein the inductive charger includes a docking area configured to physically support the therapeutic lamp platform while the inductively chargeable power source is being charged by the inductive charger.

16. The phototherapy device according to claim 11, wherein the wearable therapeutic lamp platform includes a charging port operatively connected to the inductively chargeable power source.

17. The phototherapy device according to claim 11, wherein the wearable therapeutic lamp platform is mask shaped.

18. The phototherapy device according to claim 17, wherein the wearable therapeutic lamp platform includes an integrated controller operatively connected to the plurality of radiant lamps and the inductively chargeable power system.

19. The phototherapy device according to claim 18, wherein the wearable therapeutic lamp platform includes a user control switch operatively connected to the integrated controller.

* * * * *